US009458189B2

(12) United States Patent
Verdine et al.

(10) Patent No.: US 9,458,189 B2
(45) Date of Patent: Oct. 4, 2016

(54) LIGATION OF STAPLED POLYPEPTIDES

(71) Applicant: President and Fellows of Harvard College, Cambridge, MA (US)

(72) Inventors: Gregory L. Verdine, Boston, MA (US); Eileen Jeanne Kennedy, Athens, GA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/748,287

(22) Filed: Jun. 24, 2015

(65) Prior Publication Data

US 2015/0376227 A1    Dec. 31, 2015

Related U.S. Application Data

(62) Division of application No. 13/055,279, filed as application No. PCT/US2009/004260 on Jul. 23, 2009, now abandoned.

(60) Provisional application No. 61/082,935, filed on Jul. 23, 2008, provisional application No. 61/225,191, filed on Jul. 13, 2009.

(51) Int. Cl.
| C07K 1/107 | (2006.01) |
| C07K 14/47 | (2006.01) |
| C07K 14/54 | (2006.01) |
| A61K 38/17 | (2006.01) |
| A61K 38/20 | (2006.01) |
| A61K 38/00 | (2006.01) |

(52) U.S. Cl.
CPC ........... *C07K 1/107* (2013.01); *A61K 38/1709* (2013.01); *A61K 38/2086* (2013.01); *C07K 14/4702* (2013.01); *C07K 14/5437* (2013.01); *A61K 38/00* (2013.01)

(58) Field of Classification Search
None
See application file for complete search history.

(56) References Cited

U.S. PATENT DOCUMENTS

| 4,270,537 | A | 6/1981 | Romaine |
| 4,596,556 | A | 6/1986 | Morrow et al. |
| 4,730,006 | A | 3/1988 | Bohme et al. |
| 4,790,824 | A | 12/1988 | Morrow et al. |
| 4,886,499 | A | 12/1989 | Cirelli et al. |
| 4,940,460 | A | 7/1990 | Casey et al. |
| 4,941,880 | A | 7/1990 | Burns |
| 5,015,235 | A | 5/1991 | Crossman |
| 5,064,413 | A | 11/1991 | McKinnon et al. |
| 5,120,859 | A | 6/1992 | Webb |
| 5,141,496 | A | 8/1992 | Dalto et al. |
| 5,190,521 | A | 3/1993 | Hubbard et al. |
| 5,312,335 | A | 5/1994 | McKinnon et al. |
| 5,328,483 | A | 7/1994 | Jacoby |
| 5,334,144 | A | 8/1994 | Alchas et al. |
| 5,339,163 | A | 8/1994 | Homma et al. |
| 5,364,851 | A | 11/1994 | Joran |
| 5,383,851 | A | 1/1995 | McKinnon et al. |
| 5,417,662 | A | 5/1995 | Hjertman et al. |
| 5,446,128 | A | 8/1995 | Kahn |
| 5,466,220 | A | 11/1995 | Brenneman |
| 5,480,381 | A | 1/1996 | Weston |
| 5,503,627 | A | 4/1996 | McKinnon et al. |
| 5,520,639 | A | 5/1996 | Peterson et al. |
| 5,527,288 | A | 6/1996 | Gross et al. |
| 5,569,189 | A | 10/1996 | Parsons |
| 5,599,302 | A | 2/1997 | Lilley et al. |
| 5,622,852 | A | 4/1997 | Korsmeyer |
| 5,649,912 | A | 7/1997 | Peterson |
| 5,663,316 | A | 9/1997 | Xudong |
| 5,704,911 | A | 1/1998 | Parsons |
| 5,708,136 | A | 1/1998 | Burrell et al. |
| 5,750,767 | A | 5/1998 | Carpino et al. |
| 5,811,515 | A | 9/1998 | Grubbs et al. |
| 5,824,483 | A | 10/1998 | Houston, Jr. et al. |
| 5,834,209 | A | 11/1998 | Korsmeyer |
| 5,856,445 | A | 1/1999 | Korsmeyer |
| 5,874,529 | A | 2/1999 | Gilon et al. |
| 5,893,397 | A | 4/1999 | Peterson et al. |
| 5,922,863 | A | 7/1999 | Grubbs et al. |
| 5,955,593 | A | 9/1999 | Korsmeyer |
| 5,965,703 | A | 10/1999 | Horne et al. |
| 5,993,412 | A | 11/1999 | Deily et al. |
| 5,998,583 | A | 12/1999 | Korsmeyer |
| 6,051,554 | A | 4/2000 | Hornik et al. |
| 6,153,391 | A | 11/2000 | Picksley et al. |
| 6,184,344 | B1 | 2/2001 | Kent et al. |

(Continued)

FOREIGN PATENT DOCUMENTS

| WO | WO 96/02642 A1 | 2/1996 |
| WO | WO 96/20951 A1 | 7/1996 |

(Continued)

OTHER PUBLICATIONS

Extended European Search Report for EP 10800148.8, mailed Oct. 16, 2013.
Invitation to Pay Additional Fees for PCT/US2010/001952, mailed Oct. 29, 2010.
International Search Report and Written Opinion for PCT/US2010/001952, mailed Feb. 2, 2011.
International Preliminary Report on Patentability for PCT/US2010/001952, mailed Jan. 26, 2012.
Extended European Search Report for EP 09800675.2, mailed Dec. 6, 2012.
Invitation to Pay Additional Fees for PCT/US2009/004260, mailed Mar. 19, 2010.

(Continued)

*Primary Examiner* — Christina Bradley
(74) *Attorney, Agent, or Firm* — Wolf, Greenfield & Sacks, P.C.

(57) ABSTRACT

The present invention provides technology for making large (e.g., greater than 50 amino acids), semi-synthetic, stapled or stitched proteins. The method essentially involves ligating a synthetically produced stapled or stitched peptide to a larger protein. Modified version of IL-13 and MYC are provided as illustrative examples.

22 Claims, 30 Drawing Sheets

(56) References Cited

U.S. PATENT DOCUMENTS

| | | |
|---|---|---|
| 6,271,198 B1 | 8/2001 | Braisted et al. |
| 6,326,354 B1 | 12/2001 | Gross et al. |
| 6,610,657 B1 | 8/2003 | Goueli |
| 6,613,874 B1 | 9/2003 | Mazur et al. |
| 6,703,382 B2 | 3/2004 | Wang et al. |
| 6,713,280 B1 | 3/2004 | Huang et al. |
| 6,849,428 B1 | 2/2005 | Evans et al. |
| 6,875,594 B2 | 4/2005 | Muir et al. |
| 7,064,193 B1 | 6/2006 | Cory et al. |
| 7,083,983 B2 | 8/2006 | Lane et al. |
| 7,084,244 B2 | 8/2006 | Gilon et al. |
| 7,183,059 B2 | 2/2007 | Verdine et al. |
| 7,192,713 B1 | 3/2007 | Verdine et al. |
| 7,202,332 B2 | 4/2007 | Arora et al. |
| 7,247,700 B2 | 7/2007 | Korsmeyer et al. |
| 7,538,190 B2 | 5/2009 | Robinson et al. |
| 7,705,118 B2 | 4/2010 | Arora et al. |
| 7,723,469 B2 | 5/2010 | Walensky et al. |
| 7,745,573 B2 | 6/2010 | Robinson et al. |
| 7,786,072 B2 | 8/2010 | Verdine et al. |
| 8,324,428 B2 | 12/2012 | Verdine et al. |
| 8,592,377 B2 | 11/2013 | Verdine et al. |
| 8,895,699 B2 | 11/2014 | Verdine et al. |
| 8,957,026 B2 | 2/2015 | Verdine et al. |
| 9,163,330 B2 | 10/2015 | Verdine et al. |
| 2004/0038901 A1 | 2/2004 | Basler et al. |
| 2004/0067503 A1 | 4/2004 | Tan et al. |
| 2004/0171809 A1 | 9/2004 | Korsmeyer et al. |
| 2005/0250680 A1 | 11/2005 | Walensky et al. |
| 2006/0008848 A1 | 1/2006 | Verdine et al. |
| 2006/0014675 A1 | 1/2006 | Arora et al. |
| 2006/0148715 A1 | 7/2006 | Tweardy |
| 2008/0262200 A1 | 10/2008 | Nash |
| 2009/0047711 A1 | 2/2009 | Nash |
| 2009/0088553 A1 | 4/2009 | Nash |
| 2009/0149630 A1 | 6/2009 | Walensky et al. |
| 2009/0176964 A1 | 7/2009 | Walensky et al. |
| 2009/0326192 A1 | 12/2009 | Nash et al. |
| 2010/0081611 A1 | 4/2010 | Bradner et al. |
| 2010/0168388 A1 | 7/2010 | Bernal et al. |
| 2010/0184628 A1 | 7/2010 | Nash |
| 2010/0184645 A1 | 7/2010 | Verdine et al. |
| 2010/0216688 A1 | 8/2010 | Nash et al. |
| 2010/0234563 A1 | 9/2010 | Arora et al. |
| 2010/0298201 A1 | 11/2010 | Nash et al. |
| 2011/0028753 A1 | 2/2011 | Verdine et al. |
| 2011/0144303 A1 | 6/2011 | Nash et al. |
| 2011/0144306 A1 | 6/2011 | Verdine et al. |
| 2011/0223149 A1 | 9/2011 | Nash et al. |
| 2011/0263815 A1 | 10/2011 | Nash |
| 2012/0082636 A1 | 4/2012 | Walensky et al. |
| 2012/0172311 A1 | 7/2012 | Nash et al. |
| 2012/0190818 A1 | 7/2012 | Nash |
| 2012/0270800 A1 | 10/2012 | Verdine et al. |
| 2013/0005943 A1 | 1/2013 | Arora et al. |
| 2013/0023646 A1 | 1/2013 | Nash et al. |
| 2013/0177979 A1 | 7/2013 | Turkson |
| 2013/0211046 A1 | 8/2013 | Verdine et al. |
| 2014/0005118 A1 | 1/2014 | Verdine et al. |
| 2014/0011979 A1 | 1/2014 | Verdine et al. |
| 2014/0162339 A1 | 6/2014 | Verdine et al. |
| 2014/0235549 A1 | 8/2014 | Moellering et al. |
| 2014/0256912 A1 | 9/2014 | Moellering et al. |
| 2014/0323701 A1 | 10/2014 | Nash et al. |
| 2015/0225471 A1 | 8/2015 | Liang |
| 2015/0239937 A1 | 8/2015 | Verdine et al. |
| 2015/0284437 A1 | 10/2015 | Verdine et al. |
| 2016/0024153 A1 | 1/2016 | Verdine et al. |

FOREIGN PATENT DOCUMENTS

| | | |
|---|---|---|
| WO | WO 96/34878 A1 | 11/1996 |
| WO | WO 97/13537 A1 | 4/1997 |
| WO | WO 97/37705 A1 | 10/1997 |
| WO | WO 99/34850 A1 | 7/1999 |
| WO | WO 00/06187 A2 | 2/2000 |
| WO | WO 02/064790 A2 | 8/2002 |
| WO | WO 03/106491 A2 | 12/2003 |
| WO | WO 03/106491 A3 | 12/2003 |
| WO | WO 2004/041275 A1 | 5/2004 |
| WO | WO 2004/058804 A1 | 7/2004 |
| WO | WO 2005/040202 A2 | 5/2005 |
| WO | WO 2005/040202 A3 | 5/2005 |
| WO | WO 2005/044839 A2 | 5/2005 |
| WO | WO 2005/090388 A1 | 9/2005 |
| WO | WO 2005/118620 A2 | 12/2005 |
| WO | WO 2005/118620 A3 | 12/2005 |
| WO | WO 2005/118634 A2 | 12/2005 |
| WO | WO 2005/118634 A3 | 12/2005 |
| WO | WO 2006/103666 A2 | 10/2006 |
| WO | WO 2007/141533 A2 | 12/2007 |
| WO | WO 2008/061192 A2 | 5/2008 |
| WO | WO 2008/095063 A1 | 8/2008 |
| WO | WO 2008/121767 A2 | 10/2008 |
| WO | WO 2009/042237 A2 | 4/2009 |
| WO | WO 2009/126292 A2 | 10/2009 |
| WO | WO 2010/011313 A2 | 1/2010 |
| WO | WO 2010/034029 A1 | 3/2010 |
| WO | WO 2010/068684 A2 | 6/2010 |
| WO | WO 2011/008260 A2 | 1/2011 |
| WO | WO 2012/040459 A2 | 3/2012 |
| WO | WO 2012/174423 A1 | 12/2012 |
| WO | WO 2014/052647 A2 | 4/2014 |
| WO | WO 2014/055564 A1 | 4/2014 |

OTHER PUBLICATIONS

International Search Report and Written Opinion for PCT/US2009/004260, mailed Oct. 15, 2010.
International Preliminary Report on Patentability for PCT/US2009/004260, mailed Feb. 3, 2011.
Extended European Search Report for EP 12159110.1, mailed Jul. 20, 2012.
Extended European Search Report for EP 12159110.1, mailed Sep. 27, 2012.
International Search Report and Written Opinion for PCT/US2008/058575, mailed Nov. 17, 2008.
International Preliminary Report on Patentability for PCT/US2008/058575, mailed Oct. 8, 2009.
Invitation to Pay Additional Fees for PCT/US2011/052755, mailed Feb. 16, 2012.
International Search Report and Written Opinion for PCT/US2011/052755, mailed Apr. 25, 2012.
International Preliminary Report on Patentability for PCT/US2011/052755, mailed Apr. 4, 2013.
International Search Report and Written Opinion for PCT/US2012/042738, mailed Oct. 18, 2012.
International Preliminary Report on Patentability for PCT/US2012/042738, mailed Jan. 3, 2014.
Invitation to Pay Additional Fees for PCT/US2013/062004, mailed Jan. 2, 2014.
International Search Report and Written Opinion for PCT/US2013/062004, mailed Apr. 23, 2014.
International Preliminary Report on Patentability for PCT/US2013/062004, mailed Apr. 9, 2015.
International Search Report and Written Opinion for PCT/US2013/062929, mailed Jan. 30, 2014.
International Preliminary Report on Patentability for PCT/US2013/062929, mailed Apr. 16, 2015.
International Search Report and Written Opinion for PCT/US2014/025544, mailed Sep. 10, 2014.
International Preliminary Report on Patentability for PCT/US2014/025544, mailed Sep. 24, 2015.
International Search Report and Written Opinion for PCT/US2014/042329, mailed Nov. 24, 2014.
International Preliminary Report on Patentability for PCT/US2014/042329, mailed Dec. 23, 2015.
International Search Report and Written Opinion for PCT/US2014/041338, mailed Nov. 10, 2014.

(56) References Cited

OTHER PUBLICATIONS

International Preliminary Report on Patentability for PCT/US2014/041338, mailed Dec. 17, 2015.
International Preliminary Report on Patentability for PCT/US2014/058680, mailed Apr. 14, 2016.
International Search Report and Written Opinion for PCT/US2014/058680, mailed Apr. 23, 2015.
Extended European Search Report for EP 12800679.8, mailed Oct. 2, 2014.
International Search Report and Written Opinion for PCT/US2012/042719, mailed Nov. 1, 2012.
International Preliminary Report on Patentability for PCT/US2012/042719, mailed Jan. 3, 2014.
International Search Report and Written Opinion for PCT/US2008/052580, mailed May 16, 2008.
[No Author Listed] Designing Custom Peptide. from SIGMA Genosys, p. 1. Accessed Jul. 27, 2012.
[No Author Listed] Brain Tumors. Merck Manuals. Aug. 21, 2014. merckmanuals.com/home/brain_spinal_cord_and_nerve_disorders/tumors_of_the_nervous_system/brain_tumors.html. 9 pages.
[No Author Listed] Overview of Leukemia. Merck Manuals. Aug. 20, 2014. merckmanuals.com/home/blood_disorders/leukemias/overview_of_leukemia.html?qt=Leukemia&alt=sh. 2 pages.
[No Author Listed] Colorectal Cancer. Merck Manuals. Aug. 21, 2014. merckmanuals.com/home/digestive_disorders/tumors_of_the_digestive_system/colorectal_cancer.html. 5 pages.
[No Author Listed] Prostate Cancer. Merck Manuals. Aug. 21, 2014. merckmanuals.com/home/kidney_and_urinary_tract_disorders/cancers_of_the_kidney_and_genitourinary_tract/prostate_cancer.html?qt=prostatecancer&alt=sh. 8 pages.
[No Author Listed] Breast Cancer. Merck Manuals. Aug. 21, 2014. merckmanuals.com/home/womens_health_issues/breast_disorders/breast_cancer.html. 20 pages.
[No Author Listed] Bladder Cancer. Merck Manuals. Aug. 21, 2014. merckmanuals.com/home/kidney_and_urinary_tract_disorders/cancers_of_the_kidney_and_genitourinary_tract/bladder_cancer.html. 2 pages.
[No Author Listed] Wikipedia Entry, "Willgerodt Rearrangement." Oct. 7, 2012. http://en.wikipedia.org/wiki/Willgerodt_rearrangement. [Last accessed Feb. 12, 2013].
Adhikary et al., Transcriptional regulation and transformation by Myc proteins. Nat Rev Mol Cell Biol. Aug. 2005;6(8):635-45.
Agola et al., Rab GTPases as regulators of endocytosis, targets of disease and therapeutic opportunities. Clin Genet. Oct. 2011; 80(4): 305-318.
Altschul et al., Basic local alignment search tool. J Mol Biol. Oct. 5, 1990;215(3):403-10.
Aman et al., cDNA cloning and characterization of the human interleukin 13 receptor alpha chain. J Biol Chem. Nov. 15, 1996;271(46):29265-70.
Andrews et al., Forming Stable Helical Peptides Using Natural and Artificial Amino Acids. Tetrahedron. 1999;55:11711-43.
Andrews et al., Kinetic analysis of the interleukin-13 receptor complex. J Biol Chem. Nov. 29, 2002;277(48):46073-8. Epub Sep. 26, 2002.
Armstrong et al., X=Y-ZH Systems as potential 1,3-dipoles. 5. Intramolecular cycloadditions of imines of a-amino acid esters. Tetrahedron. 1985;41(17):3547-58.
Attisano et al., TGFbeta and Wnt pathway cross-talk. Cancer Metastasis Rev. Jan.-Jun. 2004;23(1-2):53-61.
Babine et al., Molecular Recognition of Proteinminus signLigand Complexes: Applications to Drug Design. Chem Rev. Aug. 5, 1997;97(5):1359-1472.
Balthaser et al., Remodelling of the natural product fumagillol employing a reaction discovery approach. Nat Chem. Dec. 2011;3(12):969-73.
Banerjee et al., Structure of a DNA glycosylase searching for lesions. Science. Feb. 24, 2006;311(5764):1153-7.

Banerjee et al., Structure of a repair enzyme interrogating undamaged DNA elucidates recognition of damaged DNA. Nature. Mar. 31, 2005;434(7033):612-8.
Bang et al., Total chemical synthesis of crambin. J Am Chem Soc. Feb. 11, 2004;126(5):1377-83.
Barandon et al., Reduction of infarct size and prevention of cardiac rupture in transgenic mice overexpressing FrzA. Circulation. Nov. 4, 2003;108(18):2282-9. Epub Oct. 27, 2003.
Barker et al., Mining the Wnt pathway for cancer therapeutics. Nat Rev Drug Discov. Dec. 2006;5(12):997-1014.
Beloken et al., Chiral Complexes of Ni(II), Cu(II) and Cu(I) as Reagents, Catalysts and Receptors for Asymmetric Synthesis and Chiral Recognition of Amino Acids. Pure & Appl Chem. 1992;64(12):1917-24.
Belokon et al., Improved procedures for the synthesis of (S)-2-[N-(N'-benzyl-prolyl)amino]benzophenone (BPB) and Ni(II) complexes of Schiff's bases derived from BPB and amino acids. Tetrahedron: Asymmetry. 1998;9:4249-52.
Bennett et al., Regulation of osteoblastogenesis and bone mass by Wntl0b. Proc Natl Acad Sci U S A. Mar. 1, 2005;102(9):3324-9. Epub Feb. 22, 2005.
Berendsen et al., A glimpse of the Holy Grail? Science. Oct. 23, 1998;282(5389):642-3.
Berge et al., Pharmaceutical salts. J Pharm Sci. Jan. 1977;66(1):1-19.
Bernal et al., Reactivation of the p53 tumor suppressor pathway by a stapled p53 peptide. J Am Chem Soc. Mar. 7, 2007;129(9):2456-7. Epub Feb. 7, 2007.
Biagini et al., Cross-metathesis of Unsaturated α-amino Acid Derivatives. J Chem Soc Perkin Trans. 1998;1:2485-99.
Bierzynski et al., A salt bridge stabilizes the helix formed by isolated C-peptide of Rnase A. Proc Natl Acad Sci U S A. Apr. 1982;79(8):2470-4.
Blackwell et al., Highly Efficient Synthesis of Covalently Cross-Linked Peptide Helices by Ring-Closing Metathesis. Angew Chem Int Ed. 1998;37(23):3281-84.
Blackwell et al., Ring-closing metathesis of olefinic peptides: design, synthesis, and structural characterization of macrocyclic helical peptides. J Org Chem. Aug. 10, 2001;66(16):5291-302.
Blangetti et al., Suzuki-miyaura cross-coupling in acylation reactions, scope and recent developments.Molecules. Jan. 17, 2013;18(1):1188-213. doi:10.3390/molecules18011188.
Blundell et al., Atomic positions in rhombohedral 2-zinc insulin crystals. Nature. Jun. 25, 1971;231(5304):506-11.
Bode et al., Chemoselective amide ligations by decarboxylative condensations of N-alkylhydroxylamines and alpha-ketoacids. Angew Chem Int Ed Engl. Feb. 13, 2006;45(8):1248-52.
Boyden et al., High bone density due to a mutation in LDL-receptor-related protein 5. N Engl J Med. May 16, 2002;346(20):1513-21.
Bracken et al., Synthesis and Nuclear Magnetic Resonance Structure Determination of an α-Helical, Bicyclic, Lactam-Bridged Hexapeptide. J Am Chem Soc. 1994;116:6431-32.
Bradley et al., Limits of cooperativity in a structurally modular protein: response of the Notch ankyrin domain to analogous alanine substitutions in each repeat. J Mol Biol. Nov. 22, 2002;324(2):373-86.
Brandt et al., Dimeric fragment of the insulin receptor alpha-subunit binds insulin with full holoreceptor affinity. J Biol Chem. Apr. 13, 2001;276(15):12378-84. Epub Jan. 12, 2001.
Brubaker et al., Solution structure of the interacting domains of the Mad-Sin3 complex: implications for recruitment of a chromatin-modifying complex. Cell. Nov. 10, 2000;103(4):655-65.
Brusselle et al., Allergen-induced airway inflammation and bronchial responsiveness in wild-type and interleukin-4-deficient mice. Am J Respir Cell Mol Biol. Mar. 1995;12(3):254-9.
Burger et al., Synthesis of a-(trifluoromethyl)-substituted a-amino acids. Part 7. An efficient synthesis for a-trifluoromethyl-substituted w-carboxy a-amino acids. Chemiker-Zeitung. 1990;114(3):101-04. German.
Caricasole et al., The Wnt pathway, cell-cycle activation and beta-amyloid: novel therapeutic strategies in Alzheimer's disease? Trends Pharmacol Sci. May 2003;24(5):233-8.

(56) References Cited

OTHER PUBLICATIONS

Carillo et al., The Multiple Sequence Alignment Problem in Biology. SIAM J Applied Math. 1988;48:1073-82.
Carlson et al., Specificity landscapes of DNA binding molecules elucidate biological function. Proc Natl Acad Sci U S A. Mar. 9, 2010;107(10):4544-9. doi: 10.1073/pnas.0914023107. Epub Feb. 22, 2010.
Chen et al., Determination of the helix and beta form of proteins in aqueous solution by circular dichroism. Biochemistry. Jul. 30, 1974;13(16):3350-9.
Chen et al., Small molecule-mediated disruption of Wnt-dependent signaling in tissue regeneration and cancer. Nat Chem Biol. Feb. 2009;5(2):100-7. Epub Jan. 4, 2009.
Cheng et al., Emerging role of RAB GTPases in cancer and human disease. Cancer Res. Apr. 1, 2005;65(7):2516-9.
Cheng et al., The RAB25 small GTPase determines aggressiveness of ovarian and breast cancers. Nat Med. Nov. 2004;10(11):1251-6. Epub Oct. 24, 2004.
Cheon et al., beta-Catenin stabilization dysregulates mesenchymal cell proliferation, motility, and invasiveness and causes aggressive fibromatosis and hyperplastic cutaneous wounds. Proc Natl Acad Sci U S A. May 14, 2002;99(10):6973-8. Epub Apr. 30, 2002.
Chia et al., Emerging roles for Rab family GTPases in human cancer. Biochim Biophys Acta. Apr. 2009;1795(2):110-6.
Chiaramonte et al., Studies of murine schistosomiasis reveal interleukin-13 blockade as a treatment for established and progressive liver fibrosis. Hepatology. Aug. 2001;34(2):273-82.
Christodoulides et al., WNT10B mutations in human obesity. Diabetologia. Apr. 2006;49(4):678-84. Epub Feb. 14, 2006.
Clark et al., Supramolecular Design by Covalent Capture. Design of a Peptide Cylinder via Hydrogen-Bond-Promoted Intermolecular Olefin Metathesis. J Am Chem Soc. 1995;117:12364-65.
Clevers, Wnt/beta-catenin signaling in development and disease. Cell. Nov. 3, 2006;127(3):469-80.
Cohn et al., Cutting Edge: IL-4-independent induction of airway hyperresponsiveness by Th2, but not Th1, cells. J Immunol. Oct. 15, 1998;161(8):3813-6.
Cole et al., Transcription-independent functions of MYC: regulation of translation and DNA replication. Nat Rev Mol Cell Biol. Oct. 2008;9(10):810-5. Epub Aug. 13, 2008.
Cong et al., A protein knockdown strategy to study the function of beta-catenin in tumorigenesis. BMC Mol Biol. Sep. 29, 2003;4:10.
Cossu et al., Wnt signaling and the activation of myogenesis in mammals. EMBO J. Dec. 15, 1999;18(24):6867-72.
Cox et al., Insulin receptor expression by human prostate cancers. Prostate. Jan. 1, 2009;69(1):33-40. doi: 10.1002/pros.20852.
Cusack et al., 2,4,6-Tri-isopropylbenzenesulphonyl Hydrazide: A Convenient Source of Di-imide. Tetrahedron. 1976;32:2157-62.
David et al., Expressed protein ligation. Method and applications. Eur J Biochem. Feb. 2004;271(4):663-77.
Dawson et al., Synthesis of proteins by native chemical ligation. Science. Nov. 4, 1994;266(5186):776-9.
De Guzman et al., Structural basis for cooperative transcription factor binding to the CBP coactivator. J Mol Biol. Feb. 3, 2006;355(5):1005-13. Epub Oct. 5, 2005.
De Meyts et al., Insulin interactions with its receptors: experimental evidence for negative cooperativity. Biochem Biophys Res Commun Nov. 1, 1973;55(1):154-61.
De Meyts, The structural basis of insulin and insulin-like growth factor-I receptor binding and negative co-operativity, and its relevance to mitogenic versus metabolic signalling. Diabetologia. Sep. 1994;37 Suppl 2:S135-48.
Debinski et al., Retargeting interleukin 13 for radioimmunodetection and radioimmunotherapy of human high-grade gliomas. Clin Cancer Res. Oct. 1999;5(10 Suppl):3143s-3147s.
Denmark et al., Cyclopropanation with Diazomethane and Bis(oxazoline)palladium(II) Complexes. J Org Chem. May 16, 1997;62(10):3375-3389.
Devereux et al., A comprehensive set of sequence analysis programs for the VAX. Nucleic Acids Res. Jan. 11, 1984;12(1 Pt 1):387-95.
Doron et al., Probiotics: their role in the treatment and prevention of disease. Expert Rev Anti Infect Ther. 2006;4:261-75.
Duronio, Insulin receptor is phosphorylated in response to treatment of HepG2 cells with insulin-like growth factor I. Biochem J. Aug. 15, 1990;270(1):27-32.
Eisenmesser et al., Solution structure of interleukin-13 and insights into receptor engagement. J Mol Biol. Jun. 29, 2001;310(1):231-41.
Ellis et al., Design, synthesis, and evaluation of a new generation of modular nucleophilic glycine equivalents for the efficient synthesis of sterically constrained alpha-amino acids. J Org Chem. Oct. 27, 2006;71(22):8572-8.
Erlanson et al., The leucine zipper domain controls the orientation of AP-1 in the NFAT.AP-1.DNA complex. Chem Biol. Dec. 1996;3(12):981-91.
Evans et al., The Rise of Azide—Alkyne 1,3-Dipolar 'Click' Cycloaddition and its Application to Polymer Science and Surface Modification. Australian Journal of Chemistry. 2007;60:384-95.
Favrin et al., Two-state folding over a weak free-energy barrier. Biophys J. Sep. 2003;85(3):1457-65.
Fischbach et al., Specific biochemical inactivation of oncogenic Ras proteins by nucleoside diphosphate kinase. Cancer Res. Jul. 15, 2003;63(14):4089-94.
Fischer et al., The HIV-1 Rev activation domain is a nuclear export signal that accesses an export pathway used by specific cellular RNAs. Cell. Aug. 11, 1995;82(3):475-83.
Fisher et al., Myc/Max and other helix-loop-helix/leucine zipper proteins bend DNA toward the minor groove. Proc Natl Acad Sci U S A. Dec. 15, 1992;89(24):11779-83.
Formaggio et al., Inversion of 3(10)-helix screw sense in a (D-alpha Me)Leu homo-tetrapeptide induced by a guest D-(alpha Me)Val residue. J Pept Sci. Nov.-Dec. 1995;1(6):396-402.
Friedman-Einat et al., Target gene identification: target specific transcriptional activation by three murine homeodomain/VP16 hybrid proteins in Saccharomyces cerevisiae. J Exp Zool. Feb. 15, 1996;274(3):145-56.
Fromme et al., Structural basis for removal of adenine mispaired with 8-oxoguanine by MutY adenine DNA glycosylase. Nature. Feb. 12, 2004;427(6975):652-6.
Fuchs et al., Socializing with the neighbors: stem cells and their niche. Cell. Mar. 19, 2004;116(6):769-78.
Furstner et al., Alkyne Metathesis: Development of a Novel Molybdenum-Based Catalyst System and Its Application to the Total Synthesis of Epothilone A and C. Chem Euro J. 2001;7(24):5299-5317.
Furstner et al., Mo[N(t-Bu)(AR)]3 Complexes As Catalyst Precursors: In Situ Activation and Application to Metathesis Reactions of Alkynes and Diynes. J Am Chem Soc. 1999;121:9453-54.
Furstner et al., Nozaki—Hiyama—Kishi Reactions Catalytic in Chromium. J Am Chem Soc. 1996:118:12349-57.
Fustero et al., Asymmetric synthesis of new beta,beta-difluorinated cyclic quaternary alpha-amino acid derivatives. Org Lett. Aug. 31, 2006;8(18):4129-32.
Gallivan et al., A neutral, water-soluble olefin metathesis catalyst based on an N-heterocyclic carbene ligand. Tetrahedron Letters. 2005;46:2577-80.
Gante, Peptidomimetics—Tailored Enzyme Inhibitors. J Angew Chem Int Ed Engl. 1994;33:1699-1720.
Gat et al., De Novo hair follicle morphogenesis and hair tumors in mice expressing a truncated beta-catenin in skin. Cell. Nov. 25, 1998;95(5):605-14.
Gavathiotis et al., BAX activation is initiated at a novel interaction site. Nature. Oct. 23, 2008;455(7216):1076-81.
Gentle et al., Direct production of proteins with N-terminal cysteine for site-specific conjugation. Bioconjug Chem. May-Jun. 2004;15(3):658-63.
Gerber-Lemaire et al., Glycosylation pathways as drug targets for cancer: glycosidase inhibitors. Mini Rev Med Chem. Sep. 2006;6(9):1043-52.
Giannis et al., Peptidomimetics for Receptor Ligands—Discovery, Development, and Medical Perspectives. Angew Chem Int Ed Engl. 1993;32:1244-67.
Gong et al., LDL receptor-related protein 5 (LRP5) affects bone accrual and eye development. Cell. Nov. 16, 2001;107(4):513-23.

(56) References Cited

OTHER PUBLICATIONS

Goodson et al., Potential Growth Antagonists. I. Hydantoins and Disubstituted Glycines. J Org Chem. 1960;25:1920-24.

Görlich et al., Transport between the cell nucleus and the cytoplasm. Annu Rev Cell Dev Biol. 1999;15:607-60.

Goun et al., Molecular transporters: synthesis of oligoguanidinium transporters and their application to drug delivery and real-time imaging. Chembiochem. Oct. 2006;7(10):1497-515.

Greenfield et al., Computed circular dichroism spectra for the evaluation of protein conformation. Biochemistry. Oct. 1969;8(10):4108-16.

Greenlee et al., A General Synthesis of α-vinyl-α-amino acids. Tetrahedron Letters. 1978;42:3999-4002.

Grubbs et al., Ring-Closing Metathesis and Related Processes in Organic Synthesis. Acc Chem Res. 1995;28:446-52.

Grünig et al., Requirement for IL-13 independently of IL-4 in experimental asthma. Science. Dec. 18, 1998;282(5397):2261-3.

Guinn et al., Synthesis and characterization of polyamides containing unnatural amino acids. Biopolymers. May 1995;35(5):503-12.

Gupta et al., Long-term effects of tumor necrosis factor-alpha treatment on insulin signaling pathway in HepG2 cells and HepG2 cells overexpressing constitutively active Akt/PKB. J Cell Biochem. Feb. 15, 2007;100(3):593-607.

Harper et al., Efficacy of a bivalent L1 virus-like particle vaccine in prevention of infection with human papillomavirus types 16 and 18 in young women: a randomized controlled trial. Lancet. Nov. 13-19, 2004;364(9447):1757-65.

Harris et al., Synthesis of proline-modified analogues of the neuroprotective agent glycyl-l-prolyl-glutamic acid (GPE). Tetrahedron. 2005;61:10018-35.

Hartmann et al., Dual roles of Wnt signaling during chondrogenesis in the chicken limb. Development. Jul. 2000;127(14):3141-59.

Hartmann, A Wnt canon orchestrating osteoblastogenesis. Trends Cell Biol. Mar. 2006;16(3):151-8. Epub Feb. 7, 2006.

Hellman et al., Electrophoretic mobility shift assay (EMSA) for detecting protein-nucleic acid interactions. Nat Protoc. 2007;2(8):1849-61.

Henchey et al., Contemporary strategies for the stabilization of peptides in the α-helical conformation. Curr Opin Chem Biol. 2008;12:692-97.

Hipfner et al., Connecting proliferation and apoptosis in development and disease. Nat Rev Mol Cell Biol. Oct. 2004;5(10):805-15.

Hoang et al., Dickkopf 3 inhibits invasion and motility of Saos-2 osteosarcoma cells by modulating the Wnt-beta-catenin pathway. Cancer Res. Apr. 15, 2004;64(8):2734-9.

Holford et al., Adding 'splice' to protein engineering. Structure. Aug. 15, 1998;6(8):951-6.

Huang et al., How insulin binds: the B-chain alpha-helix contacts the L1 beta-helix of the insulin receptor. J Mol Biol. Aug. 6, 2004;341(2):529-50.

Huang et al., Tankyrase inhibition stabilizes axin and antagonizes Wnt signalling. Nature. Oct. 1, 2009;461(7264):614-20. Epub Sep. 16, 2009.

Jackson et al., General Approach to the Synthesis of Short α-Helical Peptides. J Am Chem Soc. 1991;113:9391-92.

Jamieson et al., Granulocyte-macrophage progenitors as candidate leukemic stem cells in blast-crisis CML. N Engl J Med. Aug. 12, 2004;351(7):657-67.

Jensen et al., Activation of the insulin receptor (IR) by insulin and a synthetic peptide has different effects on gene expression in IR-transfected L6 myoblasts. Biochem J. Jun. 15, 2008;412(3):435-45. doi: 10.1042/BJ20080279.

Jordan et al., Wnt4 overexpression disrupts normal testicular vasculature and inhibits testosterone synthesis by repressing steroidogenic factor 1/beta-catenin synergy. Proc Natl Acad Sci U S A. Sep. 16, 2003;100(19):10866-71. Epub Aug. 29, 2003.

Junutula et al., Molecular characterization of Rab11 interactions with members of the family of Rab11-interacting proteins. J Biol Chem. Aug. 6, 2004;279(32):33430-7. Epub Jun. 1, 2004.

Karle et al., Structural characteristics of alpha-helical peptide molecules containing Aib residues. Biochemistry. Jul 24, 1990;29(29):6747-56.

Karwoski et al., Lysinonorleucine cross-link formation in alpha amino heptenoic acid-substituted peptide derivatives. Biopolymers. 1978;17(5):1119-27.

Katoh et al., Cross-talk of WNT and FGF signaling pathways at GSK3beta to regulate beta-catenin and SNAIL signaling cascades. Cancer Biol Ther. Sep. 2006;5(9):1059-64. Epub Sep. 4, 2006.

Katsu et al., The human frizzled-3 (FZD3) gene on chromosome 8p21, a receptor gene for Wnt ligands, is associated with the susceptibility to schizophrenia. Neurosci Lett. Dec. 15, 2003;353(1):53-6.

Kaul et al., Stereochemical control of peptide folding. Bioorg Med Chem. Jan. 1999;7(1):105-17.

Kawamoto, Targeting the BCL9/B9L binding interaction with beta-catenin as a potential anticancer strategy. PhD Thesis. Jun. 3, 2010. Available at http://deepblue.lib.umich.edu/handle/2027.42/75846 last accessed Apr. 9, 2012. Abstract only. 2 pages.

Kazmaier, Sythesis of Quaternary Amino Acids Containing β, γ-as well as γ,δ-Unsaturated Side Chains via Chelate-Enolate Claisen Rearrangement. Tetrahedron Letters. 1996;37(30):5351-4.

Kelly-Welch et al., Interleukin-4 and Interleukin-13 Signaling Connections Maps. Science. 2003;300:1527-28.

Kim et al., Introduction of all-hydrocarbon i,i+3 staples into alpha-helices via ring-closing olefin metathesis. Org Lett. Jul. 2, 2010;12(13):3046-9. doi: 10.1021/ol1010449.

Kim et al., Stereochemical effects of all-hydrocarbon tethers in i,i+4 stapled peptides. Bioorg Med Chem Lett. May 1, 2009;19(9):2533-6. Epub Mar. 13, 2009.

Kim et al., Synthesis of all-hydrocarbon stapled α-helical peptides by ring-closing olefin metathesis. Nat Protoc. Jun. 2011;6(6):761-71. doi: 10.1038/nprot.2011.324. Epub May 12, 2011.

Kimmerlin et al., '100 years of peptide synthesis': ligation methods for peptide and protein synthesis with applications to beta-peptide assemblies. J Pept Res. Feb. 2005;65(2):229-60.

Kinage et al., Highly regio-selective synthesis of beta-amino alcohol by reaction with aniline and propylene carbonate in self solvent systems over large pore zeolite catalyst. Green and Sustainable Chem. Aug. 2011;1: 76-84.

Kinzler et al., Identification of FAP locus genes from chromosome 5q21. Science. Aug. 9, 1991;253(5020):661-5.

Kinzler et al., Lessons from hereditary colorectal cancer. Cell. Oct. 18, 1996;87(2):159-70.

Knackmuss et al., Specific inhibition of interleukin-13 activity by a recombinant human single-chain immunoglobulin domain directed against the IL-13 receptor alphal chain. Biol Chem. Mar. 2007;388(3):325-30.

Kohler et al., DNA specificity enhanced by sequential binding of protein monomers. Proc Natl Acad Sci U S A. Oct. 12, 1999;96(21):11735-9.

Kolb et al., Click Chemistry: Diverse Chemical Function from a Few Good Reactions. Angew Chem Int Ed Engl. Jun. 1, 2001;40(11):2004-2021.

Kondo et al., Frizzled 4 gene (FZD4) mutations in patients with familial exudative vitreoretinopathy with variable expressivity. Br J Ophthalmol. Oct. 2003;87(10):1291-5.

Korcsmáros et al., Uniformly curated signaling pathways reveal tissue-specific cross-talks and support drug target discovery. Bioinformatics. Aug. 15, 2010;26(16):2042-50. Epub Jun. 11, 2010.

Korinek et al., Depletion of epithelial stem-cell compartments in the small intestine of mice lacking Tcf-4. Nat Genet. Aug. 1998;19(4):379-83.

Kotha et al., Modification of constrained peptides by ring-closing metathesis reaction. Bioorg Med Chem Lett. Jun. 4, 2001;11(11):1421-3.

Kouzarides, Acetylation: a regulatory modification to rival phosphorylation? EMBO J. Mar. 15, 2000;19(6):1176-9.

Kozlovsky et al., GSK-3 and the neurodevelopmental hypothesis of schizophrenia. Eur Neuropsychopharmacol. Feb. 2002;12(1):13-25.

(56) References Cited

OTHER PUBLICATIONS

Kristensen et al., Expression and characterization of a 70-kDa fragment of the insulin receptor that binds insulin. Minimizing ligand binding domain of the insulin receptor. J Biol Chem. Jul. 10, 1998;273(28):17780-6.

Kristensen et al., Functional reconstitution of insulin receptor binding site from non-binding receptor fragments. J Biol Chem. May 24, 2002;277(21):18340-5. Epub Mar. 18, 2002.

Kurose et al., Cross-linking of a B25 azidophenylalanine insulin derivative to the carboxyl-terminal region of the alpha-subunit of the insulin receptor. Identification of a new insulin-binding domain in the insulin receptor. J Biol Chem. Nov. 18, 1994;269(46):29190-7.

Kussie et al., Structure of the MDM2 oncoprotein bound to the p53 tumor suppressor transactivation domain. Science. Nov. 8, 1996;274(5289):948-53.

Kutchukian et al., All-atom model for stabilization of alpha-helical structure in peptides by hydrocarbon staples. J Am Chem Soc. Apr. 8, 2009;131(13):4622-7.

Lacombe et al., Reduction of Olefins on Solid Support Using Diimide. Tetranderon Lett. 1998;39:6785-86.

Lammi et al., Mutations in AXIN2 cause familial tooth agenesis and predispose to colorectal cancer. Am J Hum Genet. May 2004;74(5):1043-50. Epub Mar. 23, 2004.

Laporte et al., Molecular and structural basis of cytokine receptor pleiotropy in the interleukin-4/13 system. Cell. Jan. 25, 2008;132(2):259-72.

Le Geuzennec et al., Molecular characterization of Sin3 PAH-domain interactor specificity and identification of PAH partners. Nucleic Acids Res. 2006;34(14):3929-37. Epub Aug. 12, 2006.

Le Geuzennec et al., Molecular determinants of the interaction of Mad with the PAH2 domain of mSin3. J Biol Chem. Jun. 11, 2004;279(24):25823-9. Epub Mar. 26, 2004.

Leduc et al., Helix-stabilized cyclic peptides as selective inhibitors of steroid receptor—coactivator interactions. Proc Natl Acad Sci USA. 2003;100(20):11273-78.

Liang et al., Wnt5a inhibits B cell proliferation and functions as a tumor suppressor in hematopoietic tissue. Cancer Cell. Nov. 2003;4(5):349-60.

Lindsay et al., Rab coupling protein (RCP), a novel Rab4 and Rab11 effector protein. J Biol Chem. Apr. 5, 2002;277(14):12190-9. Epub Jan. 10, 2002.

Liskamp, Conformationally restricted amino acids and dipeptides, (non)peptidomimetics and secondary structure mimetics. Red Travl Chim Pays-Bas. 1994;113:1-19.

Little et al., A Mutation in the LDL Receptor-Related Protein 5 Gene Results in the Autosomal Dominant High-Bone-Mass Trait. Am J Hum Genet. 2002;70:11-19.

Liu et al., Chemical Ligation Approach to Form a Peptide Bond between Unprotected Peptide Segments. Concept and Model Study. J Am Chem Soc. 1994;116(10):4149-53.

Liu et al., Targeted degradation of beta-catenin by chimeric F-box fusion proteins. Biochem Biophys Res Commun Jan. 23, 2004;313(4):1023-9.

Lo et al., Phosphorylation by the beta-catenin/MAPK complex promotes 14-3-3-mediated nuclear export of TCF/POP-1 in signal-responsive cells in C. elegans. Cell. Apr. 2, 2004;117(1):95-106.

Logan et al., The Wnt signaling pathway in development and disease. Annu Rev Cell Dev Biol. 2004;20:781-810.

Lomar et al., Synthese symmetrischerf ketone unter verwendung von 2-Phenyl-2-oxazolin-5-on. Chemische Berichte. 1980;113(12):3706-15.

Losey et al., Crystal structure of *Staphylococcus aureus* tRNA adenosine deaminase TadA in complex with RNA. Nat Struct Mol Biol. Feb. 2006;13(2):153-9. Epub Jan. 15, 2006.

Lou et al., The first three domains of the insulin receptor differ structurally from the insulin-like growth factor 1 receptor in the regions governing ligand specificity. Proc Natl Acad Sci U S A. Aug. 15, 2006;103(33):12429-34. Epub Aug. 7, 2006.

Loughlin et al., Functional variants within the secreted frizzled-related protein 3 gene are associated with hip osteoarthritis in females. Proc Natl Acad Sci U S A. Jun. 29, 2004;101(26):9757-62. Epub Jun. 21, 2004.

Lu et al., Both Pbx1 and E2A-Pbx1 bind the DNA motif ATCAATCAA cooperatively with the products of multiple murine Hox genes, some of which are themselves oncogenes. Mol Cell Biol. Jul. 1995;15(7):3786-95.

Lu et al., Structural determinants within Pbx1 that mediate cooperative DNA binding with pentapeptide-containing Hox proteins: proposal for a model of a Pbx1-Hox-DNA complex. Mol Cell Biol. Apr. 1996;16(4):1632-40.

Luo et al., Wnt signaling and human diseases: what are the therapeutic implications? Lab Invest. Feb. 2007;87(2):97-103. Epub Jan. 8, 2007.

Luscher et al., The basic region/helix-loop-helix/leucine zipper domain of Myc proto-oncoproteins: function and regulation. Oncogene. May 13, 1999;18(19):2955-66.

Luu et al, Wnt/beta-catenin signaling pathway as a novel cancer drug target. Curr Cancer Drug Targets. Dec. 2004;4(8):653-71.

MacMillan, Evolving strategies for protein synthesis converge on native chemical ligation. Angew Chem Int Ed Engl. Nov. 27, 2006;45(46):7668-72.

Marshall et al., Back to the future: ribonuclease A. Biopolymers. 2008;90(3):259-77.

McKern et al., Structure of the insulin receptor ectodomain reveals a folded-over conformation. Nature. Sep. 14, 2006;443(7108):218-21. Epub Sep. 6, 2006.

McNamara et al., Peptides constrained by an aliphatic linkage between two C(alpha) sites: design, synthesis, and unexpected conformational properties of an i,(i + 4)-linked peptide. J Org Chem. Jun. 29, 2001;66(13):4585-94.

Mellegaardwaetzig et al., Allylic amination via decarboxylative c-n bond formation Synlett. 2005;18:2759-2762.

Menting et al., A thermodynamic study of ligand binding to the first three domains of the human insulin receptor: relationship between the receptor alpha-chain C-terminal peptide and the site 1 insulin mimetic peptides. Biochemistry. Jun. 16, 2009;48(23):5492-500. doi: 10.1021/bi900261q.

Meyers et al., Formation of mutually exclusive Rab11 complexes with members of the family of Rab11-interacting proteins regulates Rab11 endocytic targeting and function. J Biol Chem. Dec. 13, 2002;277(50):49003-10. Epub Oct. 9, 2002.

Miller et al., Application of Ring-Closing Metathesis to the Synthesis of Rigidified Amino Acids and Peptides. J Am Chem Soc. 1996;118(40):9606-9614.

Miller et al., Synthesis of Conformationally Restricted Amino Acids and Peptides Employing Olefin Metathesis. J Am Chem Soc. 1995;117(21):5855-5856.

Miloux et al., Cloning of the human IL-13R alphal chain and reconstitution with the IL4R alpha of a functional IL-4/IL-13 receptor complex. FEBS Lett. Jan. 20, 1997;401(2-3):163-6.

Miyaoka et al., Increased expression of Wnt-1 in schizophrenic brains. Schizophr Res. Jul. 27, 1999;38(1):1-6.

Moellering et al., Computational modeling and molecular optimization of stabilized alpha-helical peptides targeting NOTCH-CSL transcriptional complexes. European Journal of Cancer Supplements Nov. 2010; 8(7):30. DOI: 10.1016/S1359-6349(10)71774-2. Abstract 69.

Moellering et al., Direct inhibition of the NOTCH transcription factor complex. Nature. Nov. 12, 2009;462(7270):182-8.

Moon et al., WNT and beta-catenin signalling: diseases and therapies. Nat Rev Genet. Sep. 2004;5(9):689-99.

Morin, beta-catenin signaling and cancer. Bioessays. Dec. 1999;21(12):1021-30.

Moses et al., The growing applications of click chemistry. Chem Soc Rev. Aug. 2007;36(8):1249-62.

Moy et al., Solution structure of human IL-13 and implication for receptor binding. J Mol Biol. Jun. 29, 2001;310(1):219-30.

Mudher et al., Alzheimer's disease-do tauists and baptists finally shake hands? Trends Neurosci. Jan. 2002;25(1):22-6.

(56) References Cited

OTHER PUBLICATIONS

Muir et al., Expressed protein ligation: a general method for protein engineering. Proc Natl Acad Sci U S A. Jun. 9, 1998;95(12):6705-10.
Muir, Semisynthesis of proteins by expressed protein ligation. Annu Rev Biochem. 2003;72:249-89. Epub Feb. 27, 2003.
Mynarcik et al., Alanine-scanning mutagenesis of a C-terminal ligand binding domain of the insulin receptor alpha subunit. J Biol Chem. Feb. 2, 1996;271(5):2439-42.
Mynarcik et al., Identification of common ligand binding determinants of the insulin and insulin-like growth factor 1 receptors. Insights into mechanisms of ligand binding. J Biol Chem. Jul. 25, 1997;272(30):18650-5.
Myung et al., The ubiquitin-proteasome pathway and proteasome inhibitors. Med Res Rev. Jul. 2001;21(4):245-73.
Nair et al., X-ray structures of Myc-Max and Mad-Max recognizing DNA. Molecular bases of regulation by proto-oncogenic transcription factors. Cell. Jan. 24, 2003;112(2):193-205.
Nakashima et al., Cross-talk between Wnt and bone morphogenetic protein 2 (BMP-2) signaling in differentiation pathway of C2C12 myoblasts. J Biol Chem. Nov. 11, 2005;280(45):37660-8. Epub Sep. 2, 2005.
Ngo et al., Computational complexity, protein structure prediction, and the levinthal paradox. In: The Protein Folding Problem and Tertiary Structure Prediction. K. Mem, Jr., et al. Eds. 1994:433-506.
Niemann et al., Homozygous WNT3 mutation causes tetra-amelia in a large consanguineous family. Am J Hum Genet. Mar. 2004;74(3):558-63. Epub Feb. 5, 2004.
Nilsson et al., Staudinger ligation: a peptide from a thioester and azide. Org Lett. Jun. 29, 2000;2(13):1939-41.
Nishisho et al., Mutations of chromosome 5q21 genes in FAP and colorectal cancer patients. Science. Aug. 9, 1991;253(5020):665-9.
Node et al., Hard Acid and Soft Nucleophile Systems. 3. Dealkylation of Esters with Aluminum Halide-Thiol and Aluminum Halide-Sulfide Stustems. J Org Chem. 1981;46:1991-93.
Okamura et al., Redundant regulation of T cell differentiation and TCRalpha gene expression by the transcription factors LEF-1 and TCF-1. Immunity. Jan. 1998;8(1):11-20.
Olson et al., Sizing up the heart: development redux in disease. Genes Dev. Aug. 15, 2003;17(16):1937-56. Epub Jul. 31, 2003.
Pakotiprapha et al., Crystal structure of Bacillus stearothermophilus UvrA provides insight into ATP-modulated dimerization, UvrB interaction, and DNA binding. Mol Cell. Jan. 18, 2008;29(1):122-33. Epub Dec. 27, 2007.
Palchaudhuri et al., Differentiation induction in acute myeloid leukemia using site-specific DNA-targeting. 55th ASH Annual Meeting and Exposition. Dec. 9, 2013. Accessed at https://ash.confex.com/ash/2013/webprogram/Paper60843.html.
Parrish et al., Perspectives on alkyl carbonates in organic synthesis. Tetrahedron, 2000; 56(42): 8207-8237.
Pellois et al., Semisynthetic proteins in mechanistic studies: using chemistry to go where nature can't. Curr Opin Chem Biol. Oct. 2006;10(5):487-91. Epub Aug. 28, 2006.
Perantoni, Renal development: perspectives on a Wnt-dependent process. Semin Cell Dev Biol. Aug. 2003;14(4):201-8.
Phelan et al., A General Method for Constraining Short Peptides to an α-Helical Conformation. J Am Chem Soc. 1997;119(3):455-60.
Picksley et al., Immunochemical analysis of the interaction of p53 with MDM2;—fine mapping of the MDM2 binding site on p53 using synthetic peptides. Oncogene. Sep. 1994;9(9):2523-9.
Pillutla et al., Peptides identify the critical hotspots involved in the biological activation of the insulin receptor. J Biol Chem. Jun. 21, 2002;277(25):22590-4. Epub Apr. 18, 2002.
Polakis, The oncogenic activation of beta-catenin. Curr Opin Genet Dev. Feb. 1999;9(1):15-21.
Qiu et al., Convenient, Large-Scale Asymmetric Synthesis of Enantiomerically Pure trans-Cinnamylglycine and -α-Alanine. Tetrahedron. 2000;56:2577-82.
Rawlinson et al., CRM1-mediated nuclear export of dengue virus RNA polymerase NS5 modulates interleukin-8 induction and virus production. J Biol Chem. Jun. 5, 2009;284(23):15589-97. Epub Mar. 18, 2009.
Reya et al., Wnt signalling in stem cells and cancer. Nature. Apr. 14, 2005;434(7035):843-50.
Rich et al., Synthesis of the cytostatic cyclic tetrapeptide, chlamydocin. Tetranderon Letts. 1983;24(48):5305-08.
Robert, A hierarchical "nesting" approach to describe the stability of alpha helices with side-chain interactions. Biopolymers. 1990;30(3-4):335-47.
Robitaille et al., Mutant frizzled-4 disrupts retinal angiogenesis in familial exudative vitreoretinopathy. Nat Genet. Oct. 2002;32(2):326-30. Epub Aug. 12, 2002.
Rodova et al., The polycystic kidney disease-1 promoter is a target of the beta-catenin/T-cell factor pathway. J Biol Chem. Aug. 16, 2002;277(33):29577-83. Epub Jun. 4, 2002.
Roos et al., Synthesis of α-Substituted α-Amino Acids via Cationic Intermediates. J Org Chem. 1993;58:3259-68.
Ross et al., Inhibition of adipogenesis by Wnt signaling. Science. Aug. 11, 2000;289(5481):950-3.
Rudinger, Characteristics of the amino acids as components of a peptide hormone sequence. In: Peptide Hormones. J. A. Parsons, ed. University Park Press. Jun. 1976:1-7.
Sali et al., Stabilization of protein structure by interaction of alpha-helix dipole with a charged side chain. Nature. Oct. 20, 1988;335(6192):740-3.
Sampietro et al., Crystal structure of a beta-catenin/BCL9/Tcf4 complex. Mol Cell. Oct. 20, 2006;24(2):293-300.
Satoh et al., AXIN1 mutations in hepatocellular carcinomas, and growth suppression in cancer cells by virus-mediated transfer of AXIN1. Nat Genet. Mar. 2000;24(3):245-50.
Sattler et al., Structure of Bcl-xL-Bak peptide complex: recognition between regulators of apoptosis. Science. Feb. 14, 1997;275(5302):983-6.
Saxon et al., Cell surface engineering by a modified Staudinger reaction. Science. Mar. 17, 2000;287(5460):2007-10.
Schäffer et al., A novel high-affinity peptide antagonist to the insulin receptor. Biochem Biophys Res Commun Nov. 14, 2008;376(2):380-3. doi: 10.1016/j.bbrc.2008.08.151. Epub Sep. 7, 2008.
Schäffer et al., Assembly of high-affinity insulin receptor agonists and antagonists from peptide building blocks. Proc Natl Acad Sci U S A. Apr. 15, 2003;100(8):4435-9. Epub Apr. 8, 2003.
Schafmiester et al., An All-Hydrocarbon Cross-Linking System for Enhancing the Helicity and Metabolic Stability of Peptides. J Am Chem Soc. 2000;122:5891-92.
Scheffzek et al., The Ras-RasGAP complex: structural basis for GTPase activation and its loss in oncogenic Ras mutants. Science. Jul. 18, 1997;277(5324):333-8.
Schinzel et al., The phosphate recognition site of Escherichia coli maltodextrin phosphorylase. FEBS Lett. Jul. 29, 1991;286(1-2):125-8.
Schmiedeberg et al., Reversible backbone protection enables combinatorial solid-phase ring-closing metathesis reaction (RCM) in peptides. Org Lett. Jan. 10, 2002;4(1):59-62.
Scholtz et al., The mechanism of alpha-helix formation by peptides. Annu Rev Biophys Biomol Struct. 1992;21:95-118.
Schrock et al., Tungsten(VI) Neopentylidyne Complexes. Organometallics. 1982;1:1645-51.
Schwarzer et al., Protein semisynthesis and expressed protein ligation: chasing a protein's tail. Curr Opin Chem Biol. Dec. 2005;9(6):561-9. Epub Oct. 13, 2005.
Scott et al., Evidence of insulin-stimulated phosphorylation and activation of the mammalian target of rapamycin mediated by a protein kinase B signaling pathway. Proc Natl Acad Sci U S A. Jun. 23, 1998;95(13):7772-7.
Seabra et al., Rab GTPases, intracellular traffic and disease. Trends Mol Med. Jan. 2002;8(1):23-30.
Shair, A closer view of an oncoprotein-tumor suppressor interaction. Chem Biol. Nov. 1997;4(11):791-4.
Shiba et al., Structural basis for Rab11-dependent membrane recruitment of a family of Rab11-interacting protein 3 (FIP3)/

(56) References Cited

OTHER PUBLICATIONS

Arfophilin-1. Proc Natl Acad Sci U S A. Oct. 17, 2006;103(42):15416-21. Epub Oct. 9, 2006.
Si et al., CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.
Siddle et al., Specificity in ligand binding and intracellular signalling by insulin and insulin-like growth factor receptors. Biochem Soc Trans. Aug. 2001;29(Pt 4):513-25.
Singh et al., Iridium(I)-catalyzed regio- and enantioselective allylic amidation.Tet. Lett. 2007;48 (40): 7094-7098.
Skinner et al., Basic helix-loop-helix transcription factor gene family phylogenetics and nomenclature. Differentiation. Jul. 2010;80(1):1-8. doi: 10.1016/j.diff.2010.02.003. Epub Mar. 10, 2010.
Smith et al., Structural resolution of a tandem hormone-binding element in the insulin receptor and its implications for design of peptide agonists. Proc Natl Acad Sci U S A. Apr. 13, 2010;107(15):6771-6. doi: 10.1073/pnas.1001813107. Epub Mar. 26, 2010.
Soucek et al., Modelling Myc inhibition as a cancer therapy. Nature. Oct. 2, 2008;455(7213):679-83. Epub Aug. 17, 2008.
Stein et al., Rab proteins and endocytic trafficking: potential targets for therapeutic intervention. Adv Drug Deliv Rev. Nov. 14, 2003;55(11):1421-37.
Stenmark et al., The Rab GTPase family. Genome Biol. 2001;2(5):3007.1-3007.7.
Still et al., Semianalytical Treatment of Solvation for Molecular Mechanics and Dynamics. J Am Chem Soc. 1990;112:6127-29.
Stueanaes et al., Beta-adrenoceptor stimulation potentiates insulin-stimulated PKB phosphorylation in rat cardiomyocytes via cAMP and PKA. Br J Pharmacol. May 2010;160(1):116-29. doi: 10.1111/j.1476-5381.2010.00677.x.
Su et al., Eradication of pathogenic beta-catenin by Skp1/Cullin/F box ubiquitination machinery. Proc Natl Acad Sci U S A. Oct. 28, 2003;100(22):12729-34. Epub Oct. 16, 2003.
Surinya et al., Role of insulin receptor dimerization domains in ligand binding, cooperativity, and modulation by anti-receptor antibodies. J Biol Chem. May 10, 2002;277(19):16718-25. Epub Mar. 1, 2002.
Takeda et al., Human sebaceous tumors harbor inactivating mutations in LEF1. Nat Med. Apr. 2006;12(4):395-7. Epub Mar. 26, 2006.
Tanaka, Design and synthesis of non-proteinogenic amino acids and secondary structures of their peptides. Yakugaku Zasshi. Oct. 2006;126(10):931-44. Japanese.
Thompson et al., Mutants of interleukin 13 with altered reactivity toward interleukin 13 receptors. J Biol Chem. Oct. 15, 1999;274(42):29944-50.
Thundimadathil, New Reactions with Click Chemistry. An R&D Magazine Webcast. Oct. 10, 2012. www.rdmag.com/articles/2012/10/new-reactions-click-chemistry. [Last accessed Feb. 13, 2013}.
Tian et al., The role of the Wnt-signaling antagonist DKK1 in the development of osteolytic lesions in multiple myeloma. N Engl J Med. Dec. 25, 2003;349(26):2483-94.
Tolbert et al., New methods for proteomic research: preparation of proteins with N-terminal cysteines for labeling and conjugation. Angew Chem Int Ed Engl. Jun. 17, 2002;41(12):2171-4.
Toniolo, Conformationally restricted peptides through short-range cyclizations. Int J Pept Protein Res. Apr. 1990;35(4):287-300.
Toomes et al., Mutations in LRP5 or FZD4 underlie the common familial exudative vitreoretinopathy locus on chromosome 11q. Am J Hum Genet. Apr. 2004;74(4):721-30. Epub Mar. 11, 2004.
Tornøe et al., Peptidotriazoles on solid phase: [1,2,3]-triazoles by regiospecific copper(i)-catalyzed 1,3-dipolar cyclo additions of terminal alkynes to azides. J Org Chem. May 3, 2002;67(9):3057-64.
Torrance et al., Combinatorial chemoprevention of intestinal neoplasia. Nat Med. Sep. 2000;6(9):1024-8.

Tsuji et al., Antiproliferative activity of REIC/Dkk-3 and its significant down-regulation in non-small-cell lung carcinomas. Biochem Biophys Res Commun Nov. 23, 2001;289(1):257-63.
Tsuruzoe et al., Insulin receptor substrate 3 (IRS-3) and IRS-4 impair IRS-1- and IRS-2-mediated signaling. Mol Cell Biol. Jan. 2001;21(1):26-38.
Ueki et al., Increased insulin sensitivity in mice lacking p85beta subunit of phosphoinositide 3-kinase. Proc Natl Acad Sci U S A. Jan. 8, 2002;99(1):419-24. Epub Dec. 18, 2001.
Ueki et al., Positive and negative regulation of phosphoinositide 3-kinase-dependent signaling pathways by three different gene products of the p85alpha regulatory subunit. Mol Cell Biol. Nov. 2000;20(21):8035-46.
Uesugi et al., The alpha-helical FXXPhiPhi motif in p53: TAF interaction and discrimination by MDM2. Proc Natl Acad Sci U S A. Dec. 21, 1999;96(26):14801-6.
Vaickus et al., Immune markers in hematologic malignancies. Crit Rev Oncol Hematol. Dec. 1991;11(4):267-97.
Van Genderen et al., Development of several organs that require inductive epithelial-mesenchymal interactions is impaired in LEF-1-deficient mice. Genes Dev. Nov. 15, 1994;8(22):2691-703.
Van Gijn et al., The wnt-frizzled cascade in cardiovascular disease. Cardiovasc Res. Jul. 2002;55(1):16-24.
Varallo et al., Beta-catenin expression in Dupuytren's disease: potential role for cell-matrix interactions in modulating beta-catenin levels in vivo and in vitro. Oncogene. Jun. 12, 2003;22(24):3680-4.
Venancio et al., Reconstructing the ubiquitin network: cross-talk with other systems and identification of novel functions. Genome Biol. 2009;10(3):R33. Epub Mar. 30, 2009.
Verdine et al., Stapled peptides for intracellular drug targets. Methods Enzymol. 2012;503:3-33. doi: 10.1016/B978-0-12-396962-0.00001-X.
Verdine et al., The challenge of drugging undruggable targets in cancer: lessons learned from targeting BCL-2 family members. Clin Cancer Res. Dec. 15, 2007;13(24):7264-70.
Verma et al., Small interfering RNAs directed against beta-catenin inhibit the in vitro and in vivo growth of colon cancer cells. Clin Cancer Res. Apr. 2003;9(4):1291-300.
Voet et al., Biochemistry. Second Edition. John Wiley & Sons, Inc. 1995:235-241.
Walensky et al., A stapled BID BH3 helix directly binds and activates BAX. Mol Cell. Oct. 20, 2006;24(2):199-210.
Walensky et al., Activation of apoptosis in vivo by a hydrocarbon-stapled BH3 helix. Science. Sep. 3, 2004;305(5689):1466-70.
Walter et al., Critical role for IL-13 in the development of allergen-induced airway hyperreactivity. J Immunol. Oct. 15, 2001;167(8):4668-75.
Wang et al., Inhibition of p53 degradation by Mdm2 acetylation. FEBS Lett. Mar. 12, 2004;561(1-3):195-201.
Wang, 4-Alkyl-2-trichloromethyloxazolidin-5-ones: Valuable Precursors to Enantiomerically Pure C- and N-Protected α-Alkyl Prolines. Synlett. 1999;1:33-36.
Weaver et al., Transition metal-catalyzed decarboxylative allylation and benzylation reactions.Chemical Rev. Mar. 9, 2011;111(3):1846-913.
Wei et al., Disorder and structure in the Rab11 binding domain of Rab11 family interacting protein 2. Biochemistry. Jan. 27, 2009;48(3):549-57. doi: 10.1021/bi8020197.
Wilen et al., Strategies in Optical Resolution. Tetrahedron. 1977;33:2725-36.
Wilen, Tables of Resolving Agents and Optical Resolutions. E.L. Eliel, ed. Universtify of Notre Dame Press, Notre Dame, IN. 1972:268-98.
Williams et al., Asymmetric Synthesis of Monosubstituted and α,α-Disubstituted α-Amino Acids via Diastereoselective Glycine Enolate Alkylations. J Am Chem Soc. 1991;113:9276-86.
Wills-Karp et al., Interleukin-13: central mediator of allergic asthma. Science. Dec. 18, 1998;282(5397):2258-61.
Wills-Karp, Interleukin-13 in asthma pathogenesis. Immunol Rev. Dec. 2004;202:175-90.
Wills-Karp, The gene encoding interleukin-13: a susceptibility locus for asthma and related traits. Respir Res. 2000;1(1):19-23. Epub Jul. 17, 2000.

(56) References Cited

OTHER PUBLICATIONS

Wilson et al., The FIP3-Rab11 protein complex regulates recycling endosome targeting to the cleavage furrow during late cytokinesis. Mol Biol Cell. Feb. 2005;16(2):849-60. Epub Dec. 15, 2004.

Xi et al., Use of DNA and peptide nucleic acid molecular beacons for detection and quantification of rRNA in solution and in whole cells. Appl Environ Microbiol. Sep. 2003;69(9):5673-8.

Xing et al., Crystal structure of a beta-catenin/axin complex suggests a mechanism for the beta-catenin destruction complex. Genes Dev. Nov. 15, 2003;17(22):2753-64. Epub Nov. 4, 2003.

Yang et al., Synthesis and helical structure of lactam bridged BH3 peptides derived from pro-apoptotic Bcl-2 family proteins. Bioorg Med Chem Lett. 2004;14:1403-06.

Yang et al., Therapeutic dosing with anti-interleukin-13 monoclonal antibody inhibits asthma progression in mice. J Pharmacol Exp Ther. Apr. 2005;313(1):8-15. Epub Jan. 11, 2005.

Yu et al., The role of Axin2 in calvarial morphogenesis and craniosynostosis. Development. Apr. 2005;132(8):1995-2005.

Zhang et al., A triazole-templated ring-closing metathesis for constructing novel fused and bridged triazoles. Chem Commun (Camb). Jun. 21, 2007;(23):2420-2.

Zhou et al., Identification of Ubiquitin Target Proteins Using Cell-Based Arrays. J Proteome Res. 2007;6:4397-4406.

Zhou et al., Lymphoid enhancer factor 1 directs hair follicle patterning and epithelial cell fate. Genes Dev. Mar. 15, 1995;9(6):700-13.

Zhou et al., Tyrosine kinase inhibitor STI-571/Gleevec down-regulates the beta-catenin signaling activity. Cancer Lett. Apr. 25, 2003;193(2):161-70.

Zimm et al., Theory of the Phase Transition between Helix and Random Coil in Polypeptide Chains. J Chem Phys. 1959;31:526-35.

Zor et al., Solution structure of the KIX domain of CBP bound to the transactivation domain of c-Myb. J Mol Biol. Mar. 26, 2004;337(3):521-34.

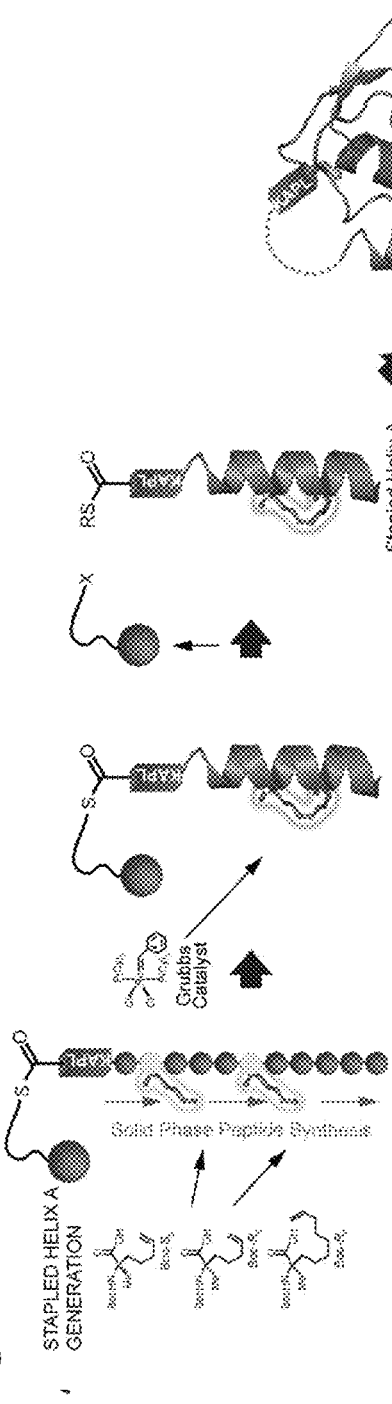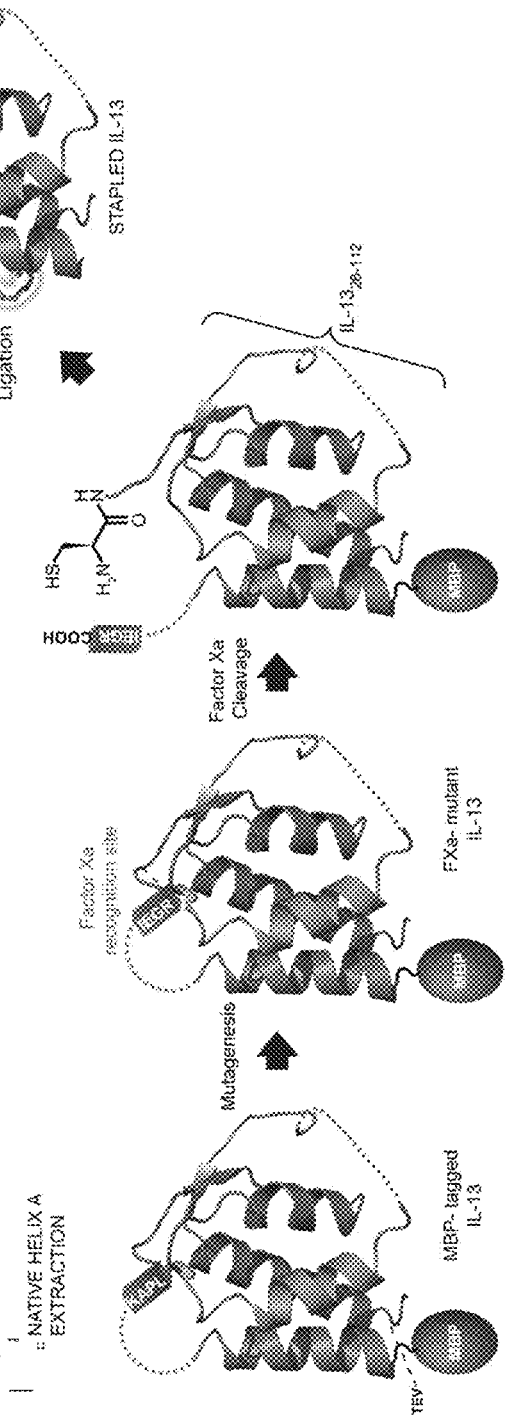
Figure 1A
Figure 1B

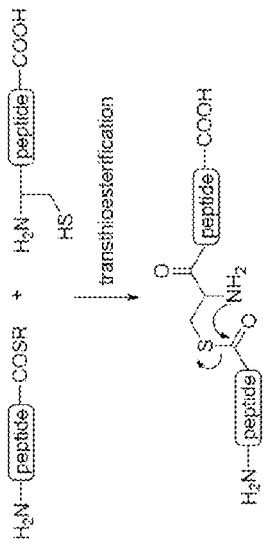
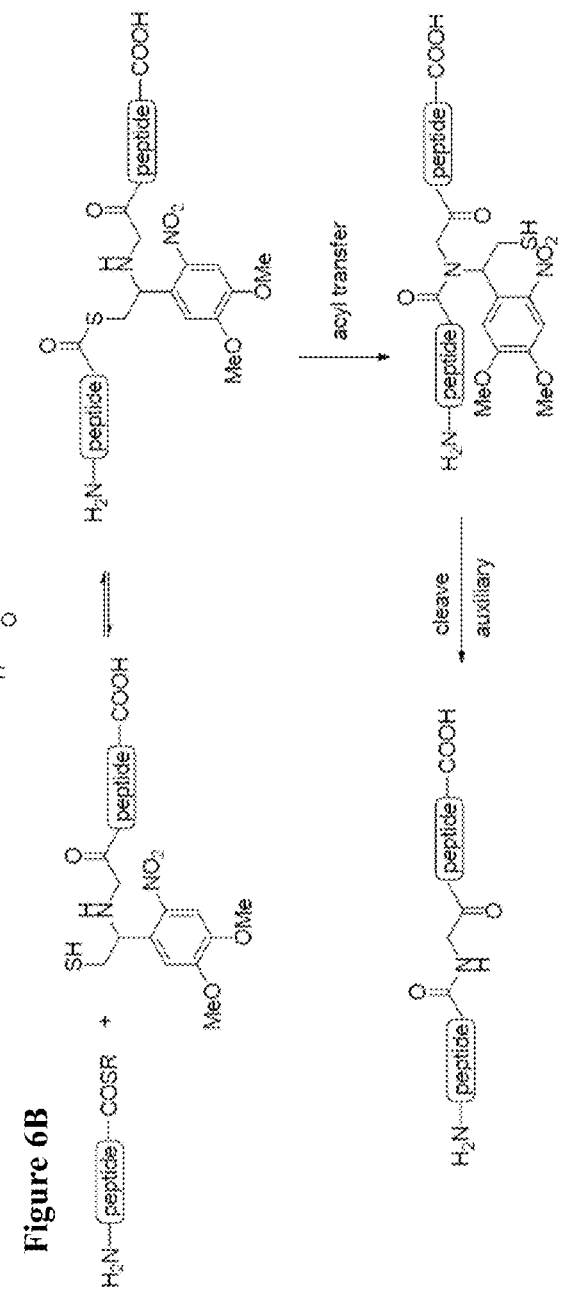
Figure 6A
Figure 6B

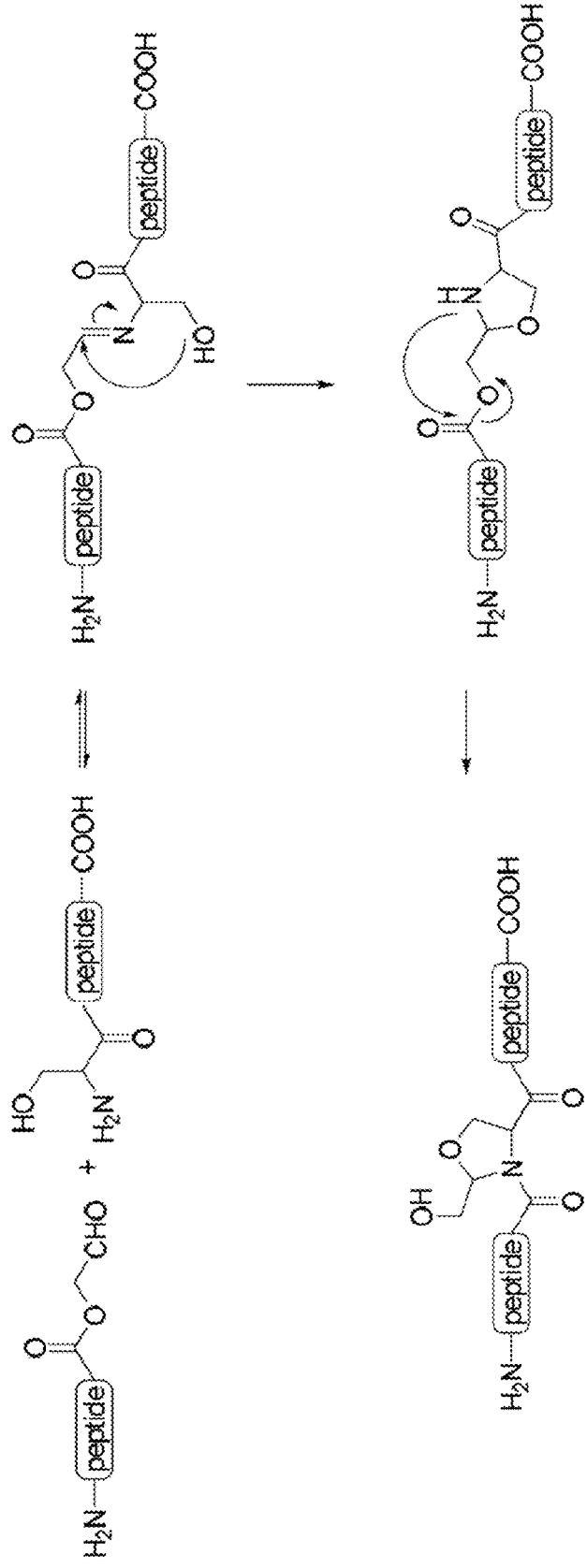
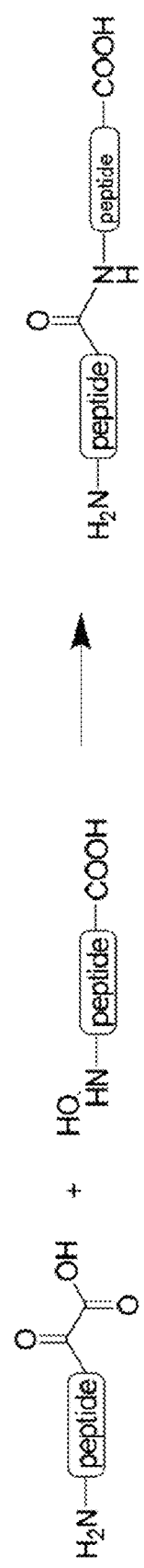
Figure 6D
Figure 6E

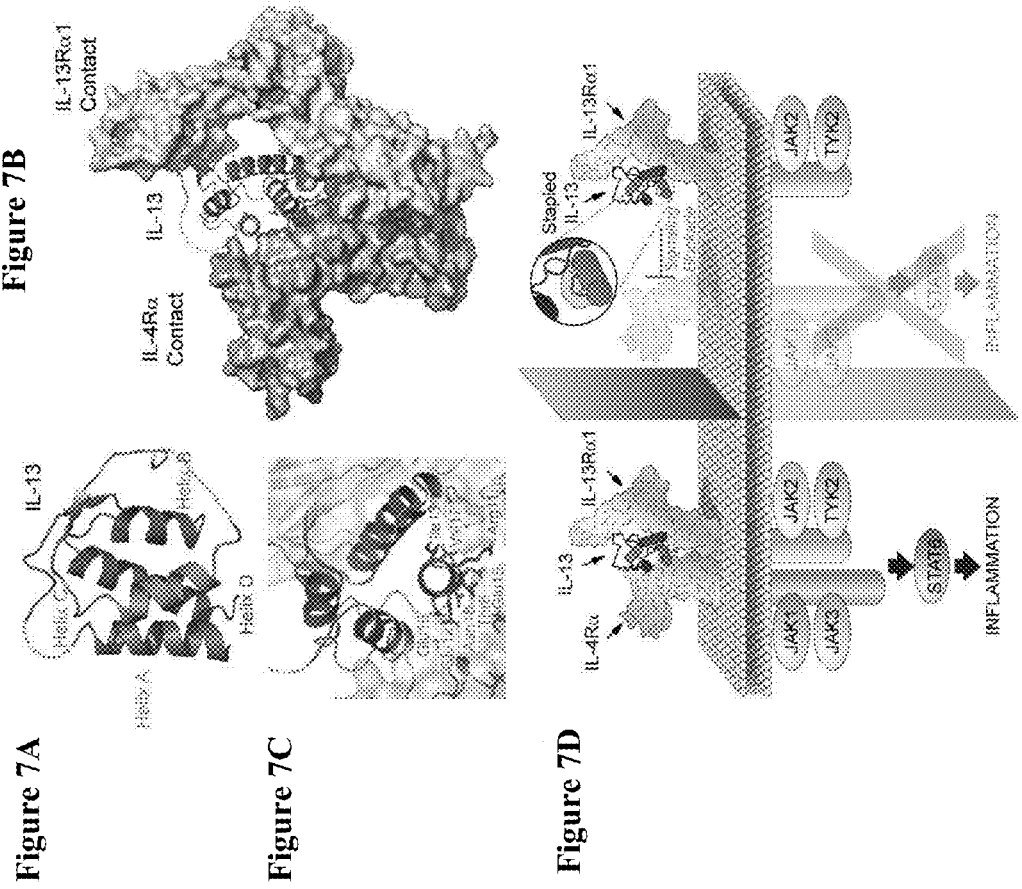

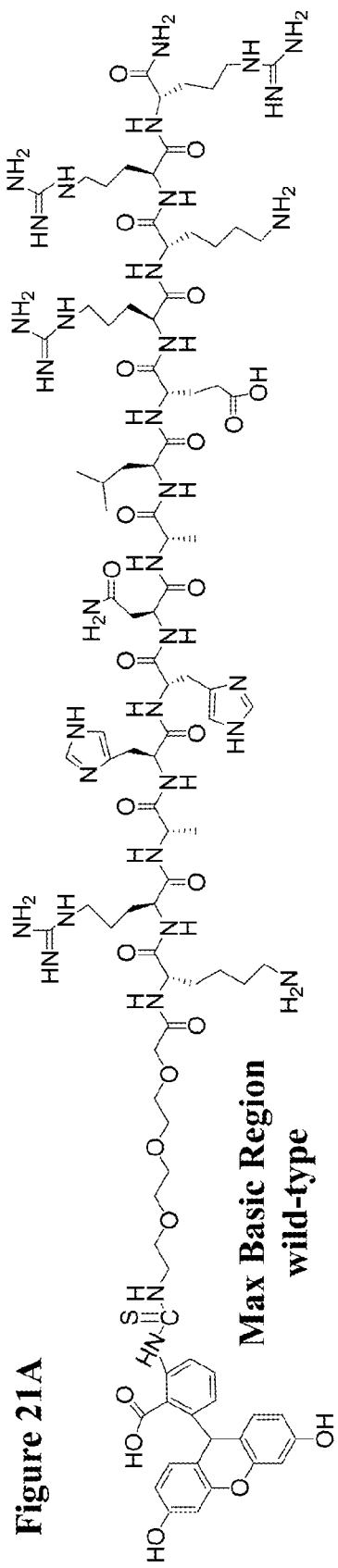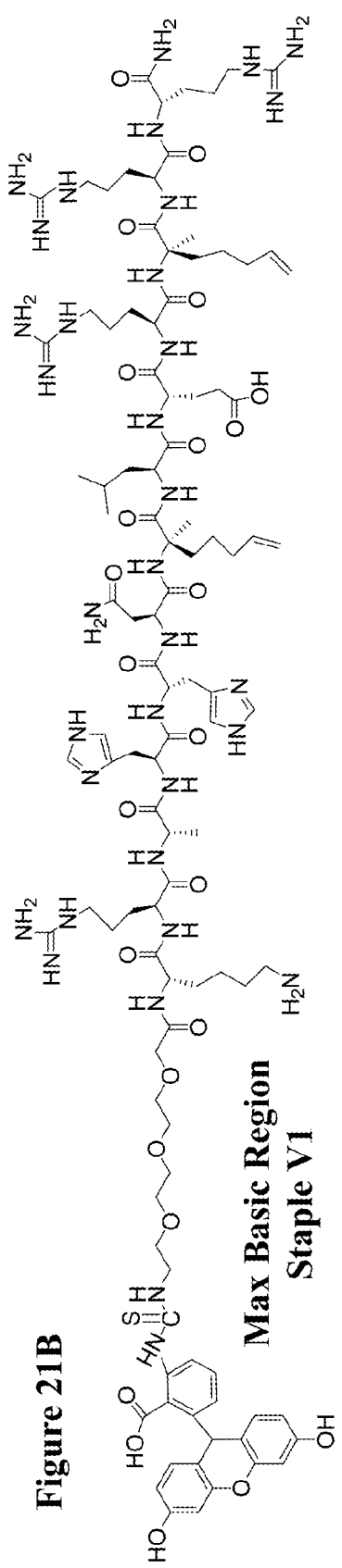
Figure 21A  Max Basic Region wild-type
Figure 21B  Max Basic Region Staple V1

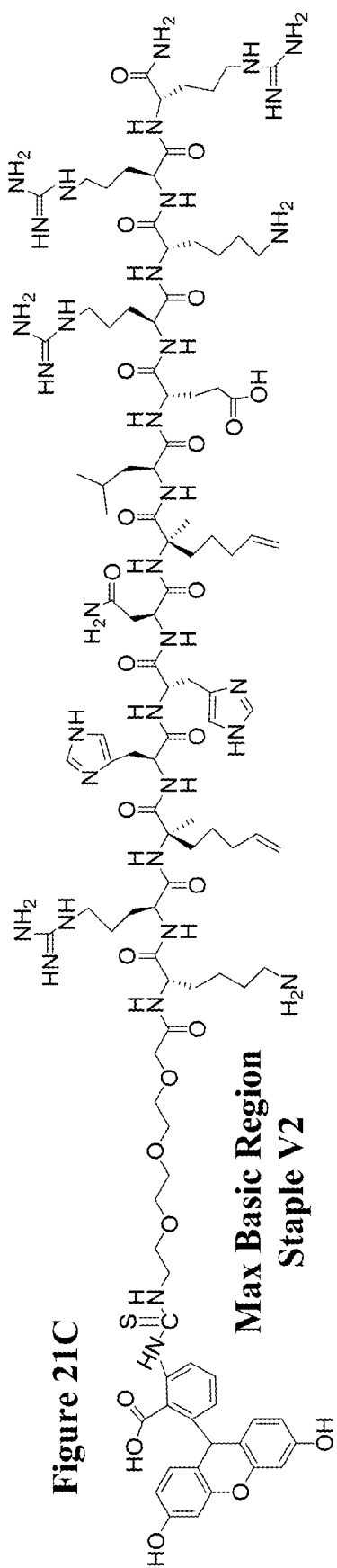
Figure 21C Max Basic Region Staple V2
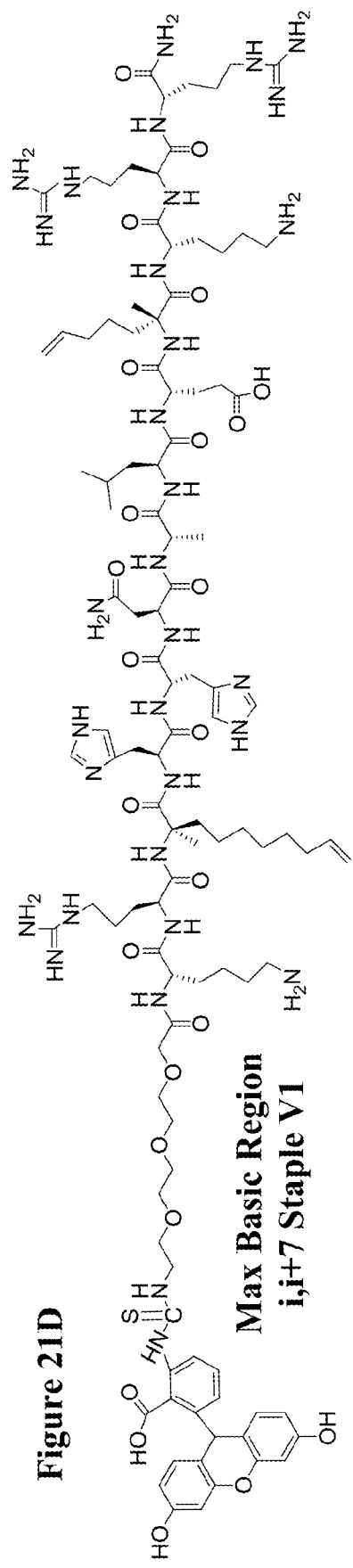
Figure 21D Max Basic Region i,i+7 Staple V1

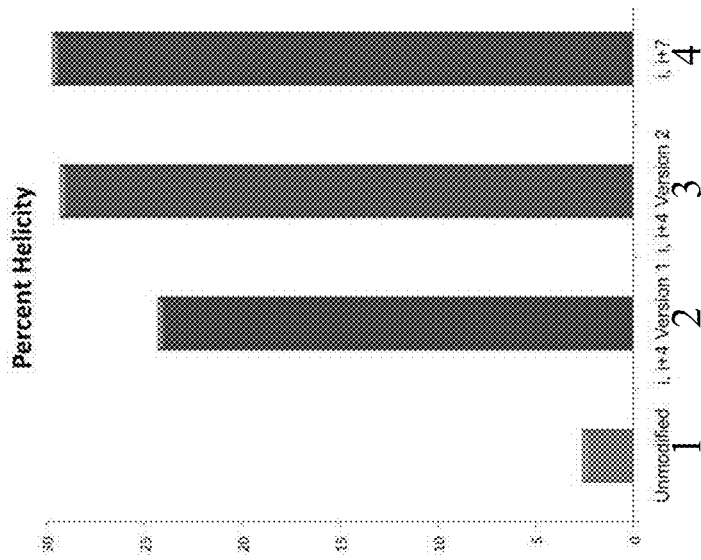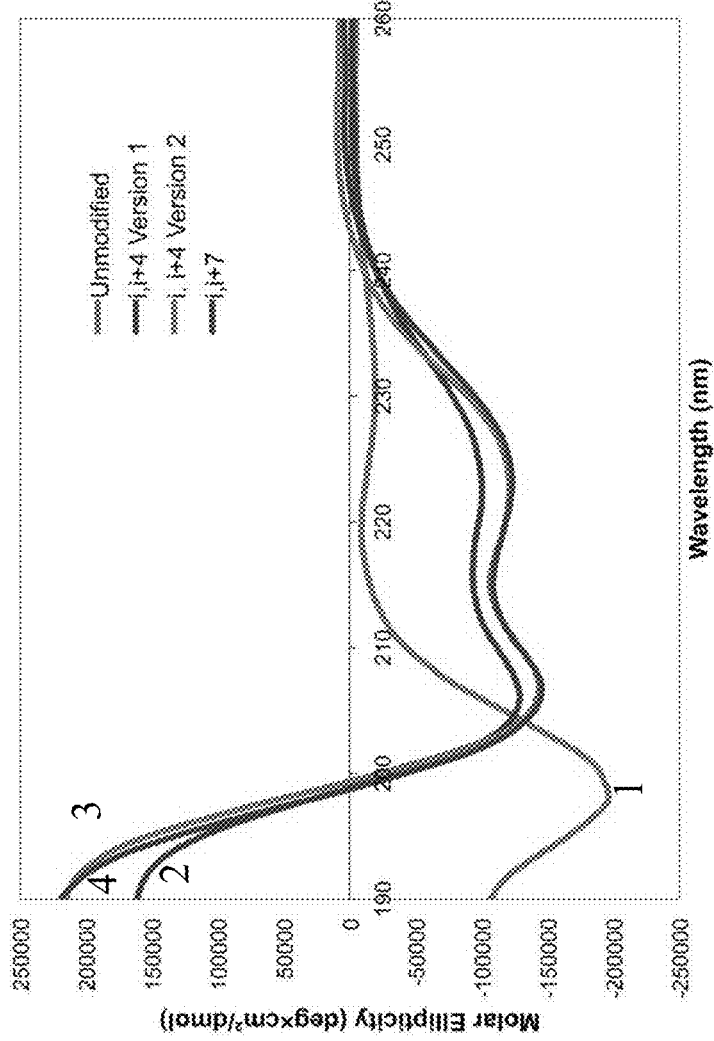

LIGATION OF STAPLED POLYPEPTIDES

RELATED APPLICATIONS

The present application is a divisional of and claims priority under 35 U.S.C. §120 to U.S. Application, U.S. Ser. No. 13/055,279, filed Jan. 21, 2011, which is a national stage filing under 35 U.S.C. §371 of international PCT application, PCT/US2009/004260, filed Jul. 23, 2009, which claims priority under 35 U.S.C. §119(e) to U.S. provisional patent applications, U.S. Ser. No. 61/082,935, filed Jul. 23, 2008, and U.S. Ser. No. 61/225,191, filed Jul. 13, 2009, each of which is incorporated herein by reference.

BACKGROUND OF THE INVENTION

Protein therapeutics represent the most rapidly expanding class of drugs, allowing for the treatment of patients with diabetes, cancer, neurological diseases, anemia, infectious diseases, and immunological diseases, among others. Proteins in their natural state are folded into regions of secondary structure, such as helices, sheets, and turns. The α-helix is one of the most common structural motifs found in proteins, and many biologically important protein interactions are mediated by the interaction of an α-helical region of one protein with another protein. However, α-helices have a propensity for unraveling and forming random coils, which are, in most cases, biologically less active, or even inactive, and are highly susceptible to proteolytic degradation.

Several research groups have developed strategies for the design and synthesis of stabilized secondary structures. Some efforts have focused on helix-stabilizing side chain interactions or template-nucleated α-helix formation (Scholtz and Baldwin, *Ann. Rev. Biophys. Biomol. Struct.* 1992, 21, 95). Another approach has been to stabilize the helix via covalent crosslinks. However, the majority of the reported methodologies involve the use of polar and/or labile crosslinking groups, such as disulfide bonds (see, for example, Phelan et al. *J. Am. Chem. Soc.* 1997, 119, 455; Leuc et al. *Proc. Nat'l. Acad. Sci. USA* 2003, 100, 11273; Bracken et al., *J. Am. Chem. Soc.* 1994, 116, 6432; Yan et al. *Bioorg. Med. Chem.* 2004, 14, 1403). Verdine and colleagues have developed an alternative olefin metathesis-based approach, which employs α,α-disubstituted non-natural amino acids containing alkenyl side chains, which are subsequently "stapled" together using an olefin metathesis catalyst (Schafmeister et al., *J. Am. Chem. Soc.* 2000, 122, 5891; Blackwell et al., *Angew. Chem. Intl. Ed.* 1994, 37, 3281). These stapled peptides have been shown to resist proteolytic cleavage, and a stapled α-helical peptide derived from the BH3 helix of Bcl-2 has demonstrated utility in blocking the growth of leukemia cells in mice (Walensky et al., *Science* 2004, 305, 1466). In some cases, stapling can impart on the peptide the ability to enter cells through vesicular transport. Stapling can greatly increase in vivo half-life, most likely through binding to human serum albumin, and stapling can also increase the affinity for a receptor by as much as $10^3$-$10^4$-fold.

Many proteins have α-helical segments that may benefit from covalent crosslinking to either stabilize the protein and/or alter a protein's biological activity. For example, the cytokine IL-13 has been identified as a therapeutic protein target, as it is strongly implicated in the pathogenesis of asthma. IL-13 is a soluble, secreted protein that folds to form a four-helix bundle structure (Moy et al., *J. Mol. Biol.* 2001, 310, 219; Eisenmesser et al., *J. Mol. Biol.* 2001, 310, 231).

IL-13 signals by simultaneously engaging two transmembrane receptor subunits, IL-4Rα and IL-13Rα, thus causing receptor dimerization. IL-13 binding to the heterodimeric receptor triggers phosphorylation of the signal transducer and activator of transcription-6 (STAT-6), ultimately leading to an allergic response (Kelly-Welch et al., *Science* 2003, 300, 1527). IL-13 and its heterodimeric receptor are widely considered to be among the more attractive targets for treating asthma (Wills-Karp, *Immunol. Rev.* 2004, 202, 175).

Given the need for stabilized protein therapeutics, some of which are larger than can be produced synthetically, there remains a need in the art for the efficient synthesis of proteins with a stapled or stitched peptide segment. Such a technology would allow for the production of large quantities of proteins greater than 50 amino acids in length with a stapled or stitched peptide segment. There are many reasons for incorporating a stapled or stitched segment into a protein; some stapled or stitched proteins may be targeted to certain tissues or cells or taken up by cells through vesicular transport. Some proteins could be converted from an agonist to an antagonist through the incorporation of a staple. A protein could also gain new function via stapling.

SUMMARY OF THE INVENTION

The present invention stems from the recognition that it would be desirable to produce large semi-synthetic stitched or stapled proteins. Such proteins may find use as therapeutics, as diagnostics, or as research tools. Typically, synthetic peptide technology only allows for the preparation of peptides of approximately 50 amino acids or less. Although larger proteins could theoretically be produced by current peptide synthesis methodology, it would be a monumental undertaking and would certainly not be feasible for producing large amounts of a protein (e.g., for use in the clinic). The present invention provides technology for producing large proteins with a stitched or stapled portion. In certain embodiments, the stitched or stapled portion is an α-helical portion. In some embodiments, the stitched or stapled portion is a bifunctional peptide as described in U.S. provisional patent application, U.S. Ser. No. 61/225,191, filed Jul. 13, 2009, which is incorporated herein by reference. The inventive method essentially involves ligating a synthetically produced stapled or stitched peptide to a larger protein that may have been produced recombinantly, purified from natural sources, or obtained by other means. The inventive method allows for the production of modified versions of cytokines (e.g., IL-13), transcription factors (e.g., myc), enzymes (e.g., streptokinase, urokinase), receptors, and hormones (e.g., insulin, erythropoietin). The modified protein may have altered biological activity (e.g., gain of function, increased activity, decreased activity, agonist to antagonist) or may simply have increased stability.

In one aspect, the invention provides methodology for preparing large stapled or stitched proteins, that is, proteins with one or more stapled or stitched peptide segments. Before the present invention, one was typically limited to approximately 50 amino acids in a stitched or stapled peptide because the unnatural amino acids necessary for the stapling or stitching could only be introduced into the peptide using synthetic methodology. Today practically speaking the limit of peptide synthesis is approximately 50 amino acids. The inventive method involves ligating a stitched or stapled peptide that has been produced synthetically to another protein or peptide (FIG. 1). Typically, the ligation is done to produce a scarless final product. For example, expressed protein ligation (EPL) may be used to produce the amide bond joining the stapled or stitched peptide to the other protein. The stapled or stitched peptide is produced synthetically with the necessary alkenyl amino acids for stapling or stitching. The peptide is optionally stapled or stitched with an olefin metathesis catalyst before it is ligated to the protein. Typically, the peptide is stapled or stitched before the ligation step; as more water-soluble metathesis catalysts become available, it may become more typical to staple or stitch a protein after the ligation step. The protein to which the peptide is being ligated can be produced using any known techniques for producing proteins. In certain embodiments, the protein is produced using recombinant technology. In other embodiments, the protein is purified from natural sources. The protein may be further processed (e.g., proteolytic cleavage) to achieve the desired end and/or sequence for ligation. For example, the whole protein may be produced recombinantly, and then the optionally purified protein cleaved to remove the segment that will be replaced with the stapled or stitched peptide segment. The stapled or stitched peptide and the optionally processed remaining protein are ligated together to form the final product. As would be appreciated by one of skill in the art, more than one stapled or stitched peptide may be ligated to the protein. For example, a peptide may be ligated to the C-terminus and N-terminus. Or two or more peptides may be ligated to each other and then ligated to a protein.

In another aspect, the invention provides large stapled or stitched proteins. These proteins are typically larger than those than can be produced synthetically. In certain embodiments, the stapled or stitched protein is greater than 50 amino acids in length. In certain embodiments, the stapled or stitched protein is greater than 75 or 100 amino acids in length. The inventive ligation methodology may be used to produce hormones (e.g., erythropoietin, insulin, growth hormone), cytokines (e.g., gamma-interferon, interleukin-13), antibodies, blood clotting factors (e.g., Factor VIII), enzymes (e.g., streptokinase), transcription factors (e.g., Myc), oncoproteins, receptors, or other proteins with a stitched or stapled peptide segment. In certain embodiments, the inventive protein has a stitched or stapled α-helical portion. In certain embodiments, the present invention provides a stapled version of IL-13. The stapled version of IL-13 has a staple in Helix A and/or D. In certain embodiments, the stapled version of IL-13 only contains a staple in Helix A. In certain embodiments, the stapled IL-13 binds IL-13Rα1 but has decreased binding to IL-4Rα. This modified version of IL-13 is a dominant negative form that may be useful in the treatment of asthma or other inflammatory diseases.

In another embodiment, the invention provides a modified version of the trascription factor, Myc or cMyc. The modified Myc protein described herein has a stapled leucine zipper portion that is designed to inhibit Max:Myc dimerization. The modified Myc protein acts as a dominant negative by occupying the DNA binding site and preventing transcription of the target gene. The modified Myc protein may be useful in the treatment of proliferative diseases such as cancer. The inventive modified proteins (e.g., IL-13, Myc) may be combined with a pharmaceutically acceptable excipient to form a pharmaceutical composition for administration to a subject (e.g., human) in need thereof.

In another aspect, the invention provides a stapled or stitched bifunctional peptide ligated to a protein, that is, the stapled or stitched peptide is a bifunctional peptide. A bifunctional peptide typically comprises two peptide domains, a targeting domain and an effector domain, tethered together by a linker. One or both of the targeting domain and effector domain of the bifunctional peptide are stapled or stitched to stabilize the conformation of the peptide. Each peptide comprises 5-50 amino acids as needed to act as a ligand for a targeted protein. The peptide may include unnatural amino acids with alkenyl side chains as necessary to form a staple or stitch used to stabilize the conformation of the peptide. In certain embodiments, the stapled or stitched peptide is a helical peptide. Typically, the two domains are covalently associated with one another through a linker; however, non-covalent associations may also be used. The linker may range in structure from simply a covalent bond to a bifunctional molecule to a polymeric linker. Given the stability of stapled peptides, they may be used as agents for recruiting proteins or other biomolecules to a particular protein, nucleic acid, other biomolecule, cell, or organelle (i.e., tethering two cellular components together or brining them into close proximity). One domain of the bifunctional peptide acts as a targeting moiety that binds to a target; the other domain acts as an effector domain to recruit a protein or protein complex to the target. The effector domain typically acts on or modifies the activity of the target. In essence, the bifunctional peptide works to bring two proteins or other biomolecules into close proximity to one another. Therefore, ligating a bifunctional stapled peptide to a protein allows for bringing three or more proteins into close proximity. Multimeric protein complexes may be formed using such inventive proteins with multiple interacting domains.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., a inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The compounds, proteins, or peptides of the present invention (e.g., amino acids, and unstapled, partially stapled, and stapled peptides and proteins, and unstitched, partially stitched, and stitched peptides and proteins) may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer.

Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); Wilen, *Tables of Resolving Agents and Optical Resolutions* p. 268 (E. L. Eliel, Ed., Univ. of Notre Dame Press, Notre Dame, Ind. 1972).

"Stapling" and "hydrocarbon-stapling" as used herein introduces into a peptide at least two moieties capable of undergoing reaction to promote carbon-carbon bond formation when contacted with a reagent to generate at least one cross-linker between the at least two moieties. Stapling provides a constraint on a secondary structure, such as an alpha-helical structure. The length and geometry of the cross-linker can be optimized to improve the yield of the desired secondary structure content. The constraint provided can, for example, prevent the secondary structure to unfold and/or can reinforce the shape of the secondary structure. A secondary structure that is prevented from unfolding is, for example, more stable.

A "stapled" peptide is a peptide comprising a selected number of standard or nonstandard amino acids, further comprising at least two moieties capable of undergoing reaction to promote carbon-carbon bond formation, that has been contacted with a reagent to generate at least one cross-linker between the at least two moieties, which modulates, for example, peptide stability.

A "stitched" peptide, as used herein, is a stapled peptide comprising more than one, that is multiple (two, three, four, five, six, etc.) cross-links (i.e., staples).

It will be appreciated that the compounds of the present invention, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substituents are illustrated by the specific embodiments shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

As used herein, substituent names which end in the suffix "-ene" refer to a biradical derived from the removal of two hydrogen atoms from the substitutent. Thus, for example, acyl is acylene; alkyl is alkylene; alkeneyl is alkenylene; alkynyl is alkynylene; heteroalkyl is heteroalkylene, heteroalkenyl is heteroalkenylene, heteroalkynyl is heteroalkynylene, aryl is arylene, and heteroaryl is heteroarylene.

The term "acyl," as used herein, refers to a group having the general formula $-C(=O)R^A$, $-C(=O)OR^A$, $-C(=O)-O-C(=O)R^A$, $-C(=O)SR^A$, $-C(=O)N(R^A)_2$, $-C(=S)R^A$, $-C(=S)N(R^A)_2$, and $-C(=S)S(R^A)$, $-C(=NR^A)R^A$, $-C(=NR^A)OR^A$, $-C(=NR^A)SR^A$, and $-C(=NR^A)N(R^A)_2$, wherein $R^A$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^A$ groups taken together form a 5- to 6-membered heterocyclic ring. Exemplary acyl groups include aldehydes ($-CHO$), carboxylic acids ($-CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula ($-OR^i$), wherein $R^i$ is an optionally substituted acyl group, as defined herein, and the oxygen moiety is directly attached to the parent molecule.

The term "acylene," as used herein, refers to an acyl group having the general formulae: $-R^O-(C=X^1)-R^O-$, $-R^O-X^2(C=X^1)-R^O-$, or $-R^O-X^2(C=X^1)X^3-R^O-$, where $X^1$, $X^2$, and $X^3$ is, independently, oxygen, sulfur, or $NR^r$, wherein $R^r$ is hydrogen or aliphatic, and $R^O$ is an optionally substituted alkylene, alkenylene, alkynylene, heteroalkylene, heteroalkenylene, or heteroalkynylene group, as defined herein. Exemplary acylene groups wherein $R^O$ is alkylene includes $-(CH_2)_T-O(C=O)-(CH_2)_T-$; $-(CH_2)_T-NR^r(C=O)-(CH_2)_T-$; $-(CH_2)_T-O(C=NR^r)-(CH_2)_T-$; $-(CH_2)_T-NR^r(C=NR^r)-(CH_2)_T-$; $-(CH_2)_T-(C=O)-(CH_2)_T-$; $-(CH_2)_T-(C=NR^r)-(CH_2)_T-$; $-(CH_2)_T-S(C=S)-(CH_2)_T-$; $-(CH_2)_T-NR^r(C=S)-(CH_2)_T-$; $-(CH_2)_T-S(C=NR^r)-(CH_2)_T-$; $-(CH_2)_T-O(C=S)-(CH_2)_T-$;

—(CH$_2$)$_T$—(C═S)—(CH$_2$)$_T$—; or —(CH$_2$)$_T$—S(C═O)—(CH$_2$)$_T$—, and the like, which may bear one or more substituents; and wherein each instance of xx is, independently, an integer between 0 to 20. Acylene groups may be cyclic or acyclic, branched or unbranched, substituted or unsubstituted. Acylene substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "amino," as used herein, refers to a group of the formula (—$NH_2$). A "substituted amino" refers either to a mono-substituted amine (—$NHR^h$) of a disubstitued amine (—$NR^h_2$), wherein the $R^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the $R^h$ substituents of the di-substituted amino group (—$NR^h_2$) form a 5- to 6-membered heterocyclic ring.

The term "alkoxy" refers to a "substituted hydroxyl" of the formula (—$OR^i$), wherein $R^i$ is an optionally substituted alkyl group, as defined herein, and the oxygen moiety is directly attached to the parent molecule.

The term "alkylthioxy" refers to a "substituted thiol" of the formula (—$SR^r$), wherein $R^r$ is an optionally substituted alkyl group, as defined herein, and the sulfur moiety is directly attached to the parent molecule.

The term "alkylamino" refers to a "substituted amino" of the formula (—$NR^h_2$), wherein $R^h$ is, independently, a hydrogen or an optionally substituted alkyl group, as defined herein, and the nitrogen moiety is directly attached to the parent molecule.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). Additionally, arylene groups may be incorporated as a linker group into an alkylene, alkenylene, alkynylene, heteroalkylene, heteroalkenylene, or heteroalkynylene group, as defined herein.

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. An exemplary arylalkyl group includes benzyl.

The term "aryloxy" refers to a "substituted hydroxyl" of the formula (—$OR^i$), wherein $R^i$ is an optionally substituted aryl group, as defined herein, and the oxygen moiety is directly attached to the parent molecule.

The term "arylamino," refers to a "substituted amino" of the formula (—$NR^h_2$), wherein $R^h$ is, independently, a hydrogen or an optionally substituted aryl group, as defined herein, and the nitrogen moiety is directly attached to the parent molecule.

The term "arylthioxy" refers to a "substituted thiol" of the formula (—$SR^r$), wherein $R^r$ is an optionally substituted aryl group, as defined herein, and the sulfur moiety is directly attached to the parent molecule.

The term "azido," as used herein, refers to a group of the formula (—N$_3$).

The term "cyano," as used herein, refers to a group of the formula (—CN).

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl," as used herein, refers to an alkyl moiety, as defined herein, which contain one or more oxygen, sulfur, nitrogen, phosphorus, or silicon atoms, e.g., in place of carbon atoms.

The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. Heteroalkylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkenyl," as used herein, refers to an alkenyl moiety, as defined herein, which contain one or more oxygen, sulfur, nitrogen, phosphorus, or silicon atoms, e.g., in place of carbon atoms.

The term "heteroalkenylene," as used herein, refers to a biradical derived from an heteroalkenyl group, as defined herein, by removal of two hydrogen atoms. Heteroalkenylene groups may be cyclic or acyclic, branched or unbranched, substituted or unsubstituted.

The term "heteroalkynyl," as used herein, refers to an alkynyl moiety, as defined herein, which contain one or more oxygen, sulfur, nitrogen, phosphorus, or silicon atoms, e.g., in place of carbon atoms.

The term "heteroalkynylene," as used herein, refers to a biradical derived from an heteroalkynyl group, as defined herein, by removal of two hydrogen atoms. Heteroalkynylene groups may be cyclic or acyclic, branched or unbranched, substituted or unsubstituted.

The term "heteroalkylamino" refers to a substituted amino of the formula (—NR$^h{}_2$), wherein R$^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula (—OR$^i$), wherein R$^i$ is an optionally substituted heteroalkyl group, as defined herein, and the oxygen moiety is directly attached to the parent molecule.

The term "heteroalkylthioxy" refers to a substituted thiol of the formula (—SR$^r$), wherein R$^r$ is an optionally substituted heteroalkyl group, as defined herein, and the sulfur moiety is directly attached to the parent molecule.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic 5- or 6-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bicyclic or tricyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a substituted amino of the formula (—$NR^h_2$), wherein $R^h$ is, independently, a hydrogen or an optionally substituted heteroaryl group, as defined herein, and the nitrogen moiety is directly attached to the parent molecule.

The term "heteroaryloxy" refers to a substituted hydroxyl of the formula (—$OR^i$), wherein $R^i$ is an optionally substituted heteroaryl group, as defined herein, and the oxygen moiety is directly attached to the parent molecule.

The term "heteroarylthioxy" refers to a substituted thiol of the formula (—$SR^r$), wherein $R^r$ is an optionally substituted heteroaryl group, as defined herein, and the sulfur moiety is directly attached to the parent molecule.

The term "hydroxy," or "hydroxyl," as used herein, refers to a group of the formula (—OH). A "substituted hydroxyl" refers to a group of the formula (—$OR^i$), wherein $R^i$ can be any substitutent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino," as used herein, refers to a group of the formula (=$NR^r$), wherein $R^r$ corresponds to hydrogen or any substitutent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted).

The term "isocyano," as used herein, refers to a group of the formula (—NC).

The term "nitro," as used herein, refers to a group of the formula (—$NO_2$).

The term "oxo," as used herein, refers to a group of the formula (=O).

As used herein, the term "resin" refers to a resin useful for solid phase synthesis. Solid phase synthesis is a well-known synthetic technique; see generally, Atherton, E., Sheppard, R. C. *Solid Phase Peptide Synthesis: A Practical Approach*, IRL Press, Oxford, England, 1989, and Stewart J. M., Young, J. D. *Solid Phase Peptide Synthesis,* 2nd edition, Pierce Chemical Company, Rockford, 1984, the entire contents of each of which are hereby incorporated herein by reference. Exemplary resins which may be employed by the present invention include, but are not limited to:

(1) alkenyl resins (e.g., REM resin, vinyl sulfone polymer-bound resin, vinyl-polystyrene resin);

(2) amine functionalized resins (e.g., amidine resin, N-(4-Benzyloxybenzyl)hydroxylamine polymer bound, (aminomethyl)polystyrene, polymer bound (R)-(+)-a-methylbenzylamine, 2-Chlorotrityl Knorr resin, 2-N-Fmoc-Aminodibenzocyclohepta-1,4-diene, polymer-bound resin, 4-[4-(1-Fmoc-aminoethyl)-2-methoxy-5-nitrophenoxy] butyramidomethyl-polystyrene resin, 4-Benzyloxybenzylamine, polymer-bound, 4-Carboxybenzenesulfonamide, polymer-bound, Bis(tert-butoxycarbonyl) thiopseudourea, polymer-bound, Dimethylaminomethylpolystyrene, Fmoc-3-amino-3-(2-nitrophenyl)propionic acid, polymer-bound, N-Methyl aminomethylated polystyrene, PAL resin, Sieber amide resin, tert-Butyl N-(2-mercaptoethyl)carbamate, polymer-bound, Triphenylchloromethane-4-carboxamide polymer bound);

(3) benzhydrylamine (BHA) resins (e.g., 2-Chlorobenzhydryl chloride, polymer-bound, HMPB-benzhydrylamine polymer bound, 4-Methylbenzhydrol, polymer-bound, Benzhydryl chloride, polymer-bound, Benzhydrylamine polymer-bound);

(4) Br-functionalized resins (e.g., 4-(Benzyloxy)benzyl bromide polymer bound, 4-Bromopolystyrene, Brominated PPOA resin, Brominated Wang resin, Bromoacetal, polymer-bound, Bromopolystyrene, HypoGel® 200 Br, Polystyrene A-Br for peptide synthesis, Selenium bromide, polymer-bound, TentaGel HL-Br, TentaGel MB-Br, TentaGel S-Br, TentaGel S-Br);

(5) Chloromethyl resins (e.g., 5-[4-(Chloromethyl)phenyl]pentyl]styrene, polymer-bound, 4-(Benzyloxy)benzyl chloride polymer bound, 4-Methoxybenzhydryl chloride, polymer-bound);

(6) CHO-functionalized resins (e.g., (4-Formyl-3-methoxyphenoxymethyl)polystyrene, (4-Formyl-3-methoxyphenoxymethyl)polystyrene, 3-Benzyloxybenzaldehyde, polymer-bound, 4-Benzyloxy-2,6-dimethoxybenzaldehyde, polymer-bound, Formylpolystyrene, HypoGel® 200 CHO, Indole resin, Polystyrene A-CH(OEt)$_2$, TentaGel HL-CH(OEt)$_2$);

(7) Cl-functionalized resins (e.g., Benzoyl chloride polymer bound, (Chloromethyl)polystyrene, Merrifield's resin);

(8) $CO_2H$ functionalized resins (e.g., Carboxyethylpolystryrene, HypoGel® 200 COOH, Polystyrene AM-COOH, TentaGel HL-COOH, TentaGel MB-COOH, TentaGel S-COOH);

(9) Hypo-Gel resins (e.g., HypoGel® 200 FMP, HypoGel® 200 PHB, HypoGel® 200 Trt-OH, HypoGel® 200 HMB);

(10) I-functionalized resins (e.g., 4-Iodophenol, polymer-bound, Iodopolystyrene); Janda-Jels™ (JandaJel$^a$-Rink amide, JandaJel-NH$_2$, JandaJel-Cl, JandaJel-4-Mercaptophenol, JandaJel-OH, JandaJel-1-(3-Dimethylaminopropyl)-3-ethylcarbodiimide, JandaJel-1,3,4,6,7,8-hexahydro-2H-pyrimido-[1,2-a] pyrimidine, JandaJel-morpholine, JandaJel-polypyridine, JandaJel-Triphenylphosphine, JandaJel-Wang);

(11) MBHA resins (3[4'-(Hydroxymethyl)phenoxy] propionic acid-4-methylbenzhydrylamine resin, 4-(Hydroxymethyl)phenoxyacetic acid polymer-bound to MBHA resin, HMBA-4-methylbenzhydrylamine polymer bound, 4-Methylbenzhydrylamine hydrochloride polymer bound Capacity (amine));

(12) NH$_2$ functionalized resins ((Aminomethyl)polystyrene, (Aminomethyl)polystyrene, HypoGel® 200 NH$_2$, Polystyrene AM-NH$_2$, Polystyrene Microspheres 2-aminoethylated, Polystyrol Microspheres 2-bromoethylated, Polystyrol Microspheres 2-hydroxyethylated, TentaGel HL-NH$_2$, Tentagel M Br, Tentagel M NH$_2$, Tentagel M OH, TentaGel MB-NH$_2$, TentaGel S-NH$_2$, TentaGel S-NH$_2$);

(13) OH-functionalized resins (e.g., 4-Hydroxymethylbenzoic acid, polymer-bound, Hydroxymethyl Resins, OH-functionalized Wang Resins);

(14) oxime resins (e.g., 4-Chlorobenzophenone oxime polymer bound, Benzophenone oxime polymer bound, 4-Methoxybenzophenone oxime polymer bound);

(15) PEG resins (e.g., ethylene glycol polymer bound);

(16) Boc-/Blz peptide synthesis resins (e.g., Boc-Lys(Boc)-Lys[Boc-Lys(Boc)]-Cys(Acm)-b-Ala-O-PAM resin, Boc-Lys(Fmoc)-Lys[Boc-Lys(Fmoc)]-b-Ala-O-Pam resin, Boc-Lys(Boc)-Lys[Boc-Lys(Boc)]-Lys{Boc-Lys(Boc)-Lys[Boc-Lys(Boc)]}-b-Ala-O-PAM resin, Boc-Lys(Fmoc)-Lys[Boc-Lys(Fmoc)]-Lys {Boc-Lys(Fmoc)-Lys[Boc-Lys(Fmoc)]}-b-Ala-O-PAM resin, Boc-Lys(Boc)-Lys[Boc-Lys(Boc)]-Lys {Boc-Lys(Boc)-Lys[Boc-Lys(Boc)]}-Cys(Acm)-b-Ala-O-PAM resin, Preloaded PAM resins);

(17) Fmoc-/t-Bu peptide synthesis resins (e.g., Fmoc-Lys(Fmoc)-Lys[Fmoc-Lys(Fmoc)]-b-Ala-O-Wang resin, Fmoc-Lys(Fmoc)-Lys[Fmoc-Lys(Fmoc)]-Lys {Fmoc-Lys(Fmoc)-Lys[Fmoc-Lys(Fmoc)]}-b-Ala-O-Wang resin, Preloaded TentaGel® S Trityl Resins, Preloaded TentaGel® Resins, Preloaded Trityl Resins, Preloaded Wang Resins, Trityl Resins Preloaded with Amino Alcohols);

(18) thiol-functionalized resins (e.g., HypoGel® 200 S-Trt, Polystyrene AM-S-Trityl, TentaGel HL-S-Trityl, TentaGel MB-S-Trityl, TentaGel S-S-Trityl); and

(19) Wang resins (e.g., Fmoc-Ala-Wang resin, Fmoc-Arg (Pbf)-Wang resin, Fmoc-Arg(Pmc)-Wang resin, Fmoc-Asn (Trt)-Wang resin, Fmoc-Asp(OtBu)-Wang resin, Fmoc-Cys (Acm)-Wang resin, Fmoc-Cys(StBu)-Wang resin, Fmoc-Cys(Trt) Wang resin, Fmoc-Gln(Trt)-Wang resin, Fmoc-Glu (OtBu)-Wang resin, Fmoc-Gly-Wang resin, Fmoc-His(Trt)-Wang resin, Fmoc-Ile-Wang resin, Fmoc-Leu-Wang resin, Fmoc-Lys(Boc)-Wang resin, Fmoc-Met-Wang resin, Fmoc-D-Met-Wang resin, Fmoc-Phe-Wang resin, Fmoc-Pro-Wang resin, Fmoc-Ser(tBu)-Wang resin, Fmoc-Ser(Trt)-Wang resin, Fmoc-Thr(tBu)-Wang resin, Fmoc-Trp(Boc) Wang resin, Fmoc-Trp-Wang resin, Fmoc-Tyr(tBu)-Wang resin, Fmoc-Val-Wang resin).

The term "stable moiety," as used herein, preferably refers to a moiety which possess stability sufficient to allow manufacture, and which maintains its integrity for a sufficient period of time to be useful for the purposes detailed herein.

A "suitable amino-protecting group," as used herein, is well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10, 10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), P3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable carboxylic acid protecting group," or "protected carboxylic acid," as used herein, are well known in the art and include those described in detail in Greene (1999). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "suitable hydroxyl protecting group" as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

A "suitable thiol protecting group," as used herein, are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected thiol groups further include, but are not limited to, thioesters, carbonates, sulfonates allyl thioethers, thioethers, silyl thioethers, alkyl thioethers, arylalkyl thioethers, and alkyloxyalkyl thioethers. Examples of suitable ester groups include formates, acetates, proprionates, pentanoates, crotonates, and benzoates. Specific examples of suitable ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxycrotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl groups include trimethylsilyl, triethylsilyl, t-butyldimethylsilyl, t-butyldiphenylsilyl, triisopropylsilyl ether, and other trialkylsilyl ethers. Examples of suitable alkyl groups include methyl, benzyl, p-methoxybenzyl, 3,4-dimethoxybenzyl, trityl, t-butyl, and allyl ether, or derivatives thereof. Examples of suitable arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

The term "thio," or "thiol," as used herein, refers to a group of the formula (—SH). A "substituted thiol" refers to a group of the formula (—SR$^r$), wherein R$^r$ can be any substituent that results in the formation of a stable moiety (e.g., a suitable thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "thiooxo," as used herein, refers to a group of the formula (=S).

As used herein, a "pharmaceutically acceptable form thereof" includes any pharmaceutically acceptable salts, prodrugs, tautomers, isomers, and/or polymorphs of a compound of the present invention, as defined below and herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "prodrug" refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage. In recent years several types of bioreversible derivatives have been exploited for utilization in designing prodrugs. Using esters as a prodrug type for compounds containing a carboxyl or hydroxyl functionality is known in the art as described, for example, in "The Organic Chemistry of Drug Design and Drug Interaction" Richard Silverman, published by Academic Press (1992).

As used herein, the term "tautomer" includes two or more interconvertable compounds resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

As used herein, "polymorph" refers to a crystalline inventive compound existing in more than one crystaline form/structure. When polymorphism exists as a result of difference in crystal packing, it is called packing polymorphism. Polymorphism can also result from the existence of different conformers of the same molecule in conformational polymorphism. In pseudopolymorphism, the different crystal types are the result of hydration or solvation.

The term "amino acid" refers to a molecule containing both an amino group and a carboxyl group. Amino acids include alpha-amino acids and beta-amino acids, the structures of which are depicted below. In certain embodiments, an amino acid is an alpha amino acid.

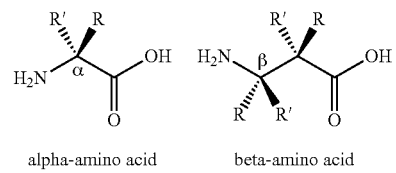

alpha-amino acid        beta-amino acid

Suitable amino acids include, without limitation, natural alpha-amino acids such as D- and L-isomers of the 20 common naturally occurring alpha-amino acids found in peptides (e.g., A, R, N, C, D, Q, E, G, H, I, L, K, M, F, P, S, T, W, Y, V, as provided in Table 1 depicted below), unnatural alpha-amino acids (as depicted in Tables 2 and 3 below), natural beta-amino acids (e.g., beta-alanine), and unnnatural beta-amino acids.

Amino acids used in the construction of peptides of the present invention may be prepared by organic synthesis, or obtained by other routes, such as, for example, degradation of or isolation from a natural source. In certain embodiments of the present invention, the formula —[$X_{AA}$]— corresponds to the natural and/or unnatural amino acids having the following formulae:

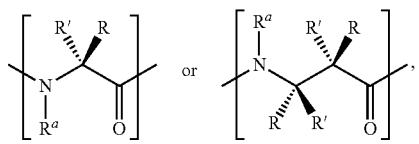

wherein R and R' correspond a suitable amino acid side chain, as defined below and herein, and $R^a$ is as defined below and herein.

TABLE 1

| Exemplary natural alpha-amino acids | Suitable amino acid side chains | |
|---|---|---|
| | R | R' |
| L-Alanine (A) | —CH$_3$ | —H |
| L-Arginine (R) | —CH$_2$CH$_2$CH$_2$—NHC(=NH)NH$_2$ | —H |
| L-Asparagine (N) | —CH$_2$C(=O)NH$_2$ | —H |
| L-Aspartic acid (D) | —CH$_2$CO$_2$H | —H |
| L-Cysteine (C) | —CH$_2$SH | —H |
| L-Glutamic acid (E) | —CH$_2$CH$_2$CO$_2$H | —H |
| L-Glutamine (Q) | —CH$_2$CH$_2$C(=O)NH$_2$ | —H |
| Glycine (G) | —H | —H |
| L-Histidine (H) | —CH$_2$-2-(1H-imidazole) | —H |
| L-Isoleucine (I) | -sec-butyl | —H |
| L-Leucine (L) | -iso-butyl | —H |
| L-Lysine (K) | —CH$_2$CH$_2$CH$_2$CH$_2$NH$_2$ | —H |
| L-Methionine (M) | —CH$_2$CH$_2$SCH$_3$ | —H |
| L-Phenylalanine (F) | —CH$_2$Ph | —H |
| L-Proline (P) | -2-(pyrrolidine) | —H |
| L-Serine (S) | —CH$_2$OH | —H |
| L-Threonine (T) | —CH$_2$CH(OH)(CH$_3$) | —H |
| L-Tryptophan (W) | —CH$_2$-3-(1H-indole) | —H |
| L-Tyrosine (Y) | —CH$_2$-(p-hydroxyphenyl) | —H |
| L-Valine (V) | -isopropyl | —H |

TABLE 2

| Exemplary unnatural alpha-amino acids | Suitable amino acid side chains | |
|---|---|---|
| | R | R' |
| D-Alanine | —H | —CH$_3$ |
| D-Arginine | —H | —CH$_2$CH$_2$CH$_2$—NHC(=NH)NH$_2$ |
| D-Asparagine | —H | —CH$_2$C(=O)NH$_2$ |
| D-Aspartic acid | —H | —CH$_2$CO$_2$H |
| D-Cysteine | —H | —CH$_2$SH |
| D-Glutamic acid | —H | —CH$_2$CH$_2$CO$_2$H |
| D-Glutamine | —H | —CH$_2$CH$_2$C(=O)NH$_2$ |
| D-Histidine | —H | —CH$_2$-2-(1H-imidazole) |
| D-Isoleucine | —H | -sec-butyl |
| D-Leucine | —H | -iso-butyl |
| D-Lysine | —H | —CH$_2$CH$_2$CH$_2$CH$_2$NH$_2$ |
| D-Methionine | —H | —CH$_2$CH$_2$SCH$_3$ |
| D-Phenylalanine | —H | —CH$_2$Ph |
| D-Proline | —H | -2-(pyrrolidine) |
| D-Serine | —H | —CH$_2$OH |
| D-Threonine | —H | —CH$_2$CH(OH)(CH$_3$) |
| D-Tryptophan | —H | —CH$_2$-3-(1H-indole) |
| D-Tyrosine | —H | —CH$_2$-(p-hydroxyphenyl) |
| D-Valine | —H | -isopropyl |
| Di-vinyl | —CH=CH$_2$ | —CH=CH$_2$ |

| Exemplary unnatural alpha-amino acids | R and R' are equal to: | |
|---|---|---|
| α-methyl-Alanine (Aib) | —CH$_3$ | —CH$_3$ |
| α-methyl-Arginine | —CH$_3$ | —CH$_2$CH$_2$CH$_2$—NHC(=NH)NH$_2$ |
| α-methyl-Asparagine | —CH$_3$ | —CH$_2$C(=O)NH$_2$ |
| α-methyl-Aspartic acid | —CH$_3$ | —CH$_2$CO$_2$H |
| α-methyl-Cysteine | —CH$_3$ | —CH$_2$SH |
| α-methyl-Glutamic acid | —CH$_3$ | —CH$_2$CH$_2$CO$_2$H |
| α-methyl-Glutamine | —CH$_3$ | —CH$_2$CH$_2$C(=O)NH$_2$ |
| α-methyl-Histidine | —CH$_3$ | —CH$_2$-2-(1H-imidazole) |
| α-methyl-Isoleucine | —CH$_3$ | -sec-butyl |
| α-methyl-Leucine | —CH$_3$ | -iso-butyl |
| α-methyl-Lysine | —CH$_3$ | —CH$_2$CH$_2$CH$_2$CH$_2$NH$_2$ |
| α-methyl-Methionine | —CH$_3$ | —CH$_2$CH$_2$SCH$_3$ |
| α-methyl-Phenylalanine | —CH$_3$ | —CH$_2$Ph |
| α-methyl-Proline | —CH$_3$ | -2-(pyrrolidine) |
| α-methyl-Serine | —CH$_3$ | —CH$_2$OH |
| α-methyl-Threonine | —CH$_3$ | —CH$_2$CH(OH)(CH$_3$) |
| α-methyl-Tryptophan | —CH$_3$ | —CH$_2$-3-(1H-indole) |
| α-methyl-Tyrosine | —CH$_3$ | —CH$_2$-(p-hydroxyphenyl) |
| α-methyl-Valine | —CH$_3$ | -isopropyl |
| Di-vinyl | —CH=CH$_2$ | —CH=CH$_2$ |
| Norleucine | —H | —CH$_2$CH$_2$CH$_2$CH$_3$ |

TABLE 3

| Exemplary unnatural alpha-amino acids | Suitable amino acid side chains R and R' is equal to hydrogen or —CH$_3$, and: |
|---|---|
| Terminally unsaturated alpha-amino acids and bis alpha-amino acids(e.g., modified cysteine, modified lysine, modified tryptophan, modified serine, modified threonine, modified proline, modified histidine, modified alanine, and the like). | —(CH$_2$)$_g$—S—(CH$_2$)$_g$CH=CH$_2$, <br> —(CH$_2$)$_g$—O—(CH$_2$)$_g$CH=CH$_2$, <br> —(CH$_2$)$_g$—NH—(CH$_2$)$_g$CH=CH$_2$, <br> —(CH$_2$)$_g$—(C=O)—S—(CH$_2$)$_g$CH=CH$_2$, <br> —(CH$_2$)$_g$—(C=O)—O—(CH$_2$)$_g$CH=CH$_2$, <br> —(CH$_2$)$_g$—(C=O)—NH—(CH$_2$)$_g$CH=CH$_2$, <br> —CH$_2$CH$_2$CH$_2$CH$_2$—NH—(CH$_2$)$_g$CH=CH$_2$, <br> —(C$_6$H$_5$)—p—O—(CH$_2$)$_g$CH=CH$_2$, <br> —CH(CH$_3$)—O—(CH$_2$)$_g$CH=CH$_2$, <br> —CH$_2$CH(—O—CH=CH$_2$)(CH$_3$), <br> -histidine-N((CH$_2$)$_g$CH=CH$_2$), <br> -tryptophan-N((CH$_2$)$_g$CH=CH$_2$), and <br> —(CH$_2$)$_{g+1}$(CH=CH$_2$), <br> wherein: <br> each instance of g is, independently, 0 to 10. |

TABLE 3-continued

Exemplary unnatural alpha-amino acids

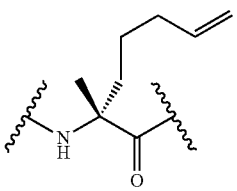 [SMILES: *N[C@](C)(CCCC=C)C(*)=O]

$R_5$

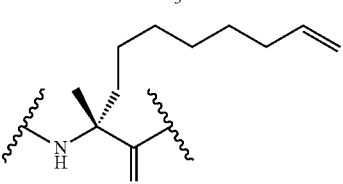

$R_8$

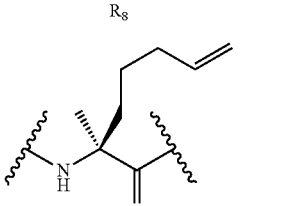

$S_5$

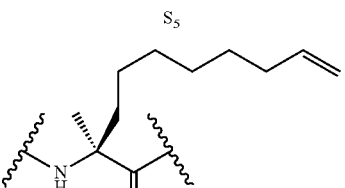

$S_8$

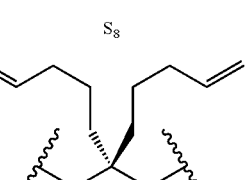

$B_5$

There are many known unnatural amino acids any of which may be included in the peptides of the present invention. See for example, S. Hunt, *The Non-Protein Amino Acids: In Chemistry and Biochemistry of the Amino Acids*, edited by G. C. Barrett, Chapman and Hall, 1985. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C(=O)C$_6$H$_5$; —CF$_3$; —CN; -halo; —NO$_2$; CH$_3$), and statine. Additionally, the amino acids suitable for use in the present invention may be derivatized to include amino acid residues that are hydroxylated, phosphorylated, sulfonated, acylated, and glycosylated, to name a few.

The term "amino acid side chain" refers to a group attached to the alpha- or beta-carbon of an amino acid. A "suitable amino acid side chain" includes, but is not limited to, any of the suitable amino acid side chains as defined above, and as provided in Tables 1 to 3.

For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in crosslinking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted. Terminally unsaturated amino acid side chains include, but are not limited to, side chains as depicted in Table 3.

A "peptide" or "polypeptide" comprises a polymer of amino acid residues linked together by peptide (amide) bonds. The term(s), as used herein, refers to proteins, polypeptides, and peptide of any size, structure, or function. Typically, a peptide or polypeptide will be at least three amino acids long. A peptide or polypeptide may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof. As used herein "dipeptide" refers to two covalently linked amino acids.

The following definitions are more general terms used throughout the present application:

The term "subject," as used herein, refers to any animal. In certain embodiments, the subject is a mammal. In certain embodiments, the term "subject", as used herein, refers to a human (e.g., a man, a woman, or a child).

The terms "administer," "administering," or "administration," as used herein refers to implanting, absorbing, ingesting, injecting, or inhaling, the inventive polypeptide or compound.

The terms "treat" or "treating," as used herein, refers to partially or completely alleviating, inhibiting, ameliorating, and/or relieving the disease or condition from which the subject is suffering.

The terms "effective amount" and "therapeutically effective amount," as used herein, refer to the amount or concentration of a biologically active agent conjugated to an inventive polypeptide of the presently claimed invention, or amount or concentration of an inventive polypeptide, that, when administered to a subject, is effective to at least partially treat a condition from which the subject is suffering.

As used herein, when two entities are "associated with" one another they are linked by a direct or indirect covalent or non-covalent interaction. In certain embodiments, the association is covalent and the entities are "conjugated" to one another. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently associated through a linker.

As used herein, when two entities are "conjugated" to one another they are linked by a direct or indirect covalent interaction. An indirect covalent interaction is when two entities are covalently connected, optionally through a linker.

As used herein, a "label" refers to a moiety that has at least one element, isotope, or functional group incorporated into the moiety which enables detection of the inventive polypeptide to which the label is attached. Labels can be directly attached (ie, via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). It will be appreciated that the label may be attached to the inventive polypeptide at any position that does not interfere with the biological activity or characteristic of the inventive polypeptide that is being detected.

In general, a label can fall into any one (or more) of five classes: a) a label which contains isotopic moieties, which may be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{169}$Yb, and $^{186}$Re; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label FITC); d) a label which has one or more photoaffinity moieties; and e) a label which has a ligand moiety with one or more known binding partners (such as biotin-streptavidin, FK506-FKBP, etc.). Such labels may be used in diagnostic agents.

In certain embodiments, such as in the identification of a biological target, label comprises a radioactive isotope, preferably an isotope which emits detectable particles, such as βparticles. In certain embodiments, the label comprises one or more photoaffinity moieties for the direct elucidation of intermolecular interactions in biological systems. A variety of known photophores can be employed, most relying on photoconversion of diazo compounds, azides, or diazirines to nitrenes or carbenes (see, Bayley, *Photogenerated Reagents in Biochemistry and Molecular Biology* (1983), Elsevier, Amsterdam, the entire contents of which are incorporated herein by reference). In certain embodiments of the invention, the photoaffinity labels employed are o-, m-, and p-azidobenzoyls, substituted with one or more halogen moieties, including, but not limited to, 4-azido-2,3,5,6-tetrafluorobenzoic acid.

In certain embodiments, the label comprises one or more fluorescent moieties. In certain embodiments, the label is the fluorescent label FITC. In certain embodiments, the label comprises a ligand moiety with one or more known binding partners. In certain embodiments, the label comprises the ligand moiety biotin.

As used herein, a "diagnostic agent" refers to imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P, and $^{18}$F. Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and *Handbook of Fluorescent Probes and Research Products*, Molecular Probes, 9$^{th}$ edition, 2002).

BRIEF DESCRIPTION OF THE DRAWINGS

FIGS. 1A-1B. Scheme for semi-synthetic construction of a stapled version of IL-13 by helix-swapping. (A) Solid-phase synthesis of the stapled Helix-A peptide possessing a C-terminal thioester. (B) A route for generation of IL-13$_{26-112}$. (A+B) Combining the stapled Helix-A thioester with IL-13$_{26-112}$ will enable expressed protein ligation to occur, thereby generating stapled IL-13; this differs from the wild-type cytokine only by the presence of the staple.

FIG. 6A-6E. Five possible chemical ligation strategies. "Peptide" can be a short, synthetic peptide or a larger protein produced recombinantly or purified from a natural source. (A) Native chemical ligation. (B) Native chemical ligation using a removable auxiliary. (C) Staudinger ligation. PG is a suitable amino protecting group, and R is a suitable carboxyl protecting group. (D) Imine ligation. (E) Amide ligation by decarboxylative condensation of N-hydroxylamine and α-ketoacid.

FIGS. 7A-7D. Structure of IL-13 and of its complex with the two receptor subunits, IL-4Rα and IL-13Rα1. (A) Overall structure of the IL-13 four helix bundle structure, with component helices colored individually. Dashed lines denote disordered regions. (B) Structure of IL-13 bound to IL-4Rα (grey) and IL-13Rα1 (pink). (C) Close-up view of the interface between Helix-A and IL-4Rα and IL-13Rα1, with key contact residues highlighted according to the receptor subunit they contact; blue, IL-4Rα; red, IL-13Rα1. (D) Schematic illustration of the active receptor/ligand complex (left) and mode of dominant negative inhibition by attachment of a hydrocarbon staple (highlighted in blue) that blocks binding to IL-4Rα.

FIGS. 21A-21D. Structures of synthesized basic region peptides. Non-natural amino acids were introduced at positions that are not involved in DNA binding. The terminal olefins were linked together using ring-closing metathesis chemistry to promote stability of an alpha-helical secondary structure.

FIGS. 22A-22B. Structural characterization of peptides derived from the basic region of Max. A.) Circular dichroism wavelength scans. B. The overall helicity of each peptide was calculated using the molar ellipticity value at 222 nm.

DETAILED DESCRIPTION OF CERTAIN EMBODIMENTS OF THE INVENTION

Figure 2:
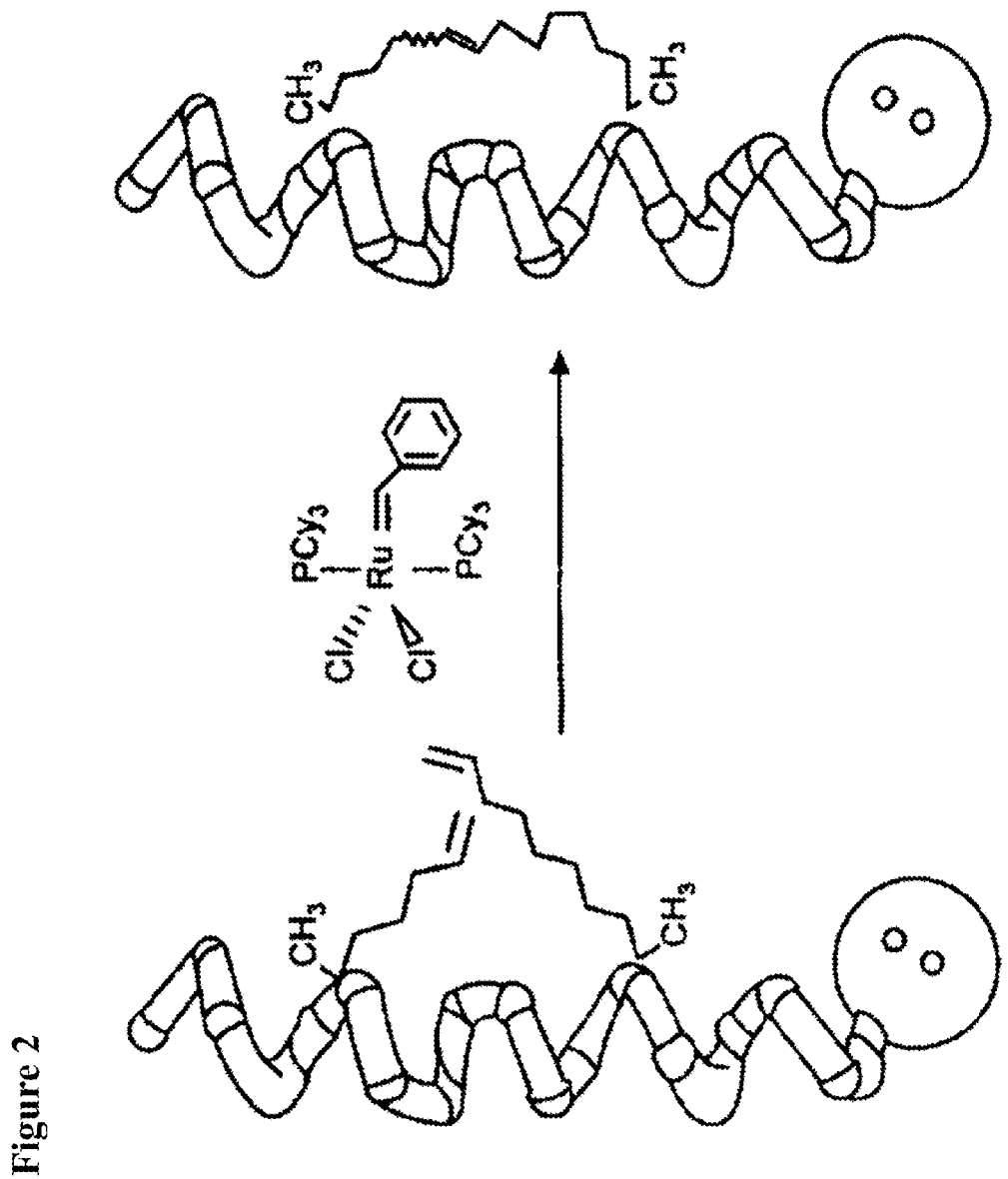
FIG. 2. A stapled peptide formed from two α-methyl,α-alkenyl amino acids using olefin metathesis.

The present invention provides a system for generating large proteins (e.g., greater than approximately 50 amino acid) having crosslinked secondary structural motifs (e.g., α-helices). Proteins prepared by the inventive system include staples or stitches. Stapled peptides, stitched peptides, and methods for their preparation have been previously disclosed in U.S. Pat. No. 7,192,713, published U.S. Patent Application 2006/0008848, international PCT patent application PCT/US08/58575, and published PCT International Applications WO 2005/044839 and WO 2008/061192, each of which is incorporated herein by reference. Stapled or stitched proteins, as described herein, may be useful wherever such crosslinked secondary structural motifs (particularly, a crosslinked α-helix) are advantageous, for example, as a therapeutic agent or a research tool. The stapled or stitched proteins may function as modulators of protein-protein, protein-ligand, or protein-receptor binding interactions. In certain embodiments, these inventive stapled or stitched proteins are useful in the treatment of proliferative, neurological, immunological, endocrinologic, cardiovascular, hematologic, and/or inflammatory diseases, disorders, and/or conditions, and conditions characterized by premature or unwanted cell death. In one aspect, the invention provides IL-13 with a stapled Helix A for use in treating asthma. In another aspect, the invention provides Myc with a staples leucine zipper portion for use in treating a proliferative disease. In another aspect, the stapled portion is not derived from a protein sequence, but instead serves as a functional tag attached to a protein of interest. The functional tag could serve various purposes, such as making the protein cell-permeant, allowing the protein to cross the blood-brain barrier, increasing serum half-life by binding to serum albumin, targeting to bone (Gla-containing peptides), or target to specific cell types (RGD peptide). In certain embodiments, the stapled or stitched peptide functional tag is attached through a non-proteinogenic linker (e.g. polyethylene glycol). In certain embodiments, the stapled or stitched peptide functional tag is attached through a proteinogenic linker. In certain embodiments, the stapled or stitched peptide functional tag is attached at the N-terminal end of the protein. In certain embodiments, the stapled or stitched peptide functional tag is attached at the C-terminal end of the protein.

The stapled or stitched proteins of the current invention are prepared by ligating a stitched or stapled peptide to a protein to form a stapled or stitched protein larger than could practically be prepared using known peptide synthesis methodology. The use of the inventive ligation methodology to prepare stitched or stapled proteins is novel, because the only stapled or stitched peptides that have been reported thus far have been purely synthetic. Solid-phase peptide synthesis is typically limited to a peptide length of about 50 amino acids and does not allow for the synthesis of large protein sequences such as IL-13 or MYC. Although the total chemical synthesis of larger proteins could be done on a proof-of-principle scale, it would be a momumental undertaking and could not conceivably be performed on a multi-kilogram scale necessary to support clinical use. The current invention provides a method for making larger polypeptides or proteins by a semi-synthetic method, allowing for a larger number of amino acids in the sequence. A synthetic stapled or stitched peptide is ligated to a larger protein prepared recombinantly or purified from a natural source.

Aspects of the invention relate to ligating a stitched or stapled bifunctional peptide to a protein. A bifunctional stapled or stitched peptides can tether, or bring together two cellular entities as described in U.S. provisional patent application, U.S. Ser. No. 61/225,191, filed Jul. 13, 2009, which is incorporated herein by reference. One domain of the bifunctional peptide acts as a targeting moiety that binds to a target; the other domain acts as an effector domain to recruit a protein, protein complex, or other biomolecule to the target. In essence, the bifunctional peptide works to bring two proteins or other biomolecules in proximity to one another and in proximity to the ligated protein. The targeting domain, the effector domain, or both domains may be stapled or stitched to stabilize the conformation of the peptide. In certain embodiments, the bifunctional peptides is ligated to a protein. In some embodiments, one domain (effector or targeting domain) is ligated to the protein. In some embodiments, the bifunctional peptide adds functionality to the protein that is ligated to the bifunctional peptide by providing a domain that is capable of recruiting one or more cellular entities (e.g., protein, nucleic acid, organelle). In certain embodiments, bifunctional stapled or stitched peptides of the invention are used to tether any two biomolecules (such as polypeptides) together. A polypeptide can be, for example, a single polypeptide, such as a protein, or can be a complex comprising two or more polypeptides that associate with each other, such as a protein complex. To tether, as used herein, means to bring into close proximity cellular entities (e.g., proteins, nucleic acids, membranes, organelles, etc.). In certain embodiments, when two polypeptides are brought together (or tethered) by a bifunctional stapled peptide of the invention, they might be coming into such close molecular contact that one polypeptide (an "effector" biomolecule) might alter or modify the other polypeptide (a "target" biomolecule).

Method of the Invention

The current invention provides a method of preparing a stapled or stitched protein comprising the steps of providing a stapled or stitched peptide (see FIGS. 2 and 3, respectively), providing a second protein or peptide to which the stapled or stitched peptide is to be ligated, and ligating the stapled or stitched peptide to the second protein or peptide. The peptide may be stitched or stapled before or after the ligation step.

In certain embodiments, a stapled polypeptide of formula (I) is used in accordance with the present invention:

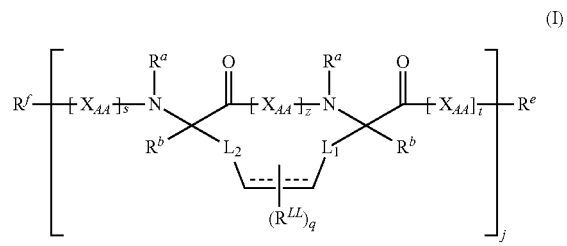

wherein each instance of $L_1$ and $L_2$ is, independently, a bond, cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene;

each instance of $R^a$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; or $R^a$ is a suitable amino protecting group;

each instance of $R^b$ is, independently, a suitable amino acid side chain; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^e$ is, independently, $-R^E$, $-OR^E$, $-N(R^E)_2$, or $-SR^E$, wherein each instance of $R^E$ is, independently, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino, or thiol protecting group; or two $R^E$ groups together form a substituted or unsubstituted 5- to 6-membered heterocyclic or heteroaromatic ring;

each instance of $R^f$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a linker, wherein the linker is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ together form a substituted or unsubstituted 5- to 6-membered heterocyclic or heteroaromatic ring;

each instance of $R^{LL}$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro;

or two adjacent $R^{LL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring;

each instance of $X_{AA}$ is, independently, a natural or unnatural amino acid;

each instance of z is, independently, an integer between 2 to 6;

each instance of j is, independently, an integer between 1 to 10;

each instance of s and t is, independently, an integer between 0 and 100;

each instance of q is, independently, an integer between 0 to 2;

and wherein

========= corresponds to a single or double bond.

In certain embodiments, a stitched polypeptide of the formula (II) is used in accordance with the present invention:

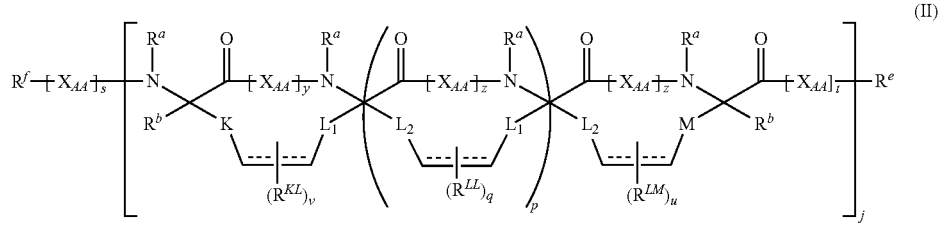

wherein each instance of K, $L_1$, $L_2$, and M, is, independently, a bond, cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene;

each instance of $R^a$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; or $R^a$ is a suitable amino protecting group;

each instance of $R^b$ is, independently, a suitable amino acid side chain; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^e$ is, independently, —$R^E$, —$OR^E$, —$N(R^E)_2$, or —$SR^E$, wherein each instance of $R^E$ is, independently, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino, or thiol protecting group; or two $R^E$ groups together form a substituted or unsubstituted 5- to 6-membered heterocyclic or heteroaromatic ring;

each instance of $R^f$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a linker, wherein the linker is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ together form a substituted or unsubstituted 5- to 6-membered heterocyclic or heteroaromatic ring;

each instance of $R^{KL}$, $R^{LL}$, and $R^{LM}$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro;

or two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; or two adjacent $R^{LM}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring;

each instance of $X_{AA}$ is, independently, a natural or unnatural amino acid;

each instance of y and z is, independently, an integer between 2 to 6;

each instance of j is, independently, an integer between 1 to 10;

each instance of p is, independently, an integer between 0 to 10;

each instance of s and t is, independently, an integer between 0 and 100;

each instance of u, v, and q, is, independently, an integer between 0 to 2;

and wherein

======== corresponds to a single or double bond.

The stiched or stapled peptide may be prepared with the appropriate N- and/or C-terminus for ligating to the protein. In certain embodiments, a stitched or stapled peptide with an N-terminal cysteine residue is ligated to a protein with a C-terminal thioester to form the stapled or stitched protein. In certain other embodiments, a stitched or stapled peptide with a C-terminal thioester is ligated to a protein with an N-terminal cysteine residue to form the stapled or stitched protein.

Figure 27:
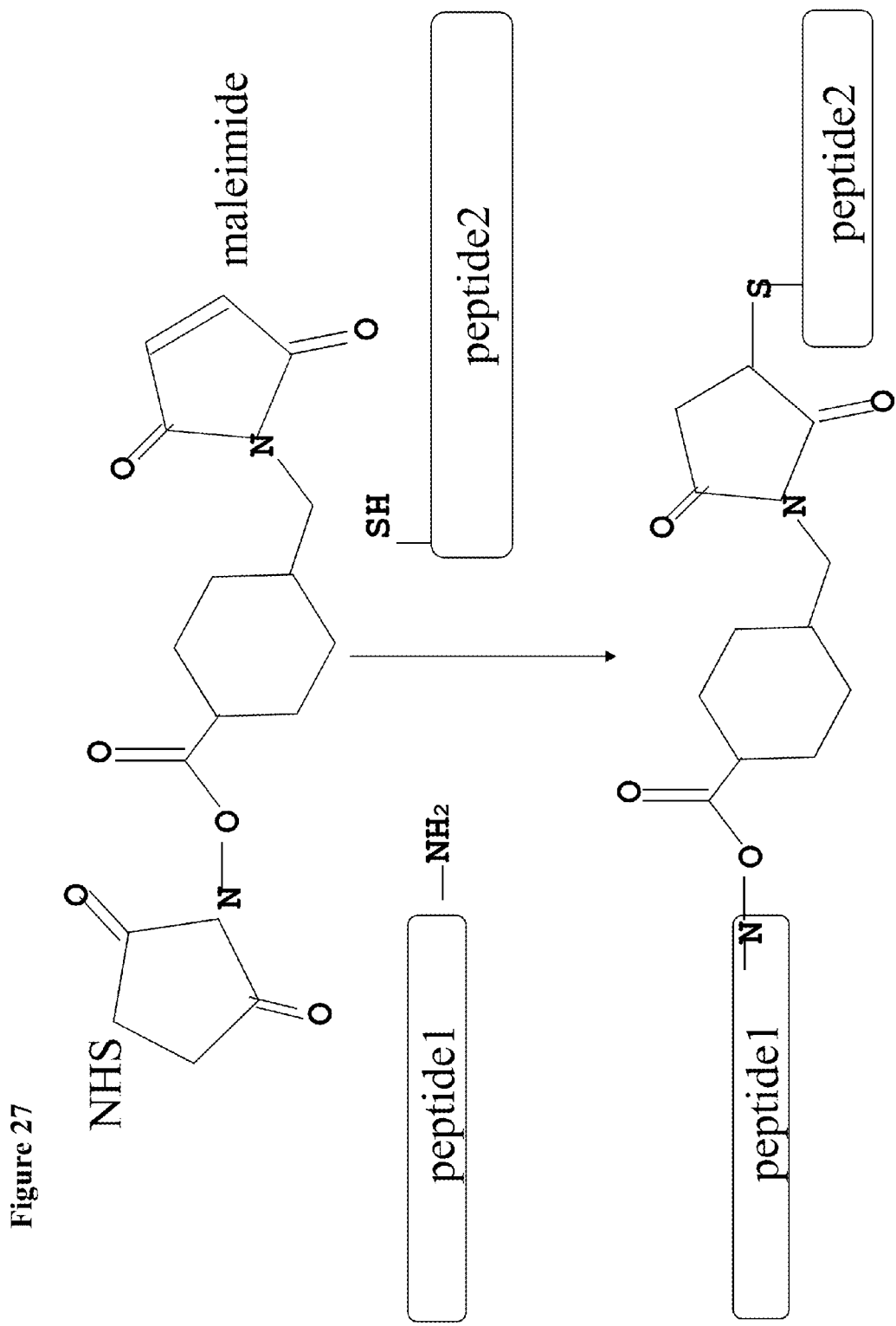
FIG. 27. Non-limiting examples of stapled bifunctional peptides using cross-linkers to join the two peptide domains (targeting domain and effector domain).

In certain embodiments, the stiched or stapled peptide is a bifunctional peptide, as described herein and in U.S. provisional patent application, U.S. Ser. No. 61/225,191, filed Jul. 13, 2009, which is incorporated herein by reference. In certain embodiments, the stapled or stitched bifunctional peptide comprise three building blocks: A-L-E, comprising a targeting domain (A), a linker (L), and an effector domain (E), that are generally arranged as follows:

| A | —L— | E | wherein A and/or E is a stapled or stitched peptide, and L is a linker; wherein A is a targeting domain and E is an effector domain (see, as a non-limiting example, FIG. 27). A and E are targeting or effector domains, that are sequences of amino acids that may or may not be stapled that specifically associate or bind to polypeptides, such as a target biomolecule or an effector biomolecule. Any part of the peptide A may be linked to any part of the peptide E through the linker L. In certain embodiments, the linkage is N-terminus to N-terminus. In certain embodiments, the linkage is C-terminus to N-terminus. In certain embodiments, the linkage is C-terminus to C-terminus. In still other embodiments, the linkage may be through interior amino acids of one or both peptides. As will be appreciated by one on skill in the art, the linkage is typically positioned in such a way as to avoid interfering with the binding activity of the peptide. The linkage may also be positioned in such a way to avoid interfering with the stapling of the peptide.

In certain embodiments, where A is the targeting domain and specifically associates or binds to a target, E is the effector domain and specifically associates or binds an effector biomolecule capable of modifying the target bound or associated with the targeting domain A. L is a chemical linker that covalently links A and E. The linker L may be aliphatic or heteroaliphatic. In certain embodiments, linker L is 1-50 atoms, in length, and may be optionally substituted. In certain embodiments, linker L is 1-25 atoms, in length, and may be optionally substituted.

A and E can have any length, that is they may comprise any number of amino acids. The number of amino acids can be four or more, 5, 6, 7, 8, 9, 10, 11, 12, 13, 14, 15, 16, 17, 18, 19, 20, 25, 30, 35, 40, 45, 50, 100 or more, or any number of amino acids in between 4 and 100. A and E can comprise a number of amino acids that is the minimal number of amino acids sufficient to specifically bind or associate with either the target or the effector biomolecule. The amino acid sequence of one or both of the domains may be substantially similar to or homologous to a known peptide.

In certain embodiments, one or both of peptides A and E is an alpha-helical polypeptide. In certain embodiments, peptide A is substantially alpha-helical. In certain embodiments, peptide E is substantially alpha-helical. As used herein, the phrase "substantially alpha-helical" refers to a polypeptide adopting, on average, backbone ($\phi$, $\psi$) dihedral angles in a range from about (−90°, −15°) to about (−35°, −70°). Alternatively, the phrase "substantially alpha-helical" refers to a polypeptide adopting dihedral angles such that the $\psi$ dihedral angle of one residue and the $\phi$ dihedral angle of the next residue sums, on average, about −80° to about −125°. In certain embodiments, the polypeptide adopts dihedral angles such that the $\psi$ dihedral angle of one residue and the $\phi$ dihedral angle of the next residue sums, on average, about −100° to about −110°. In certain embodiments, the polypeptide adopts dihedral angles such that the $\psi$ dihedral angle of one residue and the $\phi$ dihedral angle of the next residue sums, on average, about −105°. Furthermore, the phrase "substantially alpha-helical" may also refer to a polypeptide having at least 50%, 60%, 70%, 80%, 90%, or 95% of the amino acids provided in the polypeptide chain in an alpha-helical conformation, or with dihedral angles as specified herein. Confirmation of a polypeptide's alpha-helical secondary structure may be ascertained by known analytical techniques, such as x-ray crystallography, electron crystallography, fiber diffraction, fluorescence anisotropy, circular dichroism (CD), and nuclear magnetic resonance spectroscopy.

Bifunctional peptides may be used to tether two cellular entities together. When ligated to a protein, the bifunctional peptide brings into proximity the two cellular entities with the ligated protein. In certain embodiments, by tethering two cellular entities, it is desired that one entity brings about a change in the other entity or the ligated protein. One entity that brings about the change in the other entity is an effector biomolecule that modifies the other entity or ligated protein, which is the target. The modification of the target biomolecule changes some characteristic (e.g., biological activity) of the target. In some embodiments, by tethering two cellular entities, it is desired that the two entity are essentially irreversibly tethered together. For example, certain effector biomolecules may associate with a target or dissociate from a target naturally upon certain stimuli or molecular signals. Bifunctional peptides of the invention may be used to tether two cellular entities together irreversibly so that they do not dissociate upon such stimuli or other signals and remain associated. The effector biomolecule, for example, can be a cellular inhibitor of the target, or a particular molecular complex, that associates with the target to keep it in a certain intracellular localization, e.g. cytosolic or nuclear. In other embodiments bifunctional peptides can be used to tether biomolecules together that would only associate naturally upon certain stimuli or molecular signals, in the absence of such stimuli. In other embodiments, biomolecules can be tethered together that do not naturally associate with each other. "Naturally" as used herein means in a cellular context under physiological conditions, which include diseased conditions.

In certain embodiments, bifunctional stapled peptides can be used to alter one or more characteristics of the target or ligated protein. In certain embodiments, the characteristics of the target or ligated protein are altered in such a way that this alteration affects cell fate and/or cell behavior. In certain embodiments, changes in cell fate or cell behavior as a result of changes in one or more characteristics of the target affect the disease state of a subject, such as a mammal, for example, a human. In certain embodiments, bifunctional stapled peptides ligated to a protein can be used to treat disease. In certain embodiments, bifunctional stapled peptides ligated to a protein can be used to probe or elucidate biological pathways in research. The probing of a biological pathway can be performed both in vitro such as in cell or tissue culture, or in vivo, such as in an animal, e.g., humans, mice, rats, hamsters, fish, or primates. In some embodiments, the two cellular entities are polypeptides, such as proteins and associated protein complexes. In certain embodiments, alterations or modifications of one entity (the target biomolecule) can be the result of an enzymatic activity of the other entity (the effector molecule).

Bifunctional peptides, their synthesis, their structures, and their functions are described in detail in U.S. provisional patent application, U.S. Ser. No. 61/225,191, filed Jul. 13, 2009, the content of which is incorporated herein in its entirety.

In certain embodiments, an unstapled or unstitched peptide containing residues amenable to stapling or stitching is ligated to a protein. After ligation, the stapling or stitching step is performed to provide the stapled or stitched protein.

In certain embodiments, the ligation partner protein for the stapled or stitched peptide portion is produced by recombinant protein expression. The protein may be produced in bacterial, fungal, plant, or animal cells. In certain embodiments, the protein is produced in E. coli. In certain embodiments, the protein is produced in mammalian cells. The expression system used to produce the protein may be chosen based on the system's ability to provide desired post-translational modifications of the protein (e.g., glycosylation). In other embodiments, the protein that serves as the ligation partner is purified from natural sources. For methods of protein expression and purification, see Maniatis, *Molecular Cloning: A Laboratory Manual*, Cold Spring Harbor Laboratory, New York, 1982. In certain other embodiments, the ligation partner is a polypeptide that has been chemically synthesized by solution-phase or solid-phase peptide synthesis, as described herein. In still other embodiments, the protein that serves as the ligation partner may be obtained by other means (e.g., the protein may be purchased from a commercial source).

The protein ligation partner may be produced or subsequently modified to have the appropriate N- or C-terminus for ligation to the stapled or stitched peptide segment. For example, the protein may be enzymatically modified, proteolysed, or chemically modified to yield the desired termini for ligation. In certain embodiments, the protein ligation partner is expressed as a fusion construct with an intein so as to create a C-terminal thioester after protein expression in E. coli or other organism. The protein thioester can then be ligated to a stapled or stitched peptide containing an N-terminal cysteine using expressed protein ligation to generate the stapled or stitched protein. Alternatively, the protein thioester can be ligated to an unstapled or unstitched peptide containing alkenyl or dialkenyl residues suitable for stapling or stitching, and also containing an N-terminal cysteine, and then the protein can be stapled or stitched.

In certain embodiments, the protein ligation partner is expressed so as to contain an N-terminal methionine-cysteine sequence, which can then be processed by the E. coli biosynthetic machinery to yield an N-terminal cysteine. The protein can then be ligated to a stapled or stitched peptide containing a C-terminal thioester to generate the stapled or stitched protein. Alternatively, the protein can be ligated to an unstapled or unstitched peptide containing alkenyl or dialkenyl residues suitable for stapling or stitching, and also containing a C-terminal thioester, and then the protein can be stapled or stitched.

An alternative way to produce proteins containing an N-terminal cysteine is to employ specific proteolytic degradation. A recombinant protein can be designed with a cleavage site that is upstream of a cysteine residue. Once the protein is cleaved by a protease, an N-terminal cysteine is unveiled. Exemplary proteases include Factor Xa, Tobacco Etch Virus protease, enterokinase, trypsin, chymotrypsin, pepsin, papain, elastase, thrombin, plasmin, furin, and ubiquitin C-terminal hydrolase. Protease with specific recognition sequences are particularly useful in the present invention. The recognition sequence of the protease used is placed upstream of the cleavage to produce the desired N-terminus for ligation.

In certain embodiments, the C-terminal thioester of the stapled or stitched peptide is furnished by cleavage from a thioester resin.

In certain embodiments, the inventive method is used to replace a helical portion of an existing protein with a stapled or stitched helical portion. A helix-swapping scheme can be used (see FIG. 1). A proteolytic cleavage site, immediately abutting a cysteine residue, is introduced into a section of the protein occurring between the helix of interest and the rest of the protein. The resulting construct is subjected to proteolytic cleavage, thereby removing the helical portion and providing the rest of the protein with an N-terminal cysteine residue. The protein is then ligated to a stapled or stitched peptide containing a C-terminal thioester to give the stabilized version of the desired protein. The above steps may be performed in a folded or unfolded state. If the steps are performed in the unfolded state, the protein may be re-folded after the proteolysis or after the ligation step.

Figure 4:
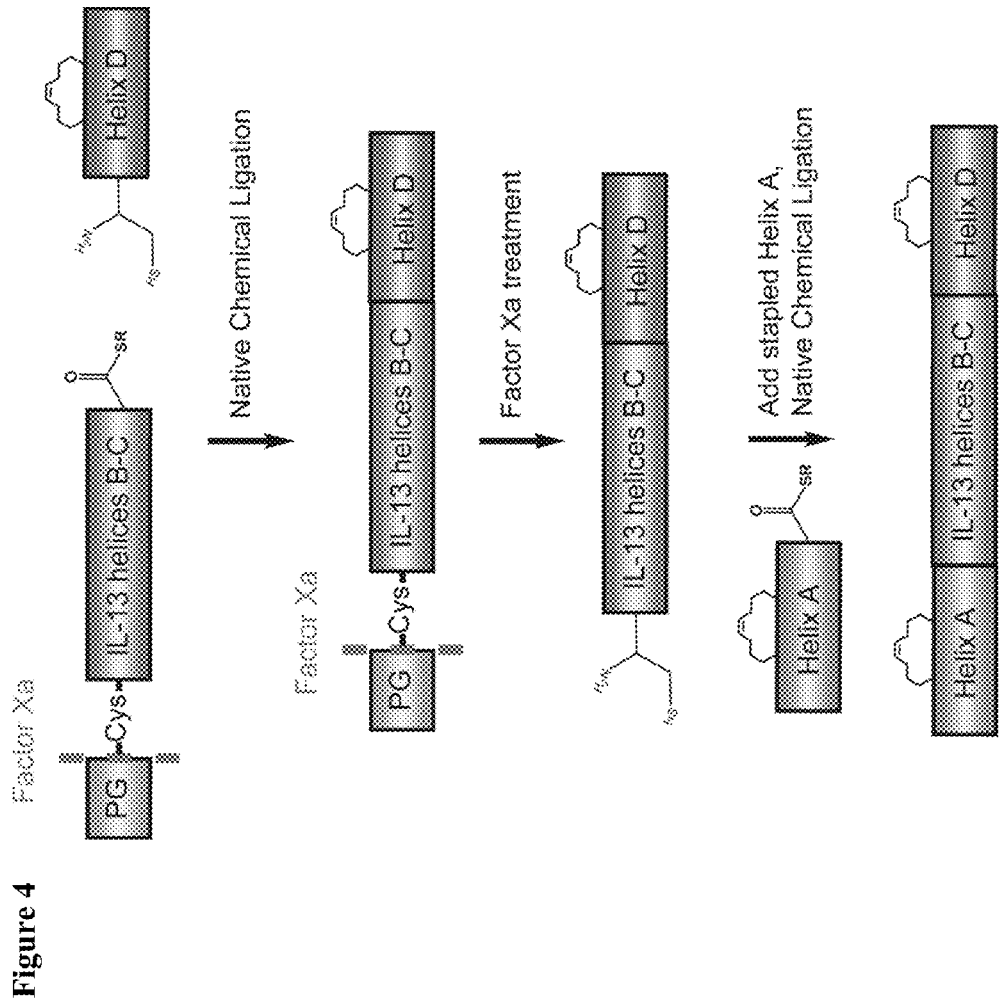
FIG. 4. Synthetic design of IL-13 containing stapled Helices A and D. Helices A and D can be made synthetically to contain either stapled/stitched versions. Helices B-C will be recombinantly expressed to contain a C-terminal thioester as well as an N-terminal cysteine. The N-terminal cysteine will be protected by the flanking peptides sequence (PG=protecting group). After Helix D is attached to the recombinant protein component, the PG will be removed by Factor Xa treatment to expose an N-terminal cysteine. Synthetic Helix A will subsequently be attached. Two synthetically modified components can block interactions with one receptor (IL-4Rα and Helix A) while stabilizing interactions with the other receptor component (IL-13Rα1 and Helix D).

In certain embodiments, two stapled or stitched peptides are ligated to a recombinantly expressed protein (see FIG. 4). The recombinantly expressed protein is expressed as a fusion construct with an intein so as to create a C-terminal thioester after protein expression in prokaryotic or eukaryotic cells. The recombinantly expressed protein also contains a protease cleavage site immediately followed by a cysteine residue. The protein thioester can then be ligated to a stapled or stitched peptide containing an N-terminal cysteine using expressed protein ligation to generate the stapled or stitched protein. The N-terminal cysteine of the stapled or stitched protein is exposed by proteolytic degradation, then a stapled or stitched peptide containing a C-terminal thioester can be ligated to the stapled or stitched protein, yielding a protein containing two stabilized helical portions.

As would be appreciated by one of skill in the art, the inventive method may be accomplished in any number of ways without departing from the claimed invention.

Stapled and Stitched Peptides

The peptide segment of the protein to be modified typically includes a secondary structural motif to be stapled or stitched. Exemplary secondary structural motifs of polypeptides and proteins that can be stabilized or modified include, but are not limited to, an α-helix, $3_{10}$ helix, π helix, and type II helices (e.g., left-handed helices). In certain embodiments, the stapled or stitched secondary structural motif of the inventive protein is an α-helix. In certain embodiments, the stapled or stitched secondary structural motif is a β-sheet. In certain embodiments, the stapled or stitched secondary structural motif is a β-hairpin. In certain embodiments, one portion of the stapled or stitched peptide has a helical portion and a non-helical portion. One or more secondary structural motifs may be stabilized in an inventive polypeptide using protein stapling or stitching. For example, a protein may comprise more than one α-helical peptide segment which is stapled and/or stitched.

In certain embodiments, a portion of the crosslinked protein is derived from a stapled peptide. In other embodiments, a portion of the crosslinked protein is derived from a stitched peptide. Stapled peptides, stitched peptides, and methods for their preparation have been previously disclosed (see U.S. Pat. No. 7,192,713; U.S. Patent Application 2006/0008848; and PCT International Applications WO 2005/044839 and WO 2008/061192; each of which is incorporated herein by reference). In general, the synthesis of these stapled or stitched structures involves synthesizing a peptide from a selected sequence of natural or non-natural amino acids, wherein said peptide comprises at least two reactive moieties capable of undergoing a bond forming reaction; and contacting said peptide with a reagent to generate at least one crosslinker. In certain embodiments, the stapled or stitched peptide is an α-helix structure having at least one crosslinker. In certain embodiments, an olefin metathesis reaction is utilized to generate the stapled or stitched α-helical structure. The method of using an olefin metathesis reaction to form the crosslink comprises synthesizing a peptide from a selected sequence of natural or non-natural amino acids, wherein said peptide comprises at least two alkenyl amino acids capable of undergoing an olefin metathesis reaction, or comprises at least one dialkenyl amino acid and at least two alkenyl amino acids capable of undergoing olefin metathesis reactions; and contacting said peptide with a metathesis catalyst to generate at least one crosslinker and to effect stabilization of an α-helix structure. In certain embodiments, at least two alkenyl amino acids are incorporated into the peptide synthesis to generate at least one crosslinker, thereby generating a stapled peptide (see FIG. 2). In other embodiments, at least two alkenyl amino acids and at least one dialkenyl amino acid are incorporate to generate at least two crosslinkers originating from the same amino acid, thereby generating a stitched peptide (see FIG. 3). Alternatively, any combination of dialkenyl amino acids and alkenyl amino acids may be incorporated into the peptide sequence to generate desired crosslinked structures. It will also be appreciated that in certain embodiments, one or more of either of these crosslinker motifs can be incorporated into a desired helical structure.

Certain embodiments of the novel proteins having crosslinked secondary structures will be described below; however, this description is not meant to limit the scope of the present invention. Rather, it will be appreciated that all equivalents are intended to be included within the scope of the invention. Although the following discussion and description of the method of the present invention will focus on α-helices, it will be appreciated that the methods of the present invention can be applied to crosslink other peptide secondary structures as well.

Figure 3:
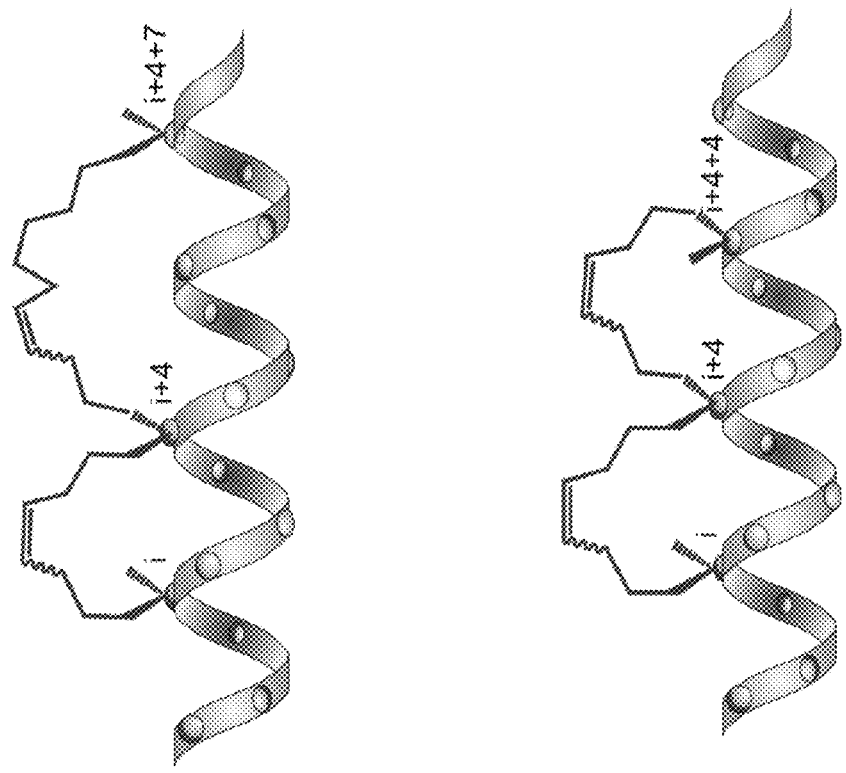
FIG. 3. Examples of stitched peptides.

The synthesis of novel α-helix structures first involves the selection of a desired sequence of amino acids. As one of ordinary skill in the art will realize, the number, stereochemistry, and type of amino acid structures (natural or non-natural) selected will depend upon the size of the α-helix to be prepared, the desired sequence, the ability of the particular amino acids to adopt an α-helix structural motif, and any particular motifs that are desirable to mimic (for example, Helix A of IL-13). Furthermore, as mentioned above, for the synthesis of the stabilized α-helices, in one embodiment, at least two of the desired amino acids to be utilized in the synthesis are alkenyl amino acids of Formula B capable of undergoing olefin metathesis reactions to generate at least one crosslinker, as shown in FIG. 2. In another embodiment, the peptide to be synthesized incorporates at least two alkenyl amino acids of Formula B and at least one dialkenyl amino acid of Formula A to generate at least two crosslinkers originating from the same amino acid moiety, as shown in FIG. 3. It will be appreciated, however, that the number of crosslinking moieties is not limited to one or two, as described above; rather the number of crosslinking moieties utilized can be varied with the length of the α-helix as desired, and as compatible with the desired structure to be generated.

In certain embodiments, an amino acid of Formula A is used in accordance with the invention:

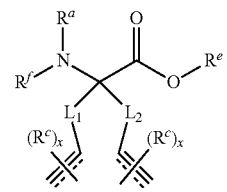

wherein $L_1$, $L_2$, $R^a$, $R^e$, $R^f$, $R^c$, x, and ═══ are defined herein.

In certain embodiments, an amino acid of Formula B is used in accordance with the invention:

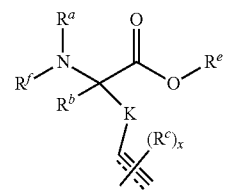

wherein K, $R^a$, $R^b$, $R^e$, $R^f$, $R^c$, x, and ═══ are defined herein.

In certain embodiments, α-methyl,α-alkenyl or α-hydro, α-alkenyl amino acids are utilized as precursors for crosslinker formation. As one of ordinary skill in the art would realize, a variety of homoallyl reagents can be utilized to generate amino acids having different lengths of olefin chains. It will also be appreciated that these olefin chains can also be further functionalized with moities including, but not limited to, branched or linear alkyl moieties, hydroxyl moieties, thiol moieties, amines, carboxyl moieties, and substituted or unsubstituted aryl moieties, to name a few. In certain embodiments, the amino acid comprises a terminal alkenyl moiety.

Exemplary α-Alkenyl Amino Acids

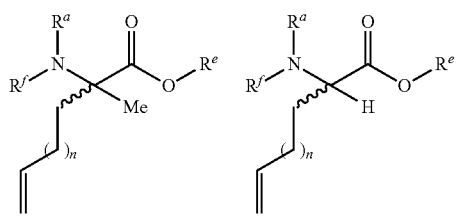

wherein n is an integer between 0 and 12, inclusive. In certain embodiments, n is an integer between 0 and 10, inclusive. In certain embodiments, n is an integer between 0 and 8, inclusive. In certain embodiments, n is an integer between 0 and 6, inclusive. In certain embodiments, n is an integer between 0 and 4, inclusive. In certain embodiments, the α-alkenyl amino acid is of one of the formulae:
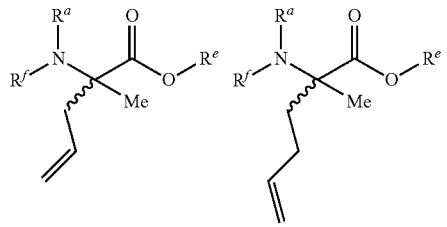
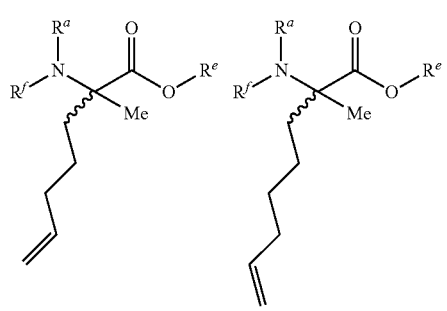
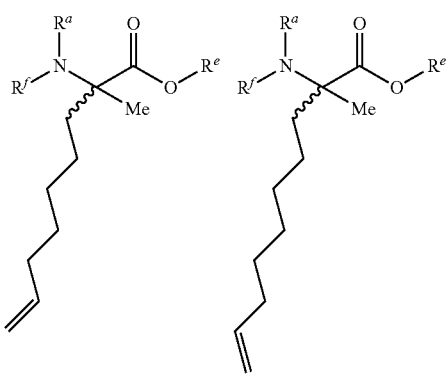
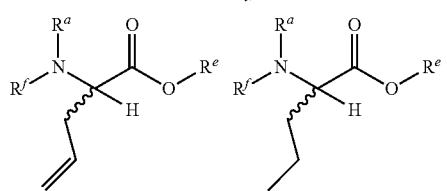
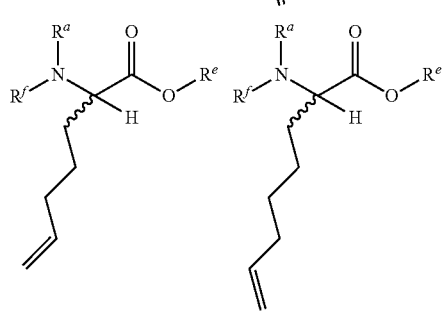
-continued
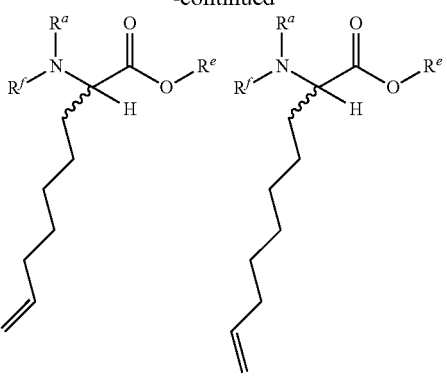
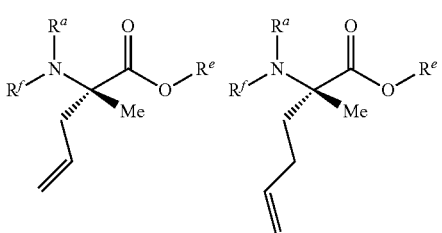
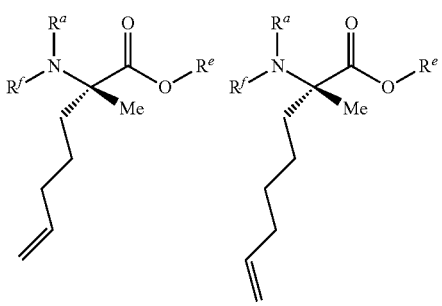
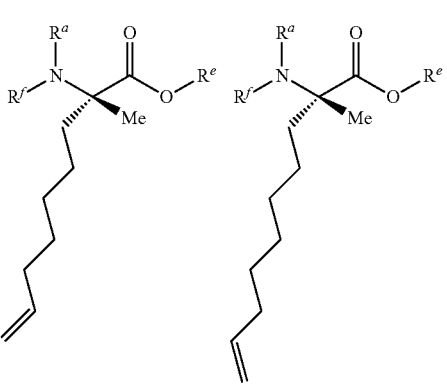
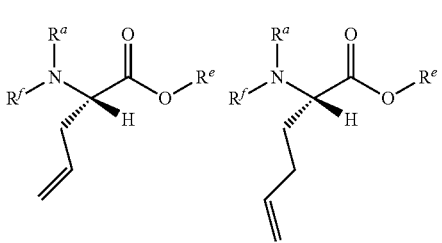

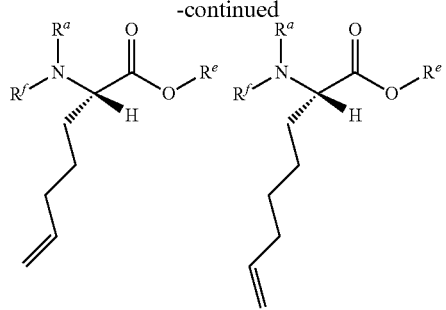
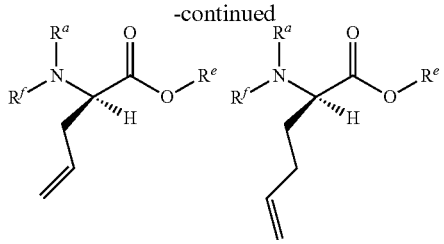
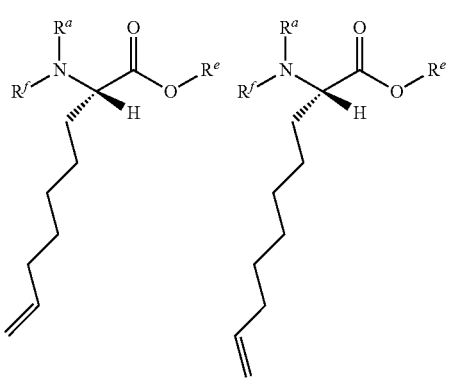
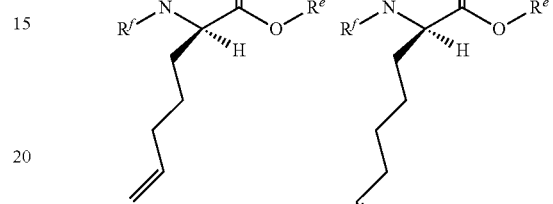
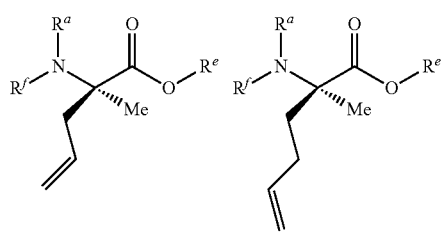
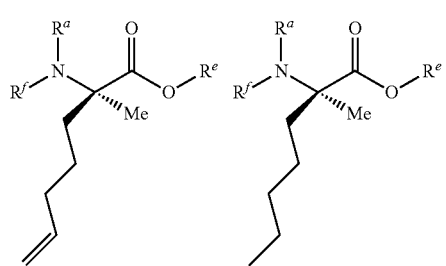
As discussed above, the α-helices of the invention may also contain two crosslinking units originating from one amino acid. This is facilitated by the synthesis of an α,α-dialkenyl amino acid, from which two olefin metathesis reactions can originate, and is preferably incorporated into the desired peptide synthesis.
Exemplary α,α-Dialkenyl Amino Acids
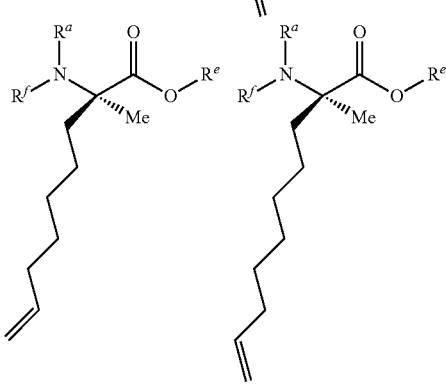
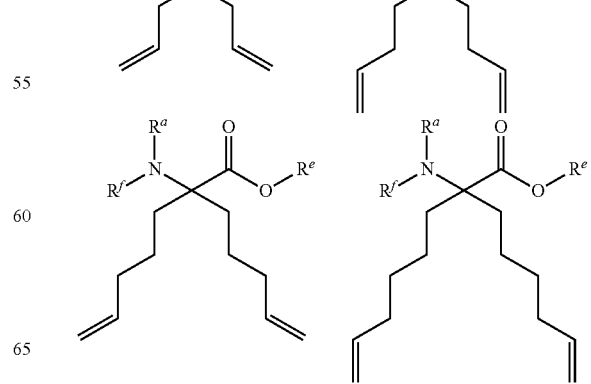

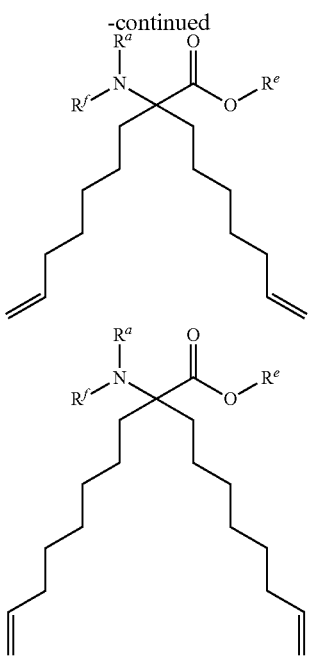

Although α-methyl,α-alkenyl amino acids and α,α-dialkenyl amino acids are preferably utilized to generate the crosslinking moieties as discussed above using an olefin metathesis reaction, the other amino acids utilized in the peptide synthesis may be selected from any standard or nonstandard amino acids. The standard amino acids include glycine, alanine, valine, leucine, isoleucine, proline, phenylalanine, tryptophan, methionine, serine, threonine, cysteine, tyrosine, asparagine, glutamine, aspartic acid, glutamic acid, lysine, arginine, and histidine. There are over 700 known nonstandard amino acids, any of which may be included in the peptide precursors for use in the present invention. See for example, Hunt, *The Non-Protein Amino Acids: In Chemistry and Biochemistry of the Amino Acids*, edited by G. C. Barrett, Chapman and Hall, 1985. Some examples of nonstandard amino acids are β-alanine, D-alanine, 4-hydroxyproline, desmosine, D-glutamic acid, γ-aminobutyric acid, β-cyanoalanine, norvaline, 4-(E)-butenyl-4(R)-methyl-N-methyl-L-threonine, N-methyl-L-leucine, and statine. Additionally, the same amino acids suitable for use in the present invention may be derivatized to include amino acid residues that are hydroxylated, phosphorylated, sulfonated, and glycosylated, to name a few. Additionally, these amino acids may include functional groups including, but not limited to, alcohol, thiol, ketone, aldehyde, ester, ether, amine, imine, amide, nitro acid, carboxylic acid, disulfide, carbonate, carboalkoxy acid, isocyanate, carbodiimide, carboalkoxy, and halogen functional groups. It will be appreciated by one of ordinary skill in the art, however, that certain amino acids are capable of promoting formation of α-helix structures or other desired secondary structures, and thus these amino acids are particularly useful in the present invention, depending on the desired secondary structure to be generated. For a detailed discussion of helix propensities studied in various substitution experiments, see Scholtz and Baldwin, the entire contents of which are incorporated herein by reference. Furthermore, as discussed above, it may be desirable to mimic an existing protein α-helical structure, or other secondary structure, having the crosslinking moieties incorporated therein according to the method of the present invention.

Crosslinks can be incorporated across one (i, i+3 or i, i+4) and/or two turns (i, i+7) of an α-helix. In certain embodiments, the peptide only includes crosslinks across one turn(s) of the helix. In certain embodiments, the peptide includes crosslinks across one and two turns of the helix. In certain embodiments, a staple is incorporated across one turn of a helix using (R)-2-amino-2-methylhept-6-enoic acid in both the i and i+4 positions. In other embodiments, a staple is incorporated across one turn of a helix using (S)-2-amino-2-methylhept-6-enoic acid in both the i and i+4 positions. In certain embodiments, a staple is incorporated across two turns of a helix using (R)-2-amino-2-methylhept-6-enoic acid in the i position and (S)-2-amino-2-methyldec-9-enoic acid in the i+7 position. In other embodiments, a staple is incorporated across two turns of a helix using (S)-2-amino-2-methylhept-6-enoic acid in the i position and (R)-2-amino-2-methyldec-9-enoic acid in the i+7 position. In certain other embodiments, a staple is incorporated across two turns of a helix using (R)-2-amino-2-methyldec-9-enoic acid in the i position and (S)-2-amino-2-methylhept-6-enoic acid in the i+7 position. In certain other embodiments, a staple is incorporated across two turns of a helix using (S)-2-amino-2-methyldec-9-enoic acid in the i position and (R)-2-amino-2-methylhept-6-enoic acid in the i+7 position.

It is important that when designing crosslinking residues into a helical portion of the protein that the crosslinkers do not interfere with any important interactions that the protein may make with other biomolecules (e.g., proteins, nucleic acids, lipids, sugars, etc.). The design requires a strategy based on any structural information available (e.g., crystal structure, mutagenesis studies, or homology models) to place the crosslinkers on the appropriate portion of the helix, out of the way of crucial interactions.

In certain embodiments, the α,α-dialkenyl residue used in a stitched peptide is 2-amino-2-(pent-4-enyl)hept-6-enoic acid, also known as bispentenyl glycine. Bispentylglycine can be stitched with α-alkenyl residues of either R or S stereochemistry across either one or two turns of a helix. In certain embodiments, bispentenylglycine in the i position is stitched with 2-amino-2-methylhept-6-enoic acid in the i−4 position. In certain embodiments, bispentenyl glycine is stitched with 2-amino-2-methylhept-6-enoic acid in the i+4 position. In certain embodiments, bispentenyl glycine is stitched with 2-amino-2-methyldec-9-enoic acid in the i−7 position. In certain embodiments, bispentenyl glycine is stitched with 2-amino-2-methyldec-9-enoic acid in the i+7 position. In certain embodiments, two or more bispentyl glycine residues are incorporated to give three or more stitches.

Once the sequence of amino acids is selected, synthesis of the inventive polypeptide can be achieved using standard peptide synthesis methodology. Formation of peptide bonds and polypeptide synthesis are techniques well-known to one skilled in the art, and encompass both solid phase and solution phase methods; see generally, Bodanszky and Bodanszky, *The Practice of Peptide Synthesis*, Springer-Verlag, Berlin, 1984; Atherton and Sheppard, *Solid Phase Peptide Synthesis: A Practical Approach*, IRL Press at Oxford University Press Oxford, England, 1989, and Stewart and Young, *Solid phase Peptide Synthesis,* 2nd edition, Pierce Chemical Company, Rockford, 1984, the entire contents of each of which are incorporated herein by reference. In both solution phase and solid phase techniques, the choice of the protecting groups must be considered, as well as the specific coupling techniques to be utilized. For a detailed discussion of peptide synthesis techniques for solution phase and solid phase reactions, see, *Bioorganic chemistry: Pep-*

*tides and Proteins*, Hecht, Oxford University Press, New York: 1998, the entire contents of which are incorporated herein by reference.

In certain embodiments, the method comprises a solution phase synthesis of an inventive polypeptide. Solution phase synthesis, as mentioned above, is a well-known technique for the construction of polypeptides. An exemplary solution phase synthesis comprises the steps of: (1) providing an amino acid protected at the N-terminus with a suitable amino protecting group; (2) providing an amino acid protected at the C-terminus with a suitable carboxylic acid protecting group; (3) coupling the N-protected amino acid to the C-protected amino acid; (4) deprotecting the product of the coupling reaction; and (5) repeating steps (3) to (4) until a desired polypeptide sequence is obtained, wherein at least two of the amino acids coupled at any of the above steps each comprise at least one terminally unsaturated amino acid sidechain. During the course of the above synthesis, various parameters can be varied, including, but not limited to, placement of amino acids with terminally unsaturated side chains, stereochemistry of amino acids, terminally unsaturated side chain length and functionality, and amino acid residues utilized.

In certain embodiments, the method comprises a solid phase synthesis of an inventive polypeptide. Solid phase synthesis, as mentioned above, is a well-known technique for the construction of polypeptides. An exemplary solid phase synthesis comprises the steps of: (1) providing a resin-bound amino acid; (2) deprotecting the resin bound amino acid; (3) coupling an amino acid to the deprotected resin-bound amino acid; (4) repeating steps (2) and (3) until a desired peptide is obtained, wherein at least two of the amino acids coupled at any of the above steps each comprise at least one terminally unsaturated amino acid sidechain. During the course of the above synthesis, various parameters can be varied, including, but not limited to placement of amino acids with terminally unsaturated side chains, stereochemistry of amino acids, terminally unsaturated side chain length and functionality, and amino acid residues utilized.

After a desired peptide is synthesized using an appropriate technique, in one embodiment the peptide is contacted with a specific reagent (e.g., an olefin metathesis catalyst) to promote carbon-carbon bond formation, thereby forming the crosslinker. In one particular embodiment, a metathesis catalyst is utilized to effect one or more olefin metathesis reactions and subsequent generation of a crosslinker to stabilize an α-helix or other desired secondary structure. One of ordinary skill in the art will realize that a variety of metathesis catalysts can be utilized in the present invention. Selection of a particular catalyst will vary with the reaction condition utilized and the functional groups present in the particular peptide. Exemplary catalysts include, but are not limited to stabilized, late transition metal carbene catalysts, most preferably Ru and Os metal centers having a +2 oxidation state, an electron count of 16, and pentacoordinated. One of ordinary skill in the art will realize that other appropriate olefin metathesis catalysts may be utilized. For an excellent discussion of metathesis reactions, see Grubbs et al., "Ring Closing Metathesis and Related Processes in Organic Synthesis," Acc. Chem. Res. 1995, 28, 446-452, and U.S. Pat. No. 5,811,515, each of which is incorporated herein by reference.

After formation of the alkene crosslinker via olefin metathesis, in certain embodiments the double bond may be reduced to give an alkane crosslinker. In certain embodiments, the double bond may be functionalized to add a solubilizing group, biomolecule, targeting moiety, or a drug.

It will also be appreciated that in addition to olefin metathesis catalysts, other reagents capable of promoting bond formation (i.e., crosslink formation) can also be utilized. In certain embodiments, the reagent is capable of promoting C—C bond formation. For example, other reactions that can be utilized include, but are not limited to palladium coupling reactions, transition metal catalyzed cross coupling reactions, pinacol couplings (terminal aldehydes), hydrozirconation (terminal alkynes), nucleophilic addition reactions, and NHK (Nozaki-Hiyama-Kishi) Furstner et al., *J. Am. Chem. Soc.* 1996, 118, 12349) coupling reactions. Thus, the appropriate reactive moieties (alkene, alkyne, aldehyde, etc.) are first incorporated into desired amino acids or unnatural amino acids, and then the peptide is subjected to reaction conditions to effect carbon-carbon bond formation which results in the formation of a crosslinker and subsequent stabilization of a desired secondary structure. The reagent may also promote C—O, C—N, S—S, C—S, or other bond formation.

In certain embodiments, the peptide to be stapled or stitched is synthesized by solid-phase peptide synthesis, then stapled or stitched while attached to the resin, then cleaved from the resin to give the stapled or stitched peptide. In other embodiments, the peptide to be stapled or stitched is synthesized by solid-phase peptide synthesis, cleaved from the resin, then stapled or stitched in solution. In certain other embodiments, the peptide to be stapled or stitched is synthesized by solution-phase peptide synthesis, purified as necessary, then stapled or stitched in solution. In certain embodiments, the unstapled or unstitched peptide is used in the ligation reaction, and the peptide is subsequently staples or stitched after ligation to the protein.

Figure 5:
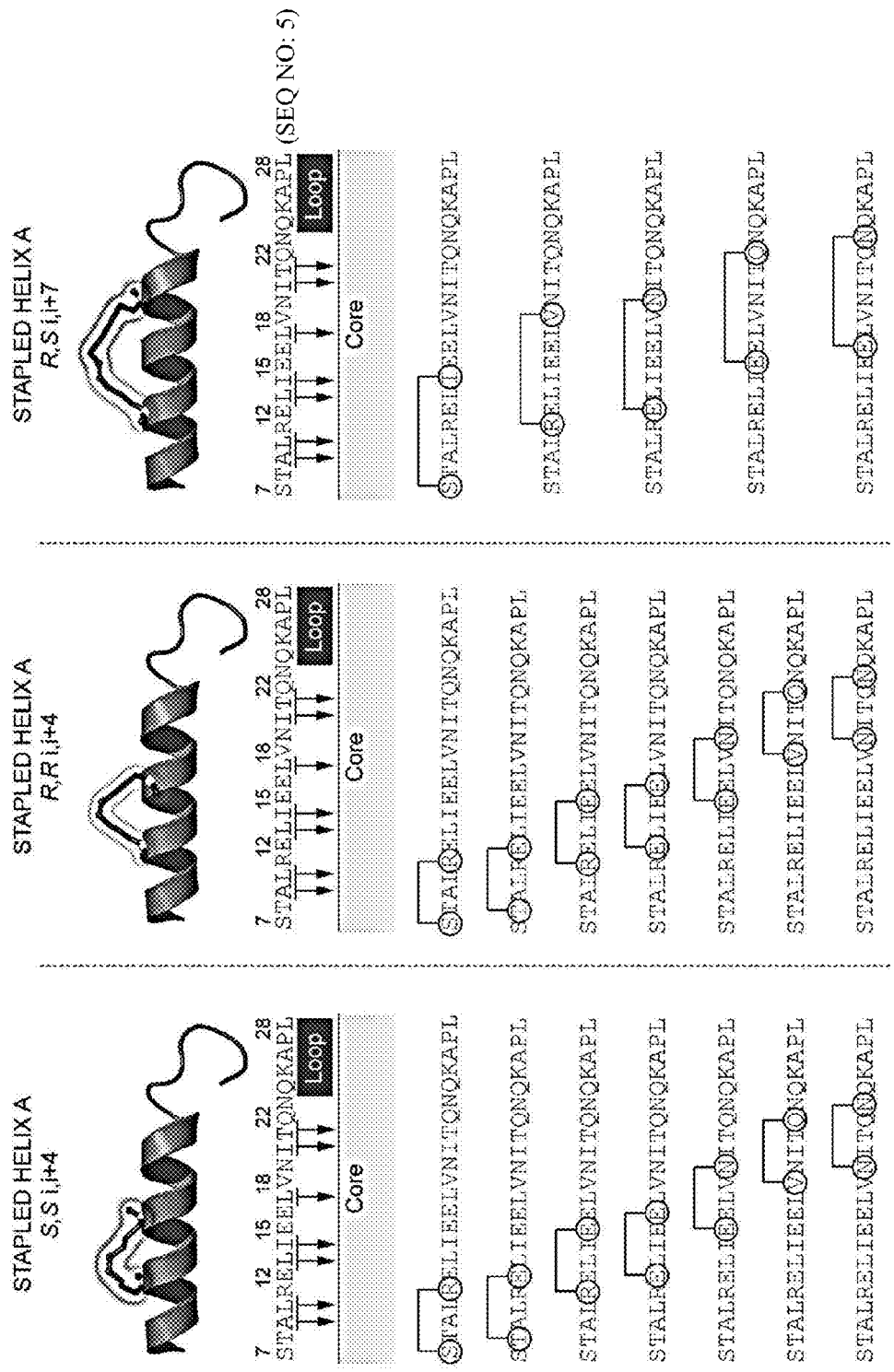
FIG. 5. The library of stapled Helix-A peptides to be used in the construction of stapled IL-13 proteins. All peptides will be synthesized as a C-terminal thioester. Residues that contribute to core packing interactions (denoted by arrows) will not be used for staple incorporation. All members of the left panel contain the S,S-configured i, i+4 staple; middle, R,R-configured i, i+4 staple; right, R,S-configured i, i+7 staple.

In certain embodiments, a derivative of helix A of IL-13 containing α-methyl,α-alkenyl residues is synthesized on 3-S-trityl mercaptopropionyl resin using the Boc procedure for solid phase synthesis (see (1990) *Introduction to Cleavage Techniques*, Applied Biosystems, Inc., Foster City). The peptide is stapled using benzylidene-bis(tricyclohexylphosphine)dichlororuthenium (also known as Grubbs' $1^{st}$ generation catalyst) as the olefin metathesis catalyst, and then the peptide is cleaved from the resin with HF to yield a C-terminal thioester (see FIG. 5).

In certain embodiments, linkers may be used to link peptide domains of the invention to large proteins or to link the targeting domain and the effector domain of a stapled or stitched bifunctional peptide. The linker may be as simple as a covalent bond, or it may be a polymeric linker many atoms in length. In certain embodiments, the linker is a polpeptide or based on amino acids. In other embodiments, the linker is not peptide-like. In certain embodiments, the linker is a covalent bond (e.g., a carbon-carbon bond, disulfide bond, carbon-heteroatom bond, etc.). In certain embodiments, the linker is a carbon-nitrogen bond of an amide linkage. In certain embodiments, the linker is a cyclic or acyclic, substituted or unsubstituted, branched or unbranched aliphatic or heteroaliphatic linker. In certain embodiments, the linker is polymeric (e.g., polyethylene, polyethylene glycol, polyamide, polyester, etc.). In certain embodiments, the linker comprises a monomer, dimer, or polymer of aminoalkanoic acid. In certain embodiments, the linker comprises an aminoalkanoic acid (e.g., glycine, ethanoic acid, alanine, beta-alanine, 3-aminopropanoic acid, 4-aminobutanoic acid, 5-pentanoic acid, etc.). In certain embodiments, the linker comprises a monomer, dimer, or polymer of aminohexanoic acid (Ahx). In certain embodiments, the linker is based on a carbocyclic moiety (e.g., cyclopentane, cyclohexane). In other embodiments, the linker comprises a polyethylene glycol moiety (PEG). In other embodiments, the linker comprises amino acids. In certain embodiments, the linker comprises a peptide. In certain embodiments, the linker comprises an aryl or heteroaryl moiety. In certain embodiments, the linker is based on a phenyl ring. The linker may included funtionalized moieties to facilitate attachment of a nucleophile (e.g., thiol, amino) from the peptide to the linker. Any electrophile may be used as part of the linker. Exemplary electrophiles include, but are not limited to, activated esters, activated amides, Michael acceptors, alkyl halides, aryl halides, acyl halides, and isothiocyanates. In certain embodiments, the linker includes a maleimide group. In certain embodiments, the linker includes a NHS ester. In certain embodiments, the linker includes both a NHS ester and a maleimide group. For example, a cyclohexane ring may be substituted with an NHS ester and a maleimide group.

Ligation Methods

Figure 6C:
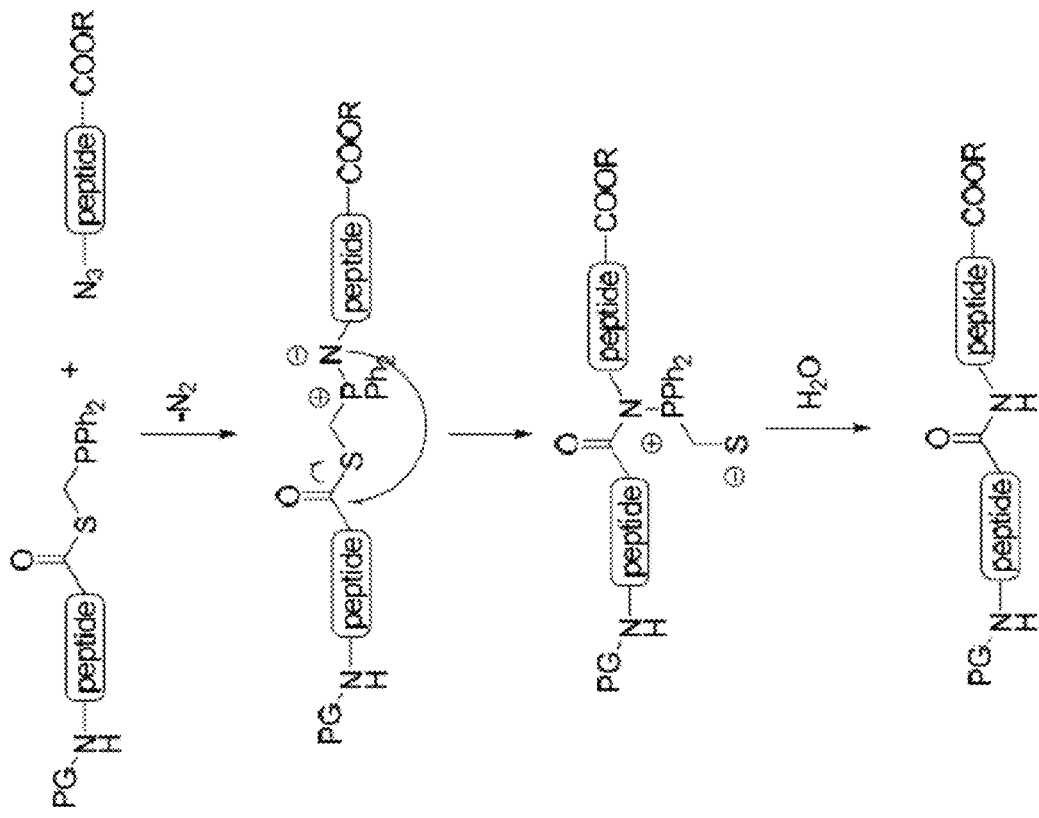
Figure 8:
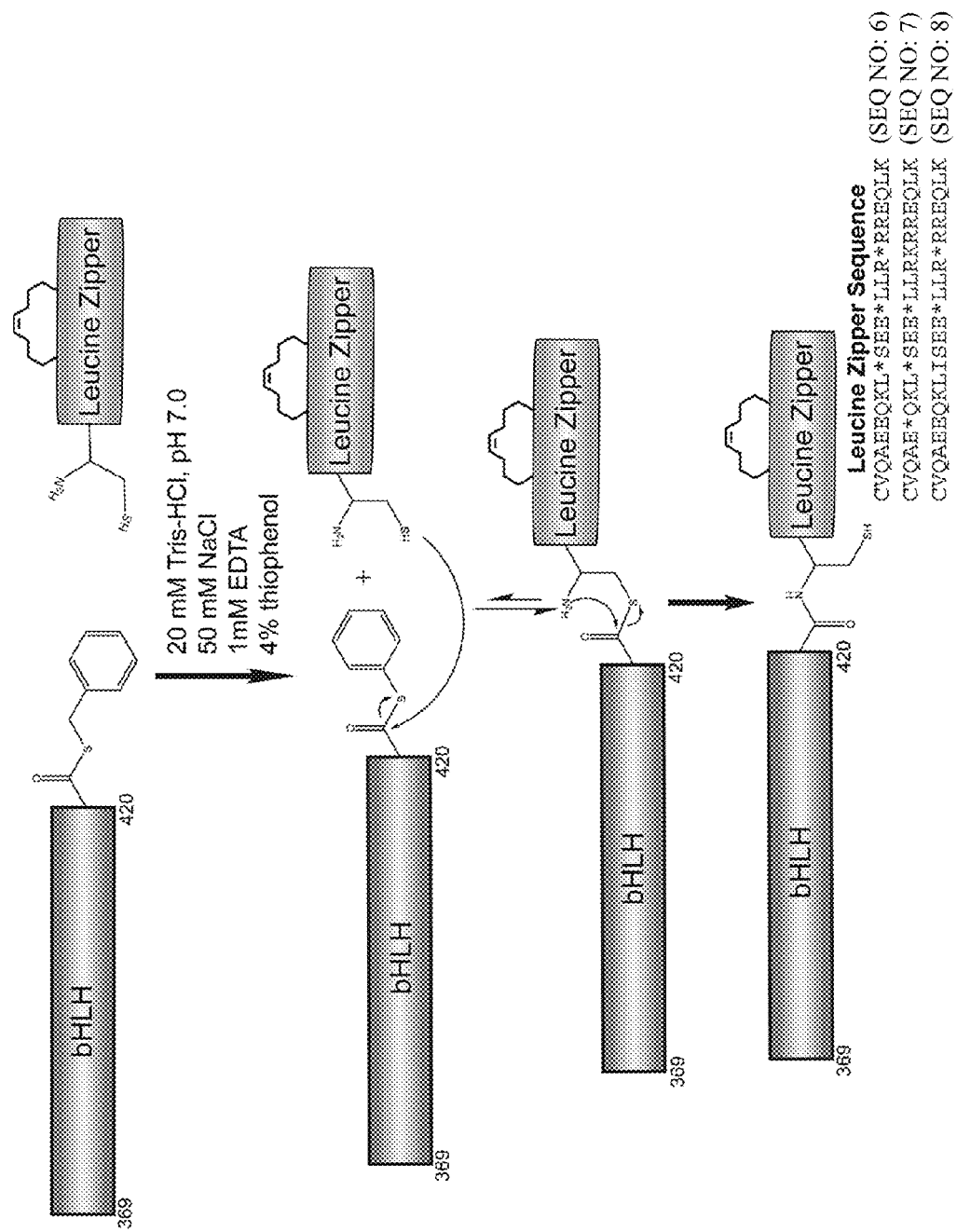
FIG. 8. Semi-synthetic c-Myc. The bHLH region (residues 369-419) is expressed as a fusion construct with an intein so as to create a C-terminal thioester after protein expression in *E. coli*. The leucine zipper region is synthesized as either a stapled or stitched variant with an N-terminal Cys (Cys will be introducing a S120C mutation). The components are ligated using Expressed Protein Ligation (the chemistry used for ligation can be varied).
Figure 9:
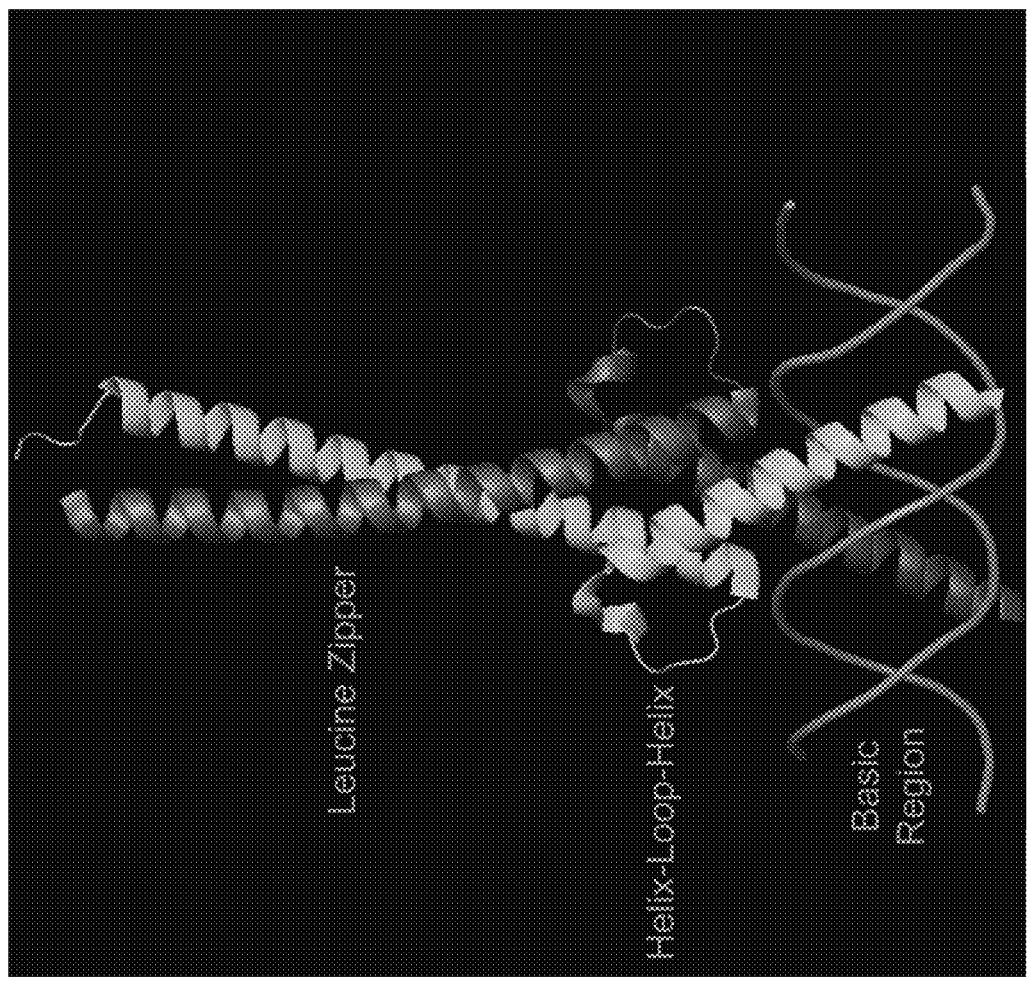
FIG. 9. Transcription factor c-Myc with a leucine zipper motif.
Figure 10:
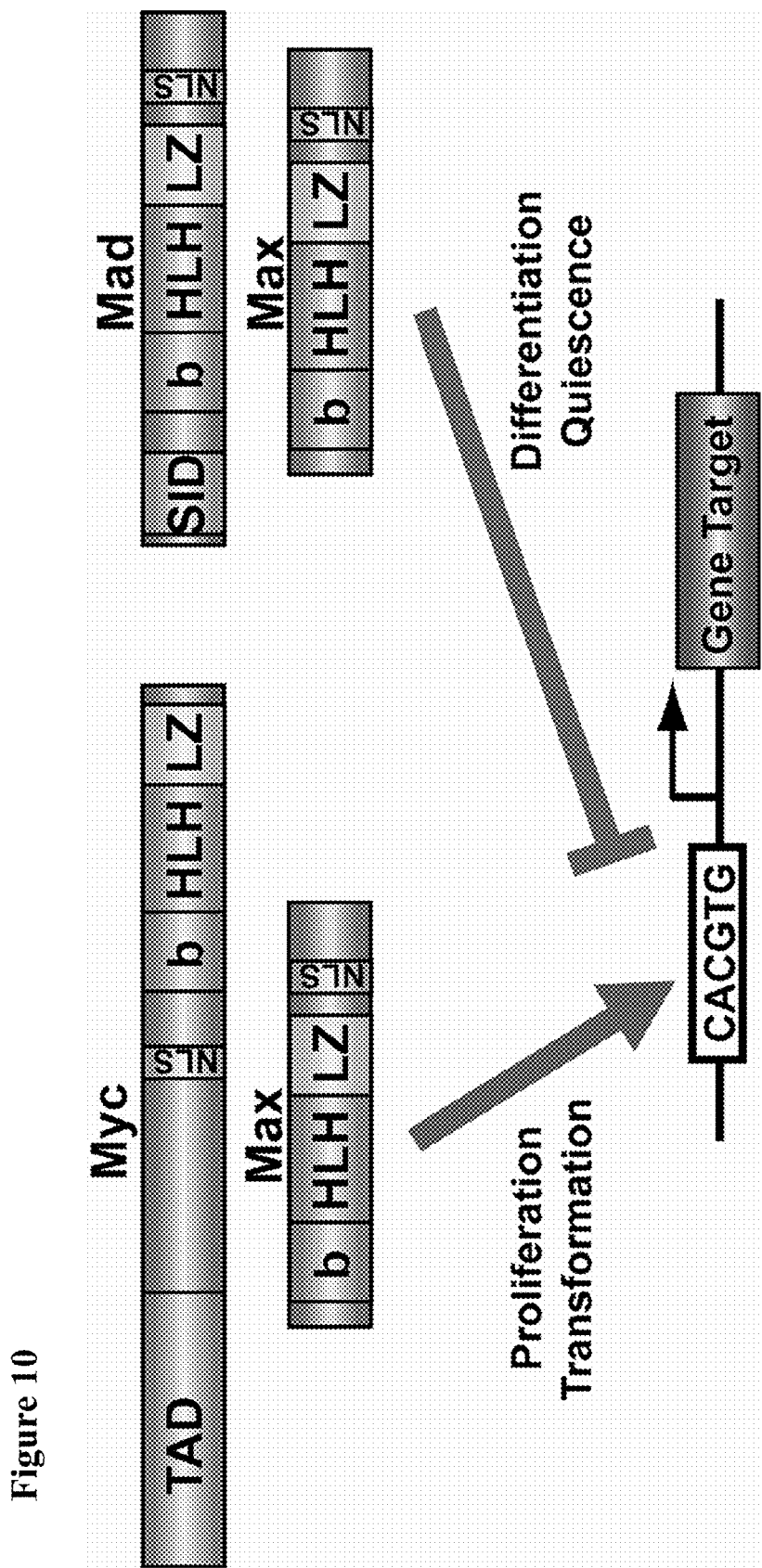
FIG. 10. Myc-induced gene transcription. The design rationale is to inhibit Myc:Max dimerization to prevent downstream gene upregulation. A stapled version of the leucine zipper can be synthesized so as to inhibit Max dimerization. The synthetic component can subsequently be ligated back to the basic Helix-Loop-Helix (bHLH) domain of Myc to act as a dominant negative by occupying DNA binding sites.
Figure 11:
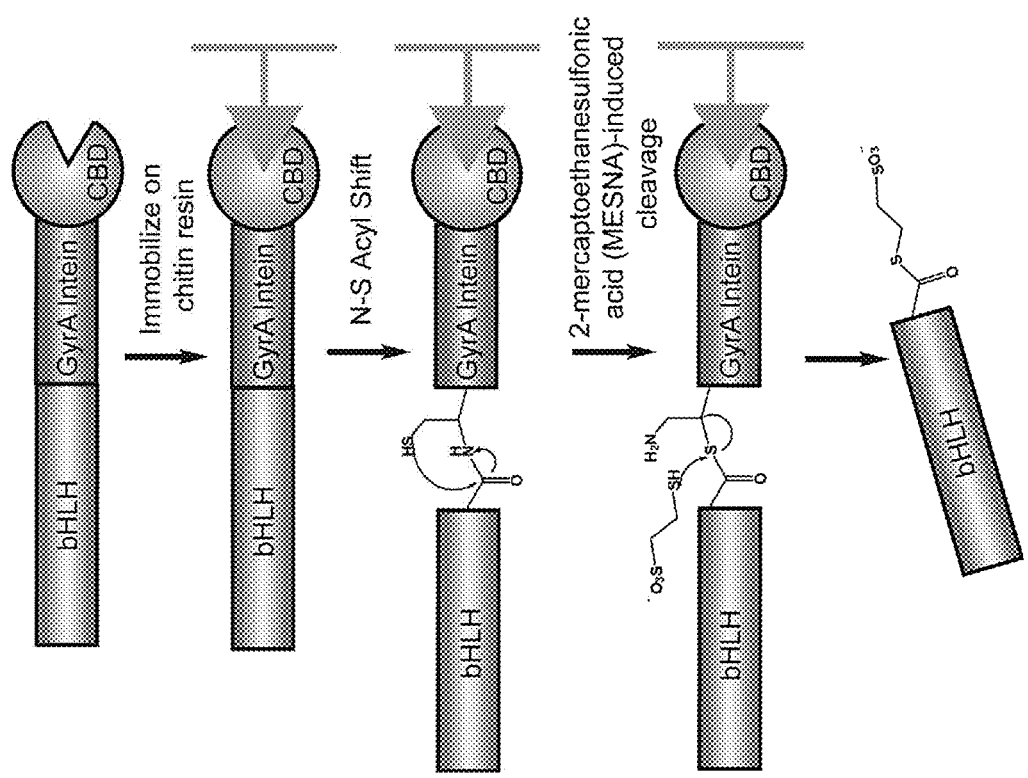
FIG. 11. Production of bHLH as a C-terminal thioester. bHLH (residues 369-419) will be expressed as a fusion construct with an intein so as to create a C-terminal thioester after protein expression in *E. coli*.
Figure 12:
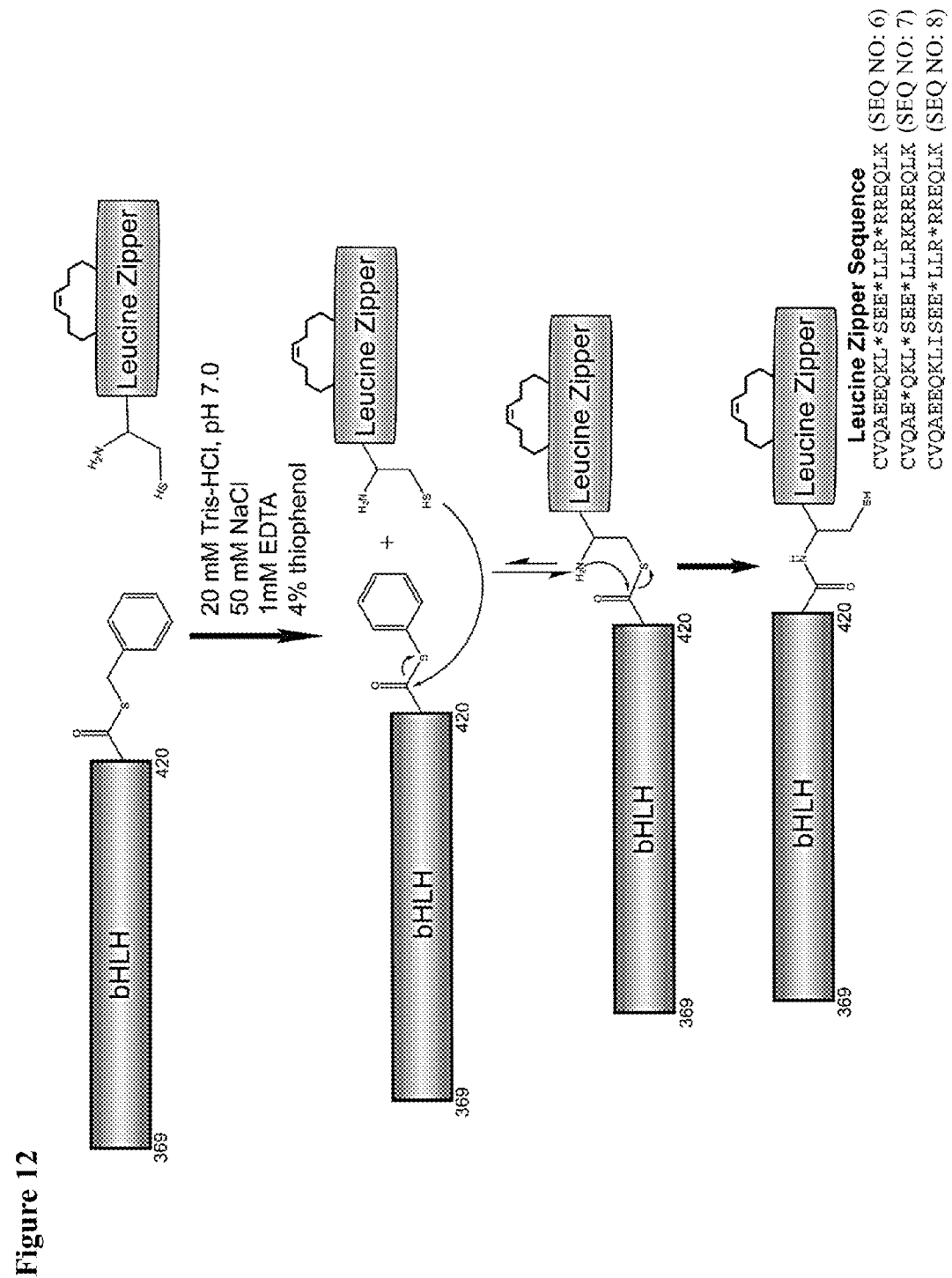
FIG. 12. Production of the stapled leucine zipper and expressed protein ligation. The leucine zipper region will be synthesized as either stapled or stitched variants with an N-terminal cysteine (cysteine will be introducing a S120C mutation). The components will be ligated using Expression Protein Ligation (the chemistry used for ligation can be varied).
Figure 13:
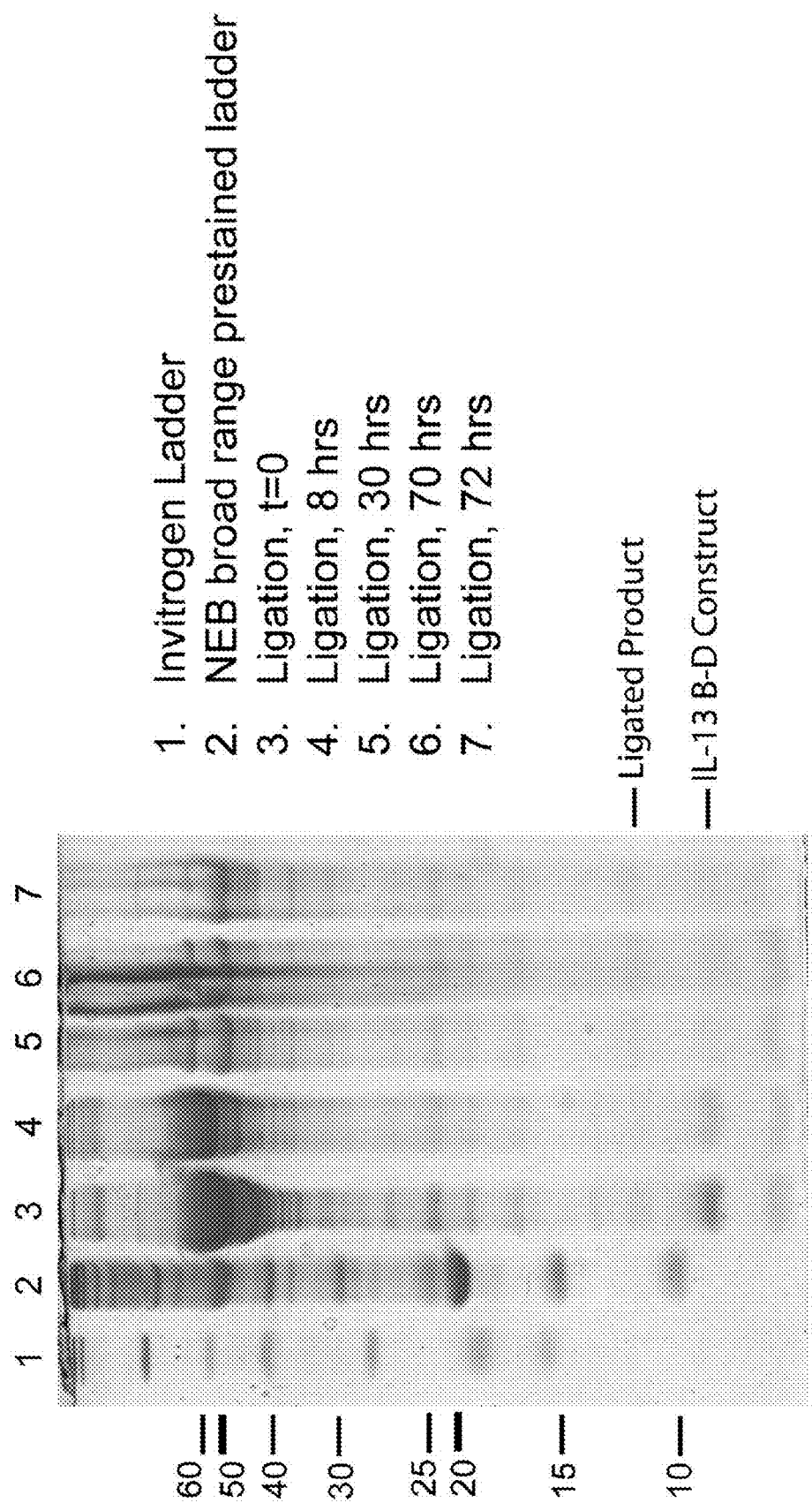
FIG. 13. Gel demonstration ligation product formation over time.
Figure 14:
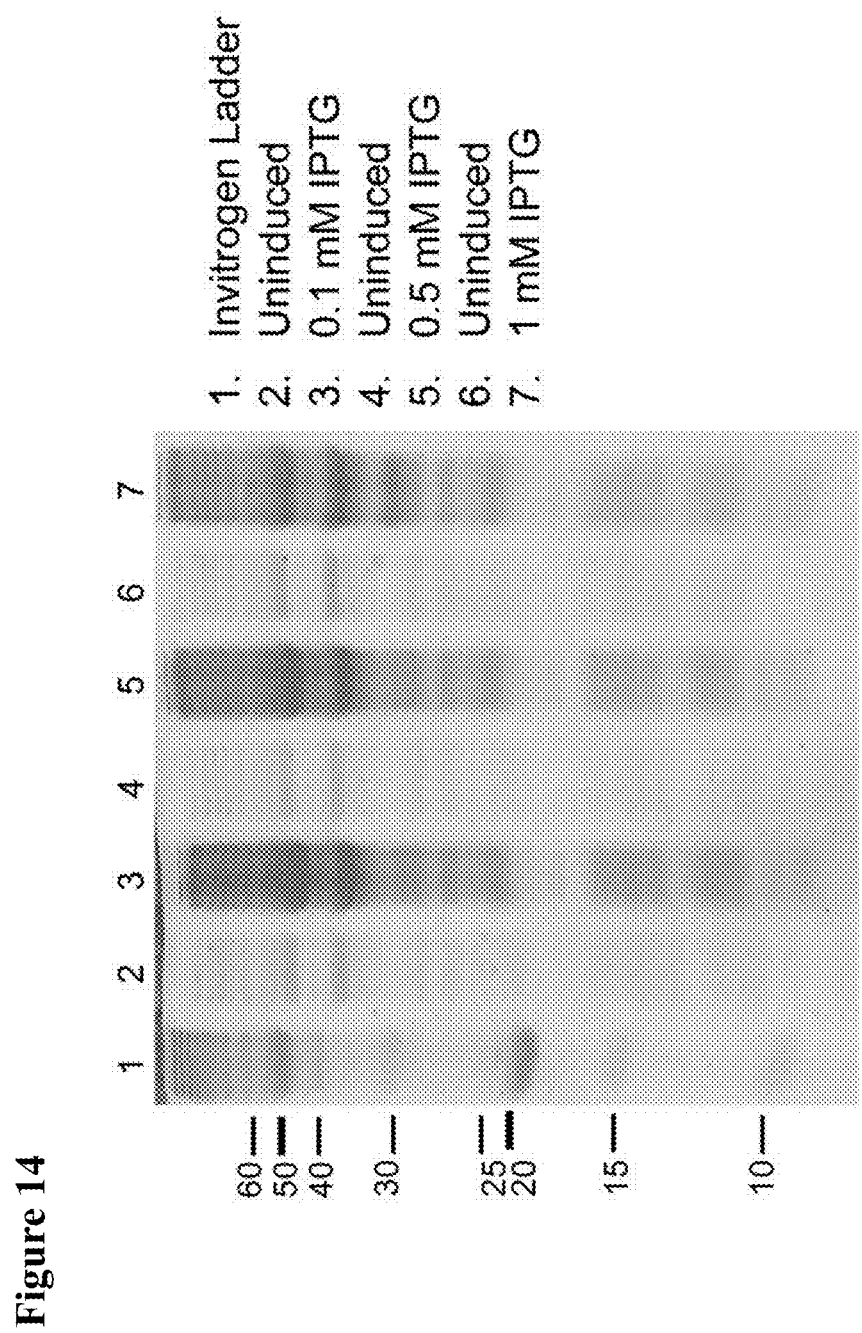
FIG. 14. Protein expression of an untagged version of the IL-13$_{26-112}$ construct under a T7-inducible promoter. Various induction times, temperatures, and IPTG concentrations were tested.

The synthesis of proteins of the current invention can be carried out by various enzymatic or chemical ligation methods (see Kimmerlin and Seebach, *J. Peptide Res.* (2005) 65: 229-260, incorporated herein by reference). In certain embodiments, a peptide or protein containing a C-terminal thioester is ligated to a peptide or protein containing an N-terminal cysteine residue using native chemical ligation to yield an amide bond at the ligation site. In certain embodiments, a synthetic peptide containing a C-terminal thioester is ligated to a recombinant protein containing an N-terminal cysteine residue using native chemical ligation (see Dawson et al., *Science* (1994) 266: 776-779 and U.S. Pat. No. 6,184,344; each of which is incorporated herein by reference). In other embodiments, a synthetic peptide containing an N-terminal cysteine residue is ligated to a recombinant protein C-terminal thioester in a method known as expressed protein ligation (see Muir et al., *Proc. Natl. Acad. Sci. USA* (1998) 95: 6705-6710, and U.S. Pat. Nos. 6,849,428 and 6,875,594; each of which is incorporated herein by reference). See FIG. 6 for examples of ligation methods.

In certain embodiments, proteins of the current invention may be produced by a version of native chemical ligation or expressed protein ligation that employs methionine, histidine, selenocysteine, or homoselenocysteine rather than cysteine as described above. Alternatively, a removable thiol-containing auxiliary may be employed in the place of the cysteine during the chemical ligation.

In other embodiments, an imine ligation strategy may be used to produce the inventive protein (see Liu et al., *J. Am. Chem. Soc.* (1994) 116: 4149-4153, incorporate herein by reference). The imine ligation employs a peptide or protein containing an N-terminal cysteine, threonine, or serine residue and a peptide or protein C-terminal glycoaldehyde. The process ultimately forms an amide bond and a hydroxymethyl-substituted pseudo-proline at the ligation site.

In another embodiment, a Staudinger ligation may be employed to generate the proteins of the current invention (see Nilsson et al., *Org. Lett.* (2000) 2: 1939-1941 and Saxon et al., *Science* (2000) 287: 2007-2010, each of which is incorporated herein by reference). Staudinger ligation involves the reaction of a polypeptide containing an N-terminal azide moiety with a polypeptide displaying a C-terminal phosphinothioester.

In other embodiments, an amide ligation by decarboxylative condensation of an N-hydroxyamine and an α-ketoacid may be used to produce the inventive protein (see Bode et al., *Angew. Chem. Intl. Ed.* (2006) 45: 1248-1252, incorporated herein by reference).

Those of ordinary skill in the art will readily appreciate that the invention may also include the use of nonnative chemical ligation strategies that incorporate something other than an amide bond at the ligation site. In certain embodiments, the linker between the stapled or stitched peptide and the protein is polyethylene glycol. In certain embodiments, the linker is a hydrocarbon linker. In certain embodiments, the linker is a polyamine.

Interleukin-13

The inventive strategy has been used to design an antagonist of IL-13 for the treatment of asthma. IL-13 is a soluble, secreted protein that folds to form a four-helix bundle structure (Moy, F. J., Diblasio, E., Wilhelm, J., and Powers, R. (2001) *J Mol Biol* 310(1), 219-230; Eisenmesser, E. Z., Horita, D. A., Altieri, A. S., and Byrd, R. A. (2001) *J Mol Biol* 310(1), 231-241; each of which is incorporated herein by reference) having strong similarity to other members of the short-chain family of cytokines, including GM-CSF, erthropoietin, human growth factor, IL-4, and IL-6. The amino acid sequence of human IL-13 (GenBank accession number P35225-1, incorporated herein by reference) is as follows:

(SEQ ID NO: 1)
GPVPPSTALRELIEELVNITQNQKAPLCNGSMVWSINLTAGMYCAAL

ESLINVSGCSAIEKTQRMLSGFCPHKVSAGQFSSLHVRDTKIEVAQF

VKDLLLHLKKLFREGRFN

Like all known members of this family, IL-13 signals by simultaneously engaging two transmembrane receptor subunits and thus causing receptor dimerization. The receptors for IL-13 and IL-4 share one subunit, i.e., IL-4Rα. The other subunit of the IL-13 dimeric receptor complex is IL-13Rα1, which appears to be dedicated to IL-13 alone and is not shared by other cytokines (Thompson, J. P., and Debinski, W. (1999) *J Biol Chem* 274(42), 29944-29950; incorporated herein by reference). The dimerization of IL-4Rα and IL-13Rα1 by IL-13 causes the activation of the Jak2/STAT-6 signaling pathway, which sets off a cascade that leads to bronchoconstriction. A second, truncated form of the IL-13-specific receptor subunit, IL-13Rα2, lacks any intracellular signaling motifs yet binds IL-13 with high affinity and thus is believed to function as a soluble IL-13 decoy receptor. Consistent with this notion, IL-13Rα2 has been shown to down-regulate IL-13 signaling by preventing activation IL-4Rα/IL-13Rα1 receptor complex (Wills-Karp, M., Luyimbazi, J., Xu, X., Schofield, B., Neben, T. Y., Karp, C. L., and Donaldson, D. D. (1998) *Science* 282(5397), 2258-2261; incorporated herein by reference). IL-13 and its heterodimeric receptor (IL-4Rα/IL-13Rα1) are widely considered to be among the most attractive targets for therapeutic intervention in asthma (Wills-Karp, M. (2004) *Immunol Rev* 202, 175-190; incorporated herein by reference). Therefore, an antagonist of IL-13 has been designed and created using the inventive system described herein. The IL-13 antagonist is a modified version of IL-13 with hydrophobic protein staple in helix A of IL-13.

Modified versions of IL-13 have been designed that bind to IL-13Rα1 while abrogating its interaction with IL-4Rα. A stapled version of IL-13 was designed to meet these criteria. Garcia and co-workers have reported the x-ray structure of the IL-4Rα/IL-13/IL-13Rα1 complex. This structure shows that IL-4Rα and IL-13Rα1 bind to adjacent but distinct and non-overlapping surface patches on IL-13 (FIG. 7). Mutational studies are consistent with this overall picture, having implicated helices A, C, and D of IL-13 as being involved in receptor engagement. One residue in particular, Glu12 of helix A, is indicated by both the x-ray structure and mutational studies to be a key interaction site with IL-4Rα (Thompson, J. P., and Debinski, W. (1999) *J Biol Chem* 274(42), 29944-29950; LaPorte, S. L., Juo, Z. S., Vaclavikova, J., Colf, L. A., Qi, X., Heller, N. M., Keegan, A. D., and Garcia, K. C. (2008) *Cell* 132, 259-272; Debinski, W., and Thompson, J. P. (1999) *Clin Cancer Res* 5(10 Suppl), 3143s-3147s; each of which is incorporated herein by reference). As helix A is the only helix in IL-13 that interacts with both IL-4Rα and IL-13Rα1 (using distinct contact surfaces), this is the logical site at which to introduce a hydrocarbon staple intended to cause steric disruption of binding to IL-4Rα while preserving or enhancing binding to IL-13Rα1. Staple-dependent enhancement of IL-13Rα1 binding could result from increased conformational pre-organization of helix A, or from direct and favorable hydrophobic contacts between the hydrophobic stable and side chains of IL-13Rα1, or both. Essentially, the design concept centers around the notion that incorporation of a hydrocarbon staple into an otherwise wild type IL-13 molecule will produce a "dominant negative" version of IL-13 that retains the ability to bind one receptor subunit, IL-13Rα1, but not the other, IL-4Rα. The stapling is also expected to impart desirable pharmacologic properties on the protein without causing it to become immunogenic.

The designed "dominant negative" version of IL-13 was prepared using the inventive semi-synthetic approach whereby a stapled peptide is ligated onto a truncated version of IL-13 produced by recombinant techniques. Specifically, a fully synthetic peptide comprising helix A with a site-specific hydrocarbon staple is joined to a recombinant IL-13 fragment lacking helix A (FIG. 1). Expressed protein ligation (EPL) was used to couple the peptide to the recombinant IL-13 fragment (FIG. 14). The N-terminal component (i.e., the staple helix A peptide) with a C-terminal thioester is ligated to the C-terminal component (i.e., the recombinant IL-13 fragment) with an N-terminal cysteine. Wild-type IL-13 contains a cysteine residue (cys26) conveniently located in a partially disordered loop between helix B and helix C, thus providing a convenient disconnection point between the synthetic peptide (residues 1-25) and the recombinant IL-13 fragment (residues 26-112). Because EPL results in a native peptide bond at the ligation site, the reconnection at residues 25 and 26 provides a modified version of IL-13 that differs only in the presence of a staple in helix A.

Helix A Peptide. A panel of stapled helix A C-terminal thioester peptides were used to make a panel of modified stapled IL-13 proteins as shown in FIG. 5 and FIG. 19 (IL-13 A-Helix: STALRELIEELVNITQNQKAPL (SEQ ID NO: 4) and ALRELIEELVNITQNQKAPL (SEQ ID NO: 5)). Residues that contribute to the internal packing interactions of the protein (denoted by arrows) have been excluded as candidates for insertion of unnatural amino acids for the staple. All other positions have been explored. The staple is either positioned at i, i+4; i, i+3; or i, i+7. In certain embodiments, the unnatural amino acids for the staple are at positions i and i+3. In certain embodiments, the unnatural amino acids for the staple are at positions i and i+4. For example, the unnatural amino acids and subsequent staple may be placed at residues 7 and 11, residues 8 and 12, residues 11 and 15, residues 12 and 16, residues 15 and 19, and residues 18 and 22. In certain embodiments, the unnatural amino acids for the staple are at positions i and i+7. For example, the unnatural amino acids and subsequent staple may be place at residues 7 and 14, residues 11 and 18, residues 12 and 19, and residues 15 and 22. The stereochemistry of the unnatural amino acids that provide precursors to the staple may be in the S or R stereochemistry. In certain embodiments, both amino acids are in the S,S configuration. In other embodiments, both amino acids are in the R,R configuration. In still other embodiments, the amino acids are in the R,S configuration. In certain embodiments, the unnatural amino acids for the staple are at positions i and i+7, and the amino acids are in the R and S configurations.

The peptide comprising helix A and the unnatural amino acids for the staple may be prepared using any method known in the art. In certain embodiments, the peptide is prepared synthetically in order to incorporate the unnatural amino acids at the desired positions. In certain embodiments, the peptide is prepared using Boc chemistry. In certain embodiments, the stapled peptide is of the sequence: STALR$S_5$LIE$S_5$LVNITQNQKAAL (SEQ ID NO: 3).

The peptide may be prepared as a resin-bound thioester. The syntheses of α-methyl,α-alkenyl amino acids has been reported (Schafmeister, C. E., Po, J., and Verdine, G. L. (2000) *J. Am. Chem. Soc.* 122(24), 5891-5892, also cite patent application with synthesis). As would be appreciated by one of skill in the art, other unnatural amino acids that provide the necessary alkenyl moiety for stapling may be used in the peptide. Certain unnatural amino acids that would find use in stapling peptides are described herein.

IL-13 Fragment. The protein comprising the remaining portion of IL-13 may be prepared using any technique known in the art. As would be appreciated by one of skill in the art, modified version of IL-13 may also be used in the inventive stapled IL-13 protein. For example, amino acids may be mutated, deleted, or inserted from the wild type IL-13 protein. In certain embodiments, the IL-13 protein is 80%, 85%, 90%, 95%, 98%, or 99% identical to the wild type IL-13 protein. The protein may be prepared synthetically or biologically. In certain embodiments, the truncated protein starting with cysteine 26 at the N-terminus is prepared. In certain embodiments, a construct encoding residues 26-112 of IL-13 is produced with an N-terminal methionine residue which is subsequently removed by biosynthetic machinery to yield cysteine 26 at the N-terminus. The resulting biosynthetic IL-13 fragment may be optionally purified and characterized. In certain embodiments, the IL-13 fragment is characterized by electrospray mass spectrometry and/or Edman degradation.

In other embodiments, a full version of IL-13 is produced, and the full version is subsequently cleaved to yield cysteine 26 at the N-terminus. Any protease may be used to yield the desired IL-13 fragment. In certain embodiments, Factor Xa is used to cleave the N-terminus and yield cysteine 26 at the N-terminus. A strategy for producing IL-13 with an N-terminal cysteine using proteolytic degradation with Factor Xa (Erlanson, D. A., Chytil, M., and Verdine, G. L. (1996) *Chem Biol* 3(12), 981-991; incorporated herein by reference) is illustrated in FIG. 1. A Factor Xa cleavage site (i.e., IEGR) was introduced into the partially disordered loop between helix A and helix B immediately abutting Cys26. The resulting construct was produced recombinantly, the protein was purified and subjected to Factor Xa cleavage, thereby producing IL-$13_{26-112}$. In certain embodiments, the cleaved IL-$13_{26-112}$ is purified from the uncleaved starting material. Other cleavage sites and protease may be used to produce the IL-$13_{26-112}$ fragment. For example, enterokinase, the protease from Tobacco Etch virus, trypsin, chymotrypsin, pepsin, papain, elastase, thrombin, plasmin, furin, and ubiquitin C-terminal hydrolase may be used.

Figure 15:
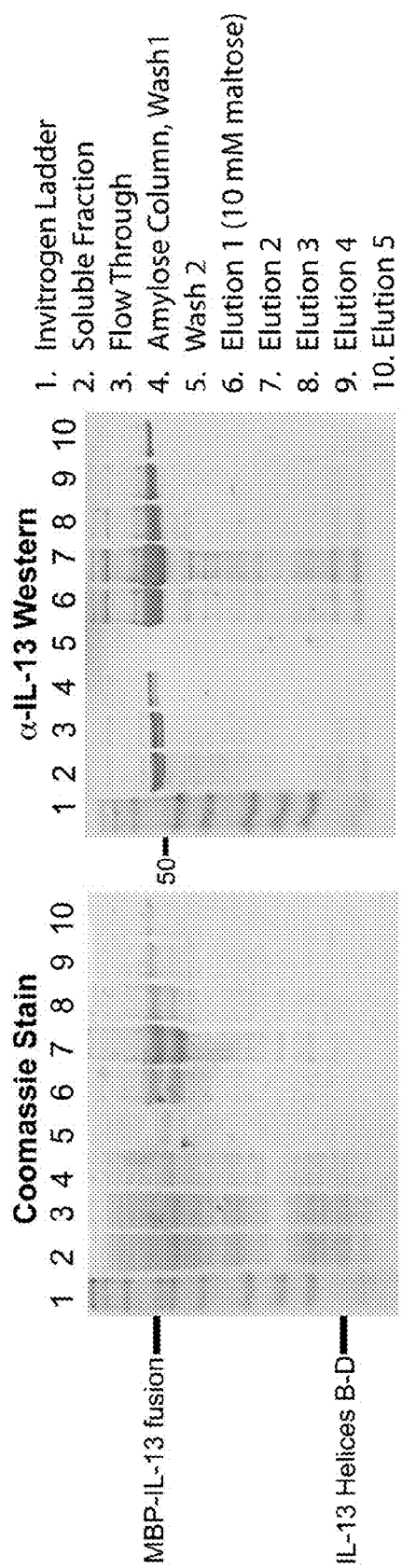
FIG. 15. Protein expression and intracellular TEV processing for an MBP-IL-13 fusion construct.
Figure 16:
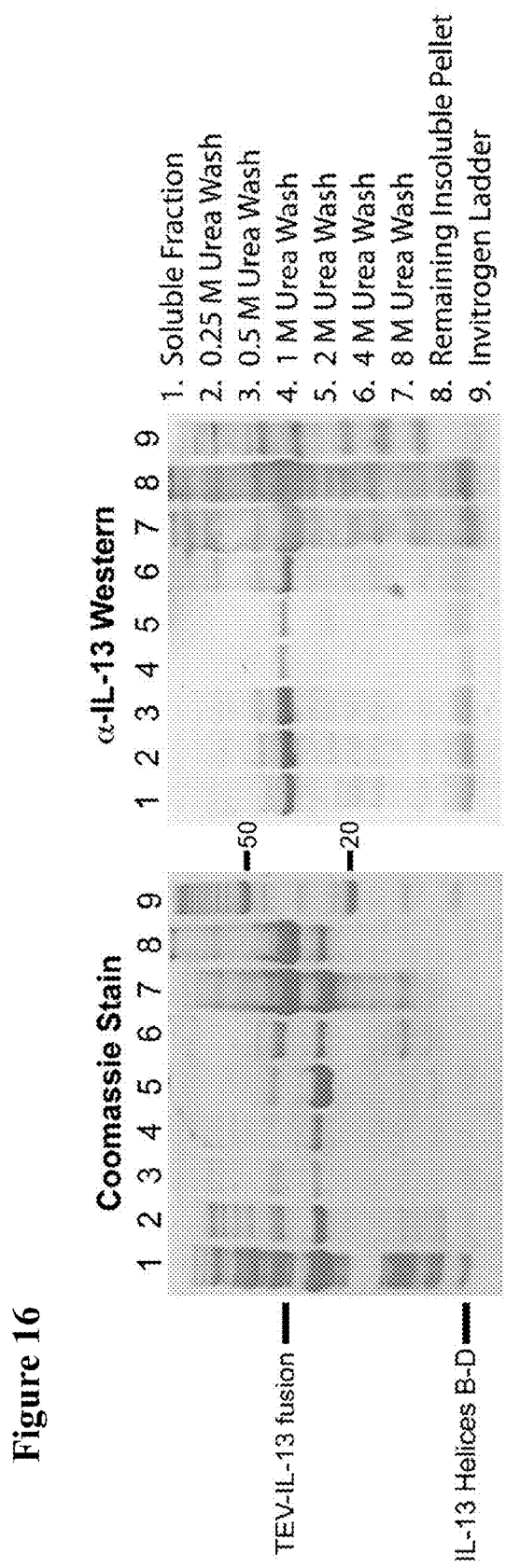
FIG. 16. Protein expression by creating a TEV protease-IL-13$_{26-112}$ fusion construct.
Figure 17:
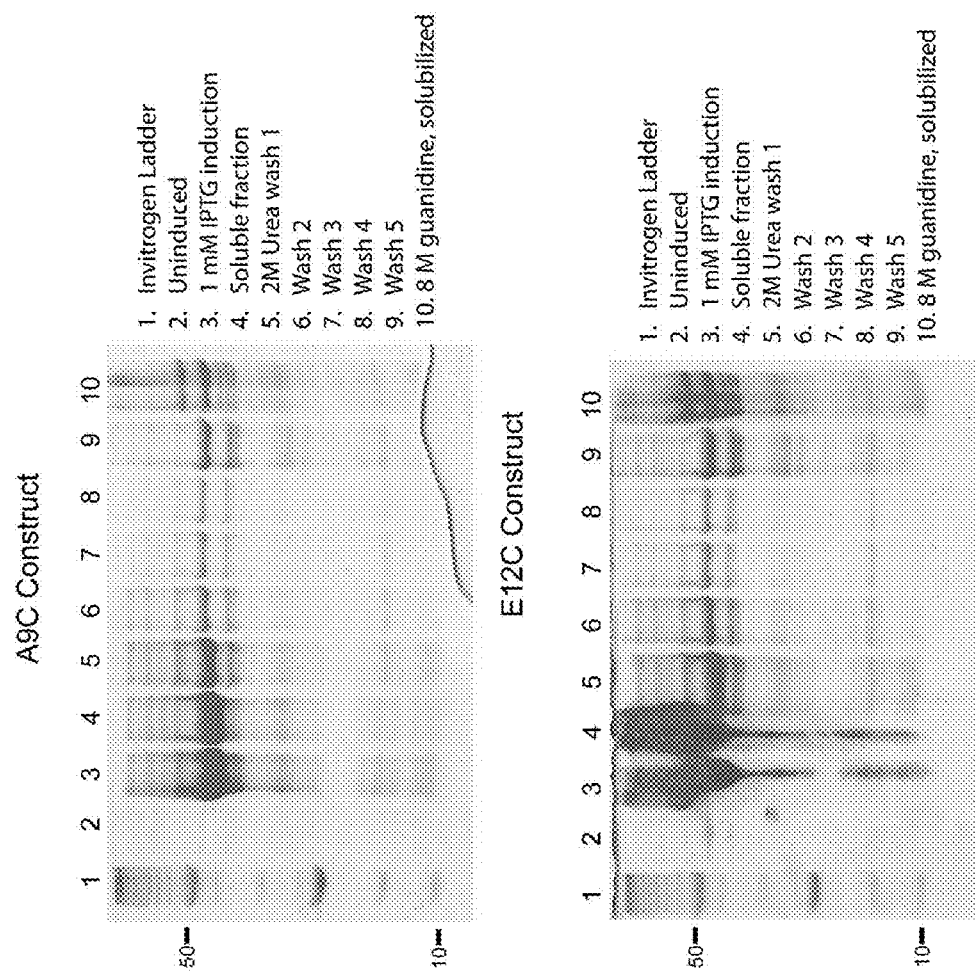
FIG. 17. Protein expression for IL-13 constructs that express portions of Helix-A.
Figure 18:
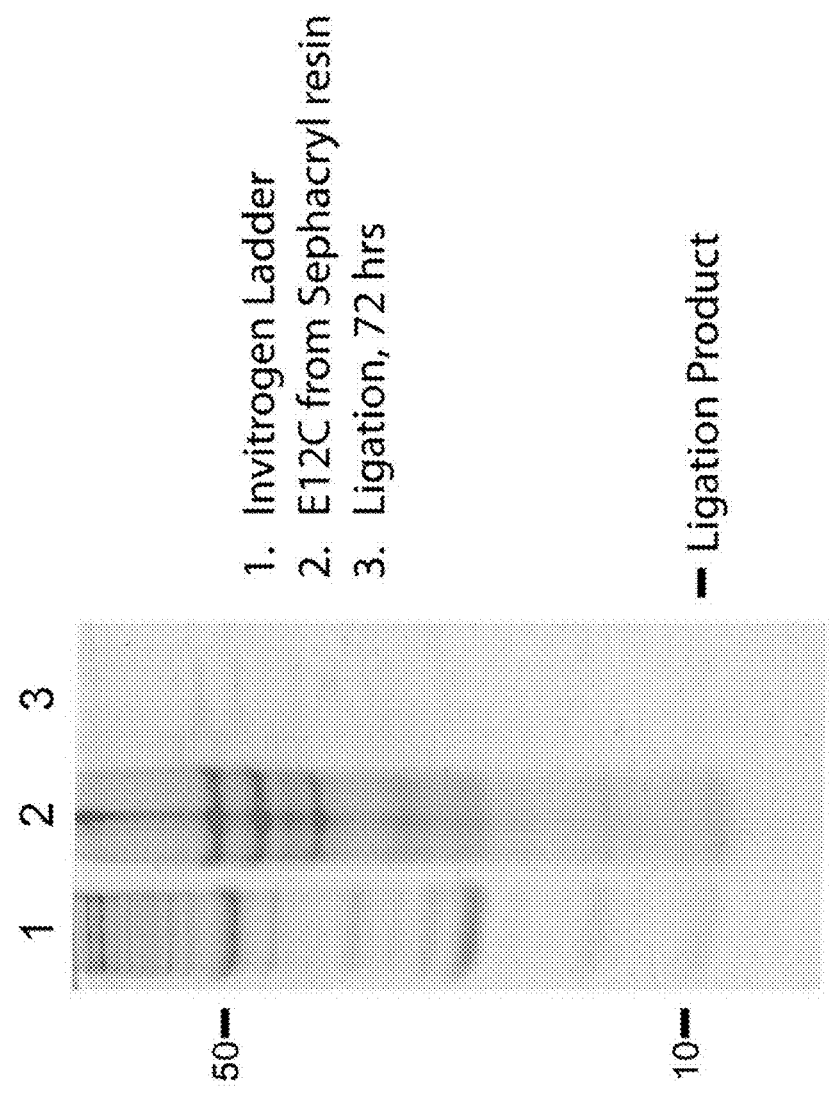
FIG. 18. Expressed protein ligation for the IL-13 construct starting at residue 12.
Figure 19A:
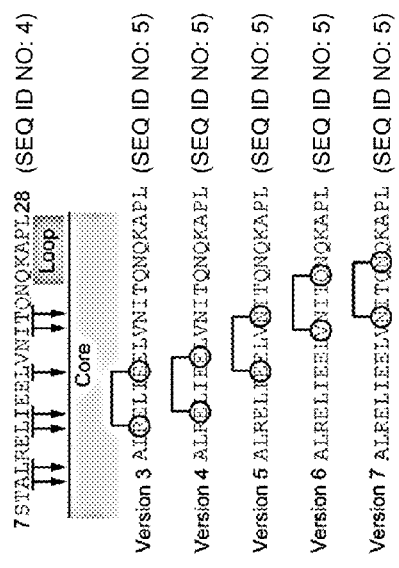
FIGS. 19A-19C. (A) Proposed library of i, i+4 stapled variants of Helix-A. The non-natural amino acids were introduced at positions that are not involved in core-packing interactions of Il-13. (B) Predicted helicity of each stapled variant. Secondary structure calculations were performed using Monte Carlo simulations after introduction of the hydrocarbon staple. (C) Stapled peptide variants of Helix-A were synthesized and purified by HPLC before analysis by circular dichroism.
Figure 19B:
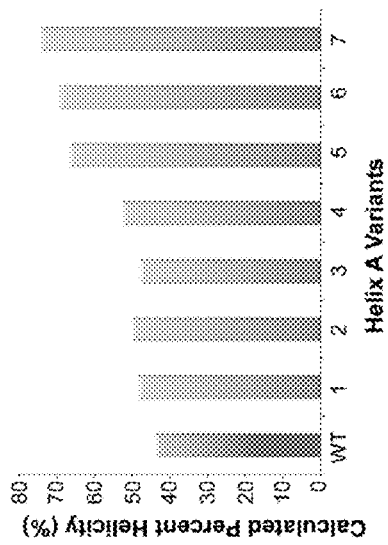
Figure 19C:
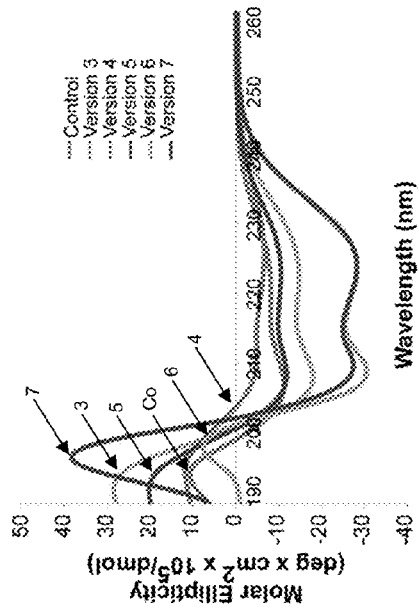

In certain embodiments, a variant full-length construct of IL-13 is fused to the C-terminus of maltose binding protein (MBP). In certain embodiments, a TEV cleavage site is inserted into the loop region of IL-13 between Helix-A and -B just before Cys 26, such that TEV cleavage is expected to separate Helix A from the desired Cys-terminated BCD fragment. In some embodiments, the A-helix is provided in trans to associate with the remainder of the protein. In this the case, the MBP portion fused to Helix-A can be used for purification. The soluble portion is combined with amylose resin by batch binding to isolate the MBP-Helix-A fragment, and the Helices B-D construct is screened for its affinity as a secondary conjugate (FIG. 15).

In certain embodiments, plasmids are designed in which TEV protease is directly be fused to the IL-$13_{26-112}$ construct downstream of a T7 promoter. In certain embodiments, the TEV-IL-$13_{26-112}$ construct is generated to contain a short linker bearing the TEV recognition sequence immediately before Cys 26 of IL-13.

Ligation. Any ligation or coupling reaction may be used to join the peptide comprising helix A with the IL-$13_{26-112}$ fragment. In certain embodiments, expressed protein ligation is used to prepare the inventive stapled IL-13. The ligation reaction may be performed under denaturing or non-denaturing conditions. In certain embodiments, the folded IL-$13_{26-112}$ fragment is ligated to the stapled peptide under non-denaturing conditions. In certain embodiments, denatured IL-$13_{26-112}$ fragment is ligated to the stapled peptide, and then the resulting ligation product is subsequently refolded. In certain embodiments, the ligation is product is re-folded by dialysis.

In another embodiment, both stapled or stitched versions of Helices A and D are prepared synthetically and ligated to the remainder of the IL-13 protein (i.e., Helices B-C). For example, the Helices B-C portion of IL-13 may be produced recombinantly and contains a C-terminal thioester and an N-terminal cysteine. See FIG. 4. The N-terminal cysteine of Helix B is essentially protected by the flanking peptide sequence. After Helix D is attached to the recombinant protein portion, the N-terminal flanking peptide sequence is removed by a protease such as Factor Xa to expose an N-terminal cysteine. Synthetic Helix A is subsequently attached to the protein. Modifying Helices A and D may result in blocking interactions with one receptor (IL-4Rα and Helix A) while stabilizing interactions with the other receptor (IL-13Rα1 and Helix D).

In another embodiment, a staple or stitched version of Helix D is prepared synthetically and ligated to the remainder of the IL-13 protein (i.e., Helices A-B-C). For example, the Helices A-B-C portion of IL-13 may be produced recombinantly and contains a C-terminal thioester. See FIG. 8.

After the ligation product is prepared, the modified IL-13 protein may be characterized by any technique known in the art for characterizing proteins or peptides. In certain embodiments, high-resolution electrospray mass spectometry is used. The location of the staple may be verified by Edman degradation or LC/MS/MS peptide mapping. Helical content and thermal melting behaviour may be assessed by circular dichroism spectropolarimetry. In certain embodiments, NMR spectroscopy or x-ray crystallography may be used to characterize the modified stapled IL-13. The biological activity of the modified IL-13 protein may also be assessed using biochemical, cellular assays (Wills-Karp, M., Luyimbazi, J., Xu, X., Schofield, B., Neben, T. Y., Karp, C. L., and Donaldson, D. D. (1998) *Science* 282(5397), 2258-2261; Knackmuss, S., Krause, S., Engel, K., Reusch, U., Virchow, J. C., Mueller, T., Kraich, M., Little, M., Luttmann, W., and Friedrich, K. (2007) *Biol Chem* 388(3), 325-330; LaPorte, S. L., Juo, Z. S., Vaclavikova, J., Colf, L. A., Qi, X., Heller, N. M., Keegan, A. D., and Garcia, K. C. (2008) *Cell* 132, 259-272; each of which is incorporated herein by reference), or animal models of asthma. Pharmacokinetics and pharmadynamics of the protein may also be determined. In certain embodiments, the stapled IL-13 protein is useful in the treatment of asthma or other inflammatory disease. The stapled IL-13 protein may be combined with a therapeutically acceptable excipient for administration to a subject in need thereof. In certain embodiments, a therapeutically effective amount of the stapled IL-13 protein is combined with a therapeutically acceptable excipient in a pharmaceutical composition. The formulation of pharmaceutical compositions is described in more detail below.

c-Myc

The transcription factor cMyc may also be modified using the inventive technology. c-Myc is a dimeric protein complexes consisting of a leucine zipper portion, a helix-loop-helix portion, and a basic DNA-binding region (FIG. 9). In order to prevent gene upregulation that may lead to proliferation and/or transformation, the dimerization of Myc and Max (as shown in FIG. 10) may be inhibited by a stapled or stitched Myc. In certain embodiments, a stapled version of the leucine zipper of Myc is prepared and incorporated into Myc to inhibit the dimerization of Myc and Max. The synthetic leucine zipper portion of Myc is ligated to the basic Helix-Loop-Helix (bHLH) domain of Myc to act as a dominant negative by occupying the DNA binding sites responsible for gene upregulation. The synthetic stapled leucine zipper is created with an N-terminal cysteine residue. In certain embodiments, a cysteine residue is introduced as a mutation. In certain particular embodiments, an S120C mutation is created to leave a cysteine at the N-terminus of the synthetic leucine zipper peptide. In certain embodiments, the bHLH portion (residues 369-419, e.g., stapled peptides: CVQAEEQKLXSEEXLLRXRREQLK (SEQ ID NO: 6), CVQAEXQKLXSEEXLL RKRREQLK (SEQ ID NO: 7), CVQAEEQKLISEEXLLRXRREQLK (SEQ ID NO: 8)) is expressed as a fusion construct with an intein (e.g., the GyrA intein) so as to create a C-terminal thioester after protein expression in *E. coli* (FIG. 11). The two components are then ligated together using expressed protein ligation (FIG. 12) although other ligation methods as described herein may also be used. In certain embodiments, the ligation method creates an amide bond. In a similar manner, other transcription factors may be modified to create transcription factors with altered biological activity. Such modified proteins may be useful in the treatment of proliferative disease such as cancer or inflammatory diseases.

Max

Max is a member of the bHLH-LZ (basic region-helix 1-loop-helix 2-leucine zipper) family of transcription factors. While Max can homodimerize and bind to specific Enhancer box (E box) sequences, Max is also an obligate partner for several members of the Myc family for E box binding. Max is constitutively expressed and is believed to establish a basal state of transcriptional activity for target genes that are also recognized by other Myc family members. When Myc family members are upregulated, these heterodimer complexes will compete with Max homodimers for transcriptional regulation, leading to transcriptional upregulation or repression of their target genes. Myc family members are responsible for transcriptional regulation of numerous key cellular processes including cell cycle regulation, apoptosis and metabolism, and deregulated activity of Myc family members has been associated with a variety of malignancies. Max homodimerization acts to repress cMyc activity and a dominant negative version of Max might be an antagonist for cMyc downregulation in an oncogenic state.

Figure 20:
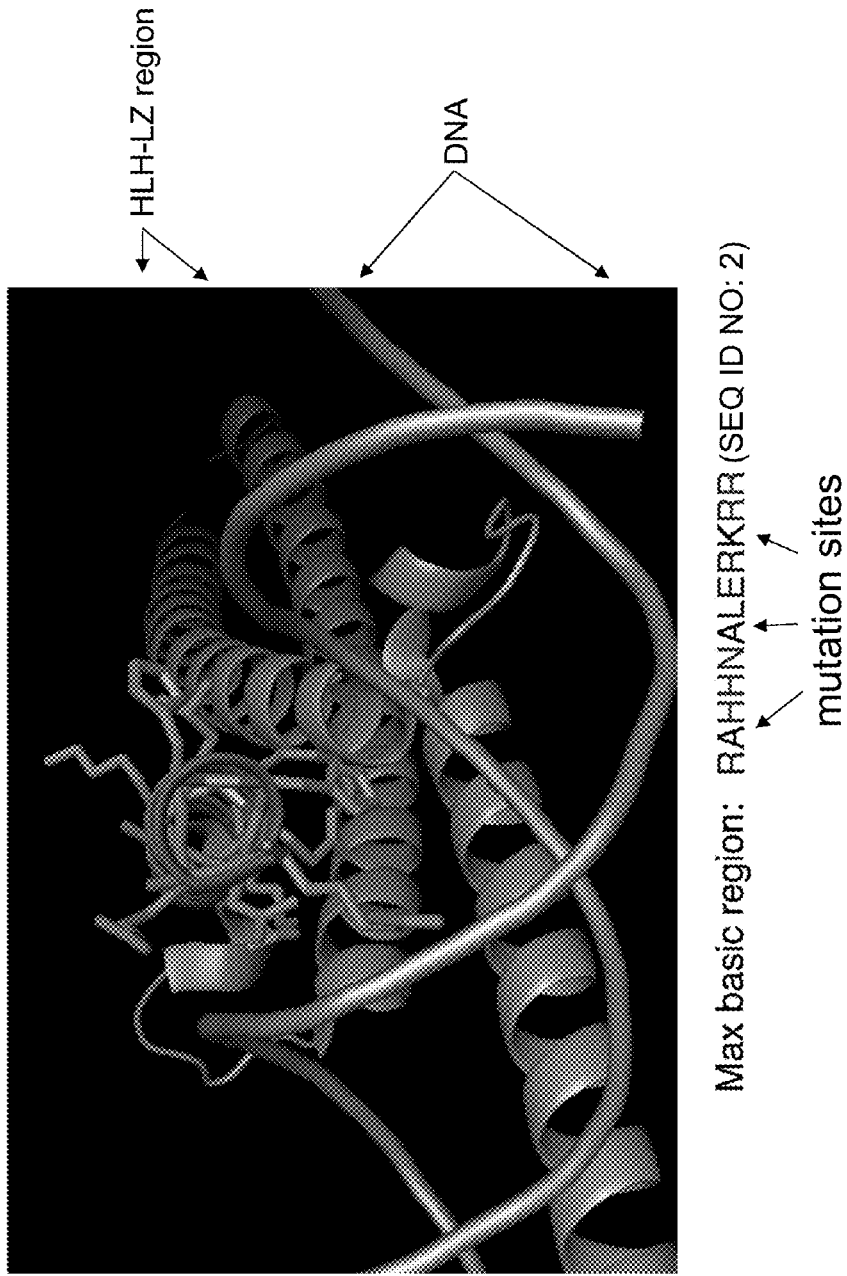
FIG. 20. Identifying sites for modification in the basic region of Max. Based upon crystallographic analysis, several sites were identified in which modifications could be introduced without affecting DNA-binding interactions. The basic region, selected mutation sites, the HLH-LZ region of the protein and DNA are shown.

In certain embodiments, chemical modifications are introduced into the DNA binding basic region of Max (RAHH-NALERKRR, SEQ ID NO: 2), see FIG. 20. It is thought that the basic region undergoes a disorder-to-order structural transition upon DNA binding, and therefore improved binding may become more favorable by locking these residues into a pre-binding state where the entropic penalty is removed. This can be accomplished by introducing non-natural amino acids within this region, then stapling the sequence into an alpha-helical structure via ring-closing metathesis chemistry. In certain embodiments, structural elements of Max that are involved in protein-protein interactions for dimerization, the helix-loop helix (HLH) and leucine zipper (LZ) regions, are recombinantly expressed and ligated to the synthetic basic region of Max.

In certain embodiments, i, i+4 peptides and one i, i+7 peptide derived from the basic region are synthesized with an N-terminal PEG-3 linker to increase solubility while also distancing the FITC group from the DNA binding region (FIG. 21). In certain embodiments, non-natural amino acids are introduced at positions that are not involved in DNA binding. In certain embodiments, the terminal olefins were linked together using ring-closing metathesis chemistry to promote stability of an alpha-helical secondary structure.

In certain embodiments, the synthesized peptides are purified by HPLC. In certain embodiments, peptide, i, i+4 version 1 (FIG. 22) is synthesized so as to contain a C-terminal thioester. The peptide is synthesized using t-Boc chemistry on 3-S-trityl-mercaptopropionyl resin and purified by HPLC and confirmed by LC/MS analysis.

Figure 23:
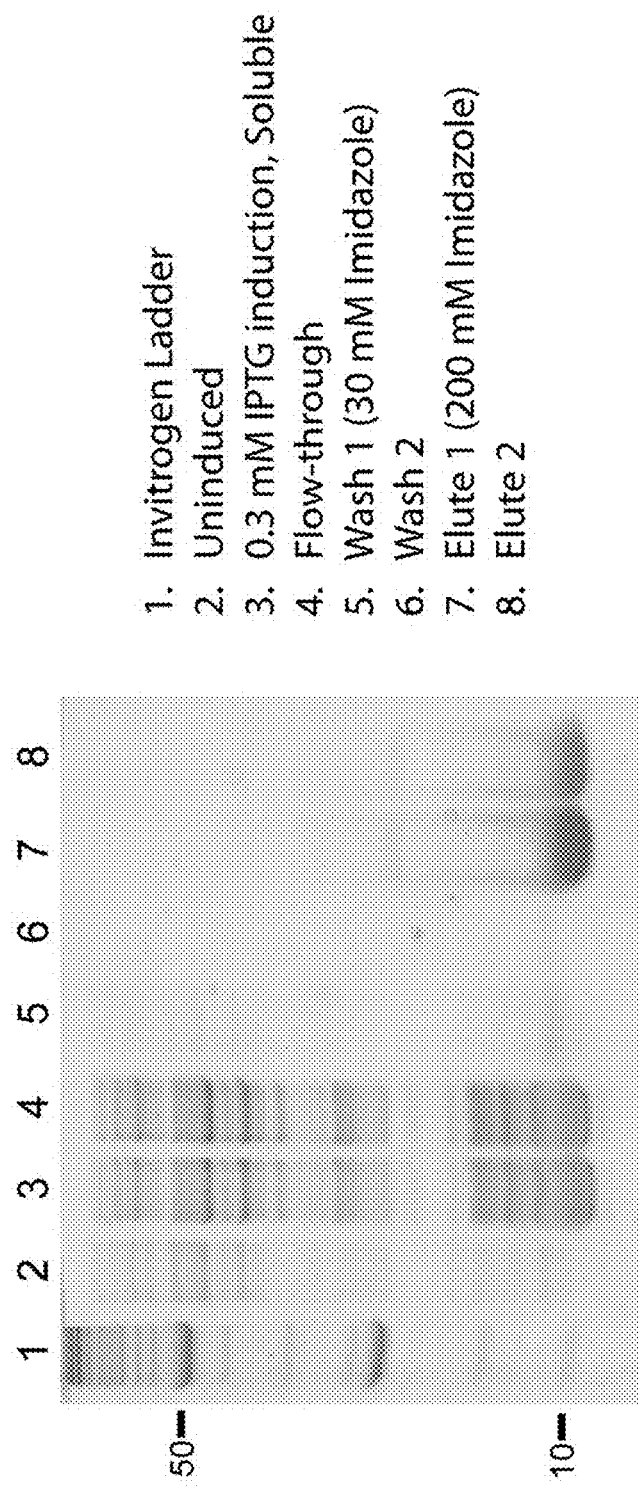
FIG. 23. Purification of the HLH-LZ region of Max for Expressed Protein Ligation.

In certain embodiments, a Max protein construct is created to express the HLH-LZ portion from residue 37 to the end of the leucine zipper. Residue 37 is mutated to cysteine so as to have a free N-terminal thiol for Expressed Protein Ligation (EPL). In certain embodiments, the C-terminal region contains an additional flanking sequence that includes a TEV-cleavable His-tag for purification. The protein is expressed in BL21 (DE3), the bacteria are sonication, the protein fragment is purified over Ni-NTA resin followed by analytical gel filtration (FIG. 23).

In certain embodiments, the EPL reaction is set up by adding two molar equivalents of the stapled peptide (i, i+4 Version 1) to the purified Max fragment.

In certain embodiments, stapled peptide are linked by a long PEG linker to the N-terminal end of the basic region to increase cellular uptake. For instance, the stapled peptide can be derived from Sin3, thereby causing recruitment of the Sin3 repressor complex to further functionalize the semi-synthetic product.

Other Proteins

Any protein may be modified and prepared using the inventive ligation system for preparing a stitched or stapled protein. Stapled versions of IL-13 and c-myc have been described herein for illustrative purposes only. As one of skill in the art would recognize, other proteins (e.g., proteins with greater than 50 amino acids) may be prepared using the inventive ligation method. In certain embodiments, the final protein includes greater than approximately 25, 30, 35, 40, 45, 50, 75, 100, 150, 200, 300, 400, 500, or more amino acids. The protein typically includes an α-helical portion that is stabilized using protein stapling or stitching. In certain embodiments, the α-helical portion is on the exterior of the protein. In certain embodiments, more than one α-helical portion is ligated onto the final protein. Exemplary types of proteins that may find use as therapeutic agents or research tools and would benefit from stapling or stitching include hormones, cytokines, antibodies, blood clotting factors, enzymes, transcription factors, oncoproteins, and receptors. In certain embodiments, the modified protein is a modified version of erythropoietin, alpha-interferon, beta-interferon, gamma-interferon, interleukin-1, interleukin-2, interleukin-4, interleukin-6, interleukin-10, interleukin-11, interleukin-12, colony stimulating factor, somatotropin, octreotride, growth hormone, insulin, factor VIIa, factor VIII, factor IX, von Willebrand factor, alteplase, urokinase, reteplase, tenecteplase, streptokinase, agalsidase beta, alglucerase, imiglucerase, alglucosidase alpha, idursulfase, galsulfase, and laronidase. In certain embodiments, the modified protein is a stapled or stitched antibody. In certain embodiments, the modified protein is a therapeutic antibody. In certain embodiments, the antibody is a monoclonal antibody. In certain embodiments, the stapled or stitched antibody is a modified version of rituxumab, cetuximab, trastuzumab, bevacizumab, tositumomab, gemtuzumab ozogamicin, ibritumomab tiuxetan, infliximab, adalimumab, natalizumab, remicade, efalizumab, xolair, ranibizumab, basiliximab, muromonab CD3, abciximab, and palivizumab.

Stitching or stapling may be used to alter a biological, physical, and/or chemical property of the protein. In certain embodiments, the stapling or stitching alters the biological activity of the protein. For example, stapling or stitching may result in the stapled or stitched protein not binding its biological target. The stapling or stitching may convert an agonist into an antagonist, or vice versa. In certain embodiments, the stapling or stitching does not alter the primary biological activity of the protein but instead stabilizes the protein. In certain embodiments, the stapling or stitching alters the pharmacodynamics or pharmacokinetics of the protein. Preferably, the resulting stapled or stitched protein is non-immunogenic.

Uses of Stapled or Stitched Proteins and Pharmaceutical Compositions Thereof

The invention further provides methods of treating a disease using a stitched or stapled protein. The method involves the administration of a therapeutically effective amount of the stitched or stapled protein to a subject (including, but not limited to a human or animal) in need of it.

The proteins and pharmaceutical compositions of the present invention may be used in treating or preventing any disease or conditions including anemia, asthma, inflammatory diseases (e.g., Crohn's disease, rheumatoid arthritis, psoriasis), diabetes, infections (e.g., skin infections, GI infection, urinary tract infections, genito-urinary infections, systemic infections, viral infections), proliferative diseases (e.g., cancer, benign neoplasms, diabetic retinopathy), and autoimmune diseases (e.g., rheumatoid arthritis, lupus). The inventive proteins and pharmaceutical compositions may be administered to animals, preferably mammals (e.g., domesticated animals, cats, dogs, mice, rats), and more preferably humans. Any method of administration may be used to deliver the inventive protein or pharmaceutical composition to the animal. In certain embodiments, the protein or pharmaceutical composition is administered orally. In other embodiments, the protein or pharmaceutical composition is administered parenterally.

The exact amount required will vary from subject to subject, depending on the species, age, and general condition of the subject, the particular protein, its mode of administration, its mode of activity, and the like. The proteins of the invention are preferably formulated in dosage unit form for ease of administration and uniformity of dosage. It will be understood, however, that the total daily usage of the proteins and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific protein employed; the specific composition employed; the age, body weight, general health, sex and diet of the patient; the time of administration, route of administration, and rate of excretion of the specific compound employed; the duration of the treatment; drugs used in combination or coincidental with the specific protein employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the proteins of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the proteins of the invention are mixed with solubilizing agents such an Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the proteins of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and *acacia, c)* humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active proteins can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active protein may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the proteins and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

These and other aspects of the present invention will be further appreciated upon consideration of the following Examples, which are intended to illustrate certain particular embodiments of the invention but are not intended to limit its scope, as defined by the claims.

EXAMPLES

Example 1

Semi-Synthetically Modified IL-13 Analogs

The cytokine IL-13 is strongly implicated in the pathogenesis of asthma. Interest exists in developing potent, selective, long-lasting, and non-immunogenic inhibitors of IL-13 signaling as a new therapeutic avenue in treating asthma. Using hydrocarbon stapling, IL-13 is converted from an agonist into an antagonist having the aforementioned properties through site-specific introduction of a stapled α-helix.

First, a semi-synthetic route to IL-13 analogs comprising a hydrocarbon staple on Helix-A is established. Second, a series of stapled IL-13 proteins differing in the location of the staple, their chemical composition, and stereochemical configuration is produced. Third, the binding of the stapled IL-13 analogs to IL-13Rα1 and IL-4Rα is characterized, and the structures of the relevant bound complexes is determined. Fourth, the ability of the stapled IL-13 analogs to induce or antagonize IL-13 signaling in cells is tested. Fifth, measurements of the pharmacokinetics in rats are obtained for a selected set of stapled IL-13 antagonists.

To establish a semi-synthetic route to IL-13 analogs comprising a hydrocarbon staple on helix-A, a construct of the IL-13 protein lacking helix A was overexpressed and purified. The protein was expressed without any amino acid changes or appended affinity tags. Three different routes were tested to produce the protein fragment at high expression levels to yield the desired protein fragment with the N-terminal cysteine required for the subsequent protein ligation step.

In one approach, the desired recombinant portion of IL-13 (Helices B-D) containing a Cys residue immediately after the start codon was cloned into a T7-inducible vector. This Cys residue is found in wild-type IL-13, and no mutations were introduced. Upon induction, N-terminal methionyl processing was expected to yield the desired N-terminal Cys that is necessary for Expressed Protein Ligation (EPL). Protein expression for an untagged version of the IL-$13_{26-112}$ construct under a T7-inducible promoter was tested under a variety of conditions (induction times, temperatures, and IPTG concentrations), see FIG. 14. Protein overexpression was not detected under any of thee conditions tested.

It has been reported that full-length IL-13 has not been successfully overexpressed in the absence of an affinity tag.

In a second approach, a variant full-length construct of IL-13 was fused to maltose binding protein (MBP). MBP promotes over-expression of the cytokine. A plasmid was designed to express full-length IL-13 fused to the C-terminus of MBP. A TEV cleavage site was inserted into the loop region of IL-13 between Helix-A and -B just before Cys 26, such that TEV cleavage is expected to separate Helix A from the desired Cys-terminated BCD fragment. This plasmid was co-expressed with a low-copy, constitutively expressed plasmid of TEV (pRK603). After T7 induction, intracellular TEV processing of the MBP-IL-13 fusion construct occurred, yielding the desired IL-$13_{26-112}$ construct of IL-13. Although this approach was previously used to purify full-length IL-13 construct from inclusion bodies, it was found that the truncated construct was present in the soluble fraction under the expression conditions used. Since Helix-A is involved in extensive core-packing interactions, it was thought that it is possible that this helix when provided in trans might still associate with the remainder of the protein, keeping both fragments in a soluble state. In this the case, the MBP portion fused to Helix-A can be used as bait for purification. The soluble portion was combined with amylose resin by batch binding to isolate the MBP-Helix-A fragment, and the Helices B-D construct was screened for its affinity as a secondary conjugate (FIG. 15). The desired IL-$13_{26-112}$ fragment was partially purified using this strategy, but the MBP-IL-13 fusion protein was also present.

As a route to improve the overall efficiency of intracellular TEV cleavage, a novel plasmid was designed in which TEV protease would directly be fused to the IL-$13_{26-112}$ construct downstream of a T7 promoter. Crystal structure analysis of TEV reveals that the active site is in close proximity to its C-terminus. It was reasoned that by adding a short linker sequence containing the consensus sequence for TEV recognition followed by the desired IL-$13_{26-112}$ construct, cleavage activity could be promoted since the protease substrate would be intra-molecularly positioned at the TEV active site immediately after protein expression. The TEV-IL-$13_{26-112}$ construct was generated to contain a short linker bearing the TEV recognition sequence immediately before Cys 26 of IL-13. Substrate cleavage efficiency was greatly enhanced after induction, and the desired IL-$13_{26-112}$ fragment was readily solubilized under weak denaturing conditions as an initial purification step (FIG. 16). A viable route for expression and purification of the IL-$13_{26-112}$ construct without the need for affinity tags or any other modifications was identified.

An alternative route that has also been explored is the recombinant expression of a portion of Helix-A along with the remainder of the protein. It was found that by doing this, the protein behaves similar to the full-length construct, and can therefore be isolated following urea washes of the insoluble fraction, yielding solubilization of the desired protein fragment in guanidine (FIG. 17). IL-13-MBP fusion constructs were co-expressed with a non-inducible, low-copy expression plasmid of TEV. The constructs were designed to start at either residue 9 or 12, which were both mutated to Cys residues for future applications in EPL. Both 12 kD constructs were isolated from the insoluble fraction following urea washes and guanidine solubilization.

Going forward with the construct starting at residue 12, the protein was further purified over sephacryl resin and filtered through a Centricon YM-30. The flow-through was applied to a Centricon YM-3. The concentrated product was then set up for an EPL ligation by adding two molar equivalents of the Boc-synthesized C-terminal thioester peptide containing the sequence for remainder of Helix A. Additionally, 4% thiophenol and 4% benzylmercaptan were added, and the reaction was left to shake for 3 days at 37° C. A ligation product was detected by SDS-PAGE analysis, where the ligated protein product migrated at a higher molecular weight than the unligated protein fragment (FIG. 18).

Synthesis of the non-natural amino acid, $S_5$, was scaled up to provide enough material for multiple syntheses, and the final product was Boc-protected. A stapled version of Helix-A was synthesized by Boc chemistry on S-trityl-mercaptopropionyl resin to yield a free C-terminal thioester after resin cleavage. Multiple variants of Helix-A and Helix-D are synthesized.

Full-length IL-13 was recombinantly expressed as an MBP-fusion construct in *E. coli*. The protein was purified over amylose resin, then treated with a 1:100 ratio of Factor Xa overnight at room temperature. The Factor Xa site was introduced immediately before $Cys_{26}$, yielding the IL-$13_{26-112}$ protein construct. A chemical ligation reaction was subsequently performed at room temperature and monitored for 3 days in 6 M guanidine hydrochloride (pH 8.5) using the stapled peptide STALRS$_5$LIES$_5$LVNITQNQKAAL (SEQ ID NO: 3). The stapled peptide was prepared using Boc chemistry on 3-S-trityl-mercaptopropionyl MBHA resin. Resin cleavage was performed using HF. See FIG. 13 for a gel demonstrating ligated product formation over time.

Based upon crystal structure analysis, IL-13 analogs were synthesized to contain the hydrocarbon staple at positions that would prevent IL-4R interactions while not interfering with core packing interactions. Before creating the final semi-synthetic ligation products, theoretical calculations and biophysical experiments were performed. A library of peptides containing i, i+4 staples at various positions in Helix-A were first analyzed (FIG. 19A). The non-natural amino acids were introduced at positions that are not involved in core-packing interactions of Il-13. Computational modeling was performed to predict the stabilizing effects of the hydrocarbon staple on secondary structure at varying positions in the helix (FIG. 19B). Monte Carlo simulations were performed to calculate the theoretical helicity and thermal stability of each variant. In parallel, each stapled peptide variant of Helix-A was also synthesized and purified by HPLC and analyzed by circular dichroism (FIG. 19C). It was found that as the staple was positioned closer to the C-terminus of Helix A, the alpha-helical content of the peptide was enhanced. The calculated predictions are in agreement with the experimentally measured effects for helix stabilization. Each variant is also synthesized to contain a C-terminal thioester for downstream EPL and biophysical characteristics of each semi-synthetic variant of IL-13.

Example 2

Chemical Modification of the DNA Binding Basic Region of Max

Max is a member of the bHLH-LZ (basic region-helix 1-loop-helix 2-leucine zipper) family of transcription factors. While Max can homodimerize and bind to specific Enhancer box (E box) sequences, Max is also an obligate partner for several members of the Myc family for E box binding. Max is constitutively expressed and is believed to establish a basal state of transcriptional activity for target genes that are also recognized by other Myc family members. When Myc family members are upregulated, these heterodimer complexes will compete with Max homodimers for transcriptional regulation, leading to transcriptional upregulation or repression of their target genes. Myc family members are responsible for transcriptional regulation of numerous key cellular processes including cell cycle regulation, apoptosis and metabolism, and deregulated activity of Myc family members has been associated with a variety of malignancies. Max homodimerization acts to repress cMyc activity and a dominant negative version of Max might be an antagonist for cMyc downregulation in an oncogenic state.

This example demonstrates the introduction of chemical modifications into the DNA binding basic region of Max (RAHHNALERKRR, SEQ ID NO: 2), see FIG. 20. It is thought that the basic region undergoes a disorder-to-order structural transition upon DNA binding, and therefore improved binding may become more favorable by locking these residues into a pre-binding state where the entropic penalty is removed. This can be accomplished by introducing non-natural amino acids within this region, then stapling the sequence into an alpha-helical structure via ring-closing metathesis chemistry. Other structural elements of Max are involved in protein-protein interactions for dimerization, and this dimerization is necessary in order to achieve a transcriptional response. These structural elements, namely the helix-loop helix (HLH) and leucine zipper (LZ) regions, were recombinantly expressed and ligated to the synthetic basic region of Max.

A panel of two i, i+4 peptides and one i, i+7 peptide derived from the basic region were synthesized and characterized. All peptides were synthesized with an N-terminal PEG-3 linker to increase solubility while also distancing the FITC group from the DNA binding region. FIG. 21 shows structures of synthesized basic region peptides. Non-natural amino acids were introduced at positions that are not involved in DNA binding. The terminal olefins were linked together using ring-closing metathesis chemistry to promote stability of an alpha-helical secondary structure.

Each of the synthesized peptides were purified by HPLC and biochemically characterized. Each peptide was diluted in water to a final concentration of 100 uM using the extinction coefficient of FITC at 495 nm in 50 mM $NaH_2PO_4$, pH 8.0. As shown in FIG. 22A, circular dichroism measurements were taken for each peptide and revealed that the unmodified basic region peptide is disordered in solution. All three stapled versions demonstrate a CD profile indicative of an alpha-helix. As shown in FIG. 22B, based upon the molar ellipticity measurements at 222 nm the overall percent helicity of each peptide was determined and found to range between 25 and 30 percent. Based upon these results, each of the chemically modified peptides appeared to be structurally similar to one another, and all three versions had improved secondary structure relative to the unmodified counterpart. One peptide, i, i+4 version 1, was chosen to be synthesized so as to contain a C-terminal thioester. The peptide was synthesized using t-Boc chemistry on 3-S-trityl-mercaptopropionyl resin. The peptide was purified by HPLC and the desired product was confirmed by LC/MS analysis.

A Max protein construct was created to express the HLH-LZ portion from residue 37 to the end of the leucine zipper. Residue 37 was mutated to cysteine so as to have a free N-terminal thiol for Expressed Protein Ligation (EPL). The C-terminal region contained an additional flanking sequence that included a TEV-cleavable His-tag for purification. The protein was expressed in BL21 (DE3) cells and induced at $OD_{600}=0.6$ with a final concentration of 0.2 mM IPTG for 4 hours at 30 degrees. After sonication, the protein fragment was purified over Ni-NTA resin followed by analytical gel filtration (FIG. 23). The protein fragment containing an N-terminal Cys was and purified over Ni-NTA resin followed by analytical gel filtration.

Figure 24:
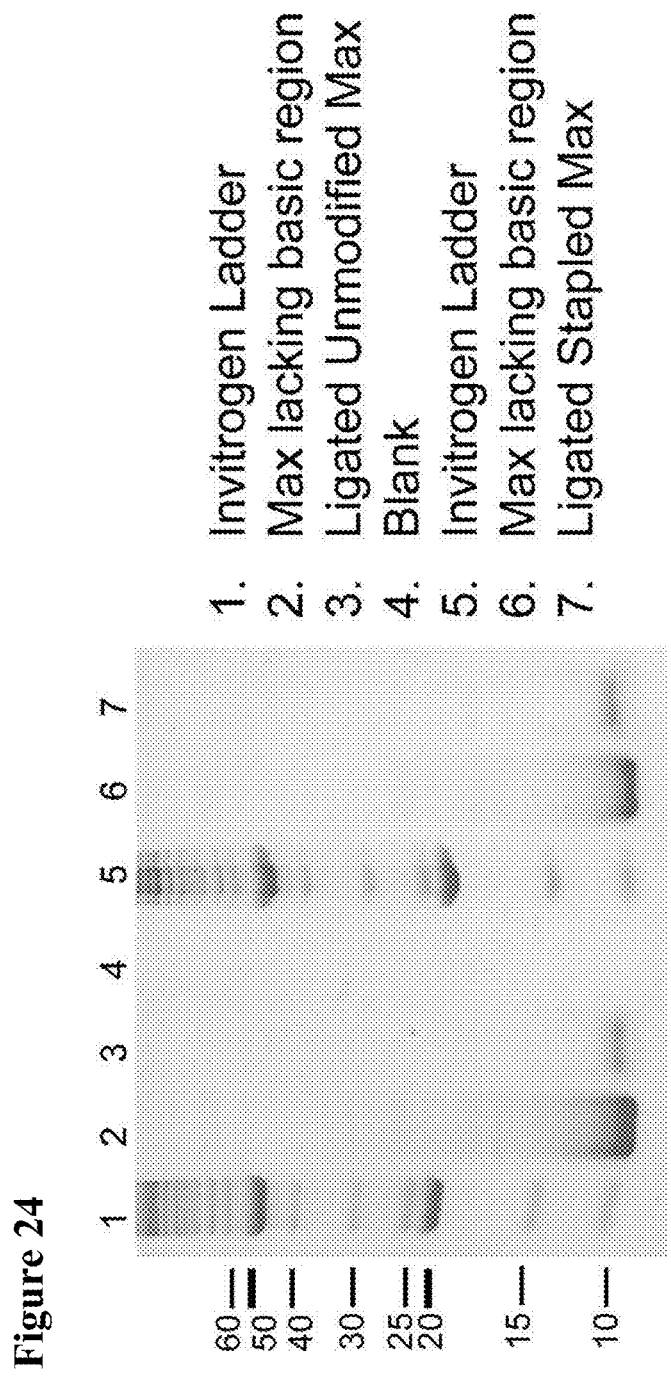
FIG. 24. Expressed protein ligation of the HLH-LZ region of Max with a stapled basic region peptide (or an unmodified peptide control).

The EPL reaction was set up by adding two molar equivalents of the stapled peptide (i, i+4 Version 1) to the purified Max fragment in 6 M guanidine, pH 6.5 along with 4% thiophenol and 4% benzylmercaptan. The reaction proceeded for 3 days at 37 degrees with shaking. Ligation products were evident by SDS-PAGE analysis after 48 hours (FIG. 24).

Figure 25:
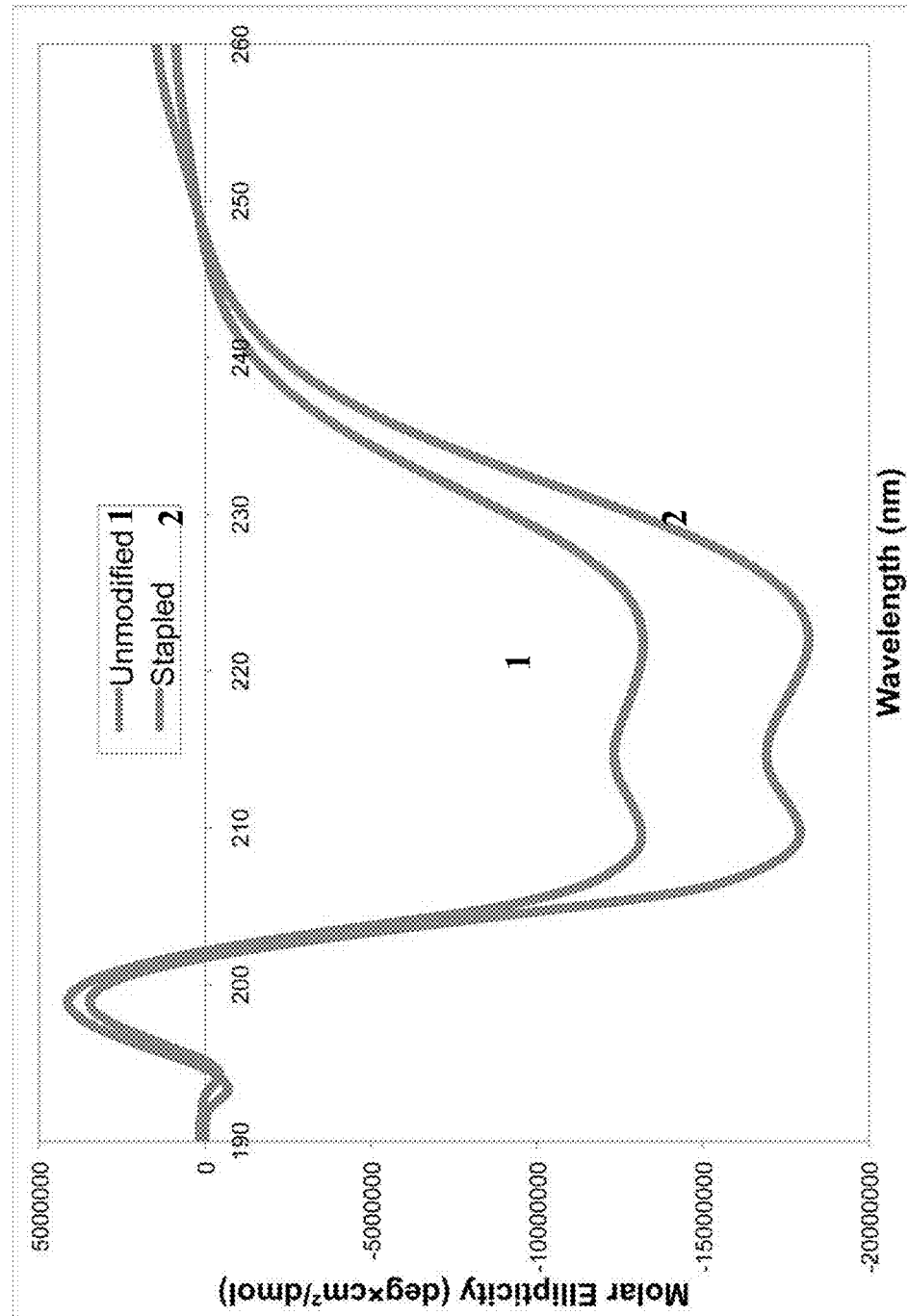
FIG. 25. Circular dichroism measurements of the semi-synthetic ligation products of Max. Either an unmodified or stapled basic region peptide was ligated to the HLH-LZ protein fragment of Max.

The semi-synthetic protein products were characterized by circular dichroism, as shown in FIG. 25. Either an unmodified or stapled basic region peptide was ligated to the HLH-LZ protein fragment of Max. It was found that, at the level of the protein, overall alpha-helical secondary structure was increased with the addition of the stapled basic region peptide as compared to its unstapled counterpart.

Figure 26:
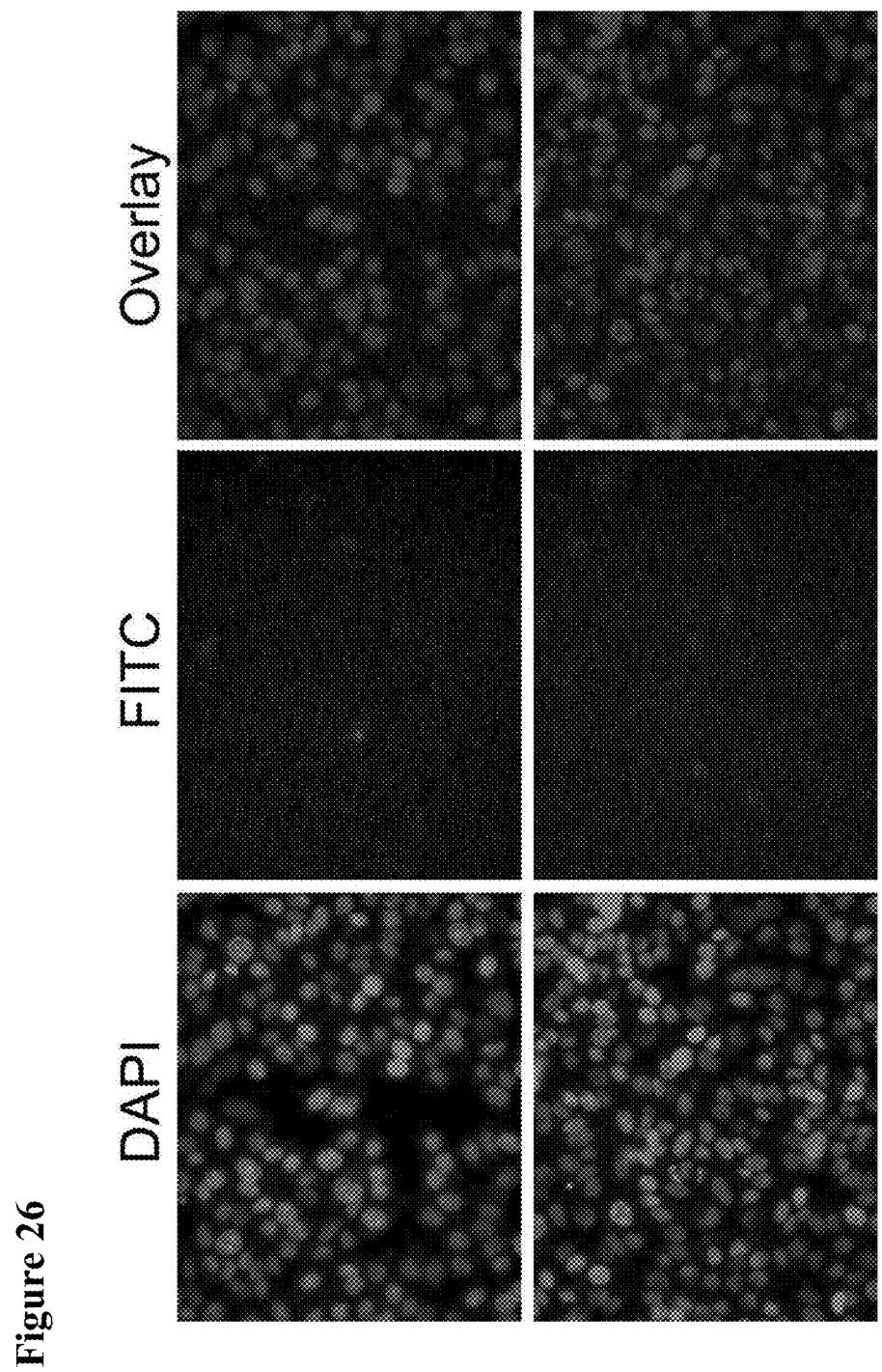
FIG. 26. Cellular access of semi-synthetic Max. Photographs of immunofluorescent cells.

Cellular uptake of the semi-synthetic Max proteins was also measured. These 10 kD proteins contained an N-terminal FITC group. Jurkat cells were treated with either 2.5 or 5 µM protein for 12 hours at 37 degrees. Cellular access of semi-synthetic Max is shown in FIG. 26, which shows a limited amount of FITC was evident in cells after this time course.

It was observed that stapled peptides alone have significantly increased cellular access and that the addition of a stapled peptide to another moiety also increases its level of access. Stapled peptide are linked by a long PEG linker to the N-terminal end of the basic region to increase cellular uptake. For instance, the stapled peptide can be derived from Sin3, thereby causing recruitment of the Sin3 repressor complex to further functionalize the semi-synthetic product. In this manner, a designer transcription factor is engineered that triggers transcriptional repression instead of activation.

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method of preparing a stabilized, non-immunogenic, and folded protein comprising a stitched α-helical peptide segment, the method comprising steps of:

providing a stitched α-helical peptide segment, wherein the stitched α-helical peptide segment is of formula:

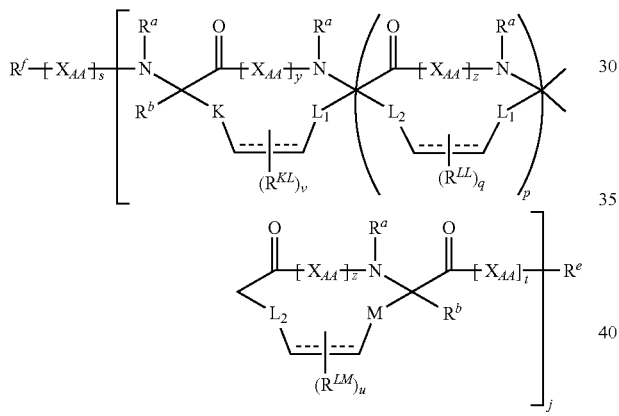

wherein each instance of K, $L_1$, $L_2$, and M, is, independently, a bond, cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene;

each instance of $R^a$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; or $R^a$ is a suitable amino protecting group;

each instance of $R^b$ is, independently, a suitable amino acid side chain; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^e$ is, independently, —$R^E$, —$OR^E$, —$N(R^E)_2$, or —$SR^E$, wherein each instance of $R^E$ is, independently, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino, or thiol protecting group; or two $R^E$ groups together form a substituted or unsubstituted 5-to 6-membered heterocyclic or heteroaromatic ring;

each instance of $R^f$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a linker, wherein the linker is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ together form a substituted or unsubstituted 5- to 6-membered heterocyclic or heteroaromatic ring;

each instance of $R^{KL}$, $R^{LL}$, and $R^{LM}$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro;

or two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; two adjacent $R^{LL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; or two adjacent $R^{LM}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring;

each instance of $X_{AA}$ is, independently, a natural or unnatural amino acid;

each instance of y and z is, independently, an integer between 2 to 6;

each instance of j is, independently, an integer between 1 to 10;

each instance of p is, independently, an integer between 0 to 10;

each instance of s and t is, independently, an integer between 0 and 100;

each instance of u, v, and q, is, independently, an integer between 0 to 2; and wherein ======== corresponds to a single or double bond;

providing a second protein to which the stitched α-helical peptide segment is to be ligated, wherein the second protein is produced recombinantly or purified from a natural source; and ligating the stitched α-helical peptide segment to the second protein.

2. The method of claim 1, wherein the stitched α-helical peptide segment is less than 30 amino acids in length.

3. The method of claim 1, wherein the stitched peptide is of formula:

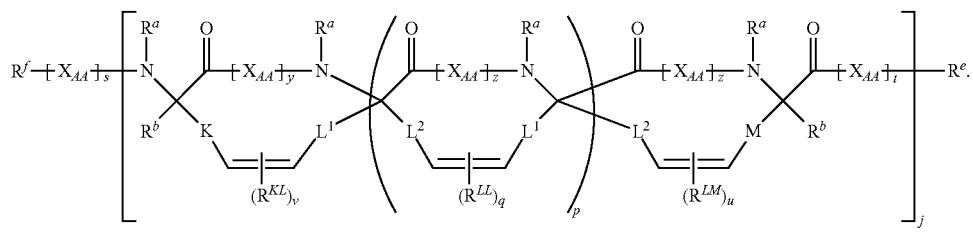

4. The method of claim 1, wherein the stitched peptide is of formula:

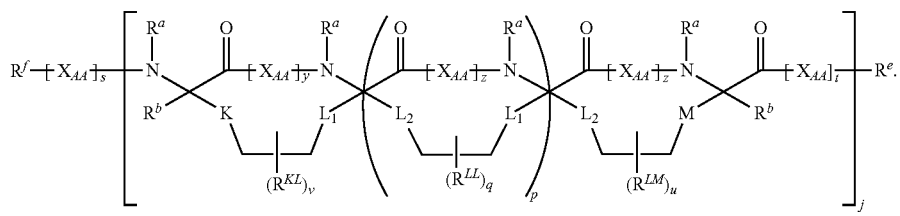

5. The method of claim 1, wherein the step of providing a stitched α-helical peptide segment comprises steps of:

synthetically producing an unstitched peptide segment, wherein the peptide segment comprises unnatural amino acid residues suitable for stitching; and stitching the unstitched peptide.

6. The method of claim 1, wherein the step of providing a stitched α-helical peptide segment comprises steps of:

providing a peptide with at least two α-methyl,α-alkenylglycine or α-hydro,α-alkenylglycine residues and at least one dialkenylglycine residue; and stitching the peptide using a Grubbs catalyst to form at least two macrocyclic hydrocarbon staples.

7. The method of claim 6, wherein the two α-methyl,α-alkenylglycine or α-hydro,α-alkenylglycine residues are at positions i and i+3, at positions i and i+4, and/or at positions i and i+7.

8. The method of claim 6, wherein the α-methyl,α-alkenylglycine or α-hydro, α-alkenylglycine residue is of the formula:

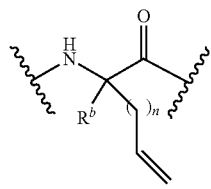

wherein n is an integer between 1 and 10, inclusive; and $R^b$ is H or methyl.

9. The method of claim 1, wherein the second protein is prepared recombinantly.

10. The method of claim 1, wherein the second protein is treated with a protease to yield an N-terminal cysteine.

11. The method of claim 10, wherein the protease is Factor Xa, Tobacco Etch Virus, enterokinase, or ubiquitin C-terminal hydrolase.

12. The method of claim 1, wherein the second protein is produced by having cysteine as the second residue in an expression construct following an N-terminal methionine; wherein the methionine is processed during protein expression to yield an N-terminal cysteine.

13. The method of claim 1, wherein the step of ligating comprises ligating using Expressed Protein Ligation (EPL).

14. The method of claim 1, wherein the step of ligating produces a scarless protein.

15. The method of claim 1, wherein stitched protein comprises a stitched version of IL-13.

16. The method of claim 15, wherein Helix A of IL-13 is stitched.

17. The method of claim 15, wherein Helix D of IL-13 is stitched.

18. The method of claim 1, wherein the stitched protein comprises a stitched version of c-myc, a stitched version of insulin, a stitched version of a transcription factor, or a stitched version of a cytokine.

19. The method of claim 1, wherein the stitched α-helical peptide segment is less than 25 amino acids in length.

20. The method of claim 1, wherein the stitched α-helical peptide segment is less than 20 amino acids in length.

21. The method of claim 1, wherein the stitched α-helical peptide is a bifunctional peptide.

22. A stitched protein made by the method of claim 1.

* * * * *

SEQUENCE LISTING

```
<160> NUMBER OF SEQ ID NOS: 8

<210> SEQ ID NO 1
<211> LENGTH: 112
<212> TYPE: PRT
<213> ORGANISM: artificial sequence
<220> FEATURE:
<223> OTHER INFORMATION: Synthetic Peptide, human IL-13
```

<400> SEQUENCE: 1

Gly Pro Val Pro Pro Ser Thr Ala Leu Arg Glu Leu Ile Glu Leu
1               5                   10                  15

Val Asn Ile Thr Gln Asn Gln Lys Ala Pro Leu Cys Asn Gly Ser Met
                20                  25                  30

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65              70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

<210> SEQ ID NO 2
<211> LENGTH: 12
<212> TYPE: PRT
<213> ORGANISM: artificial sequence
<220> FEATURE:
<223> OTHER INFORMATION: Synthetic Peptide, basic DNA binding region of
      Max with mutation sites at positions 2, 6, and 10

<400> SEQUENCE: 2

Arg Ala His His Asn Ala Leu Glu Arg Lys Arg Arg
1               5                   10

<210> SEQ ID NO 3
<211> LENGTH: 22
<212> TYPE: PRT
<213> ORGANISM: artificial sequence
<220> FEATURE:
<223> OTHER INFORMATION: Synthetic Peptide, IL-13 Helix-A, containing S5
      at positions 6 and 10 for peptide stapling
<220> FEATURE:
<221> NAME/KEY: MISC_FEATURE
<222> LOCATION: (6)..(6)
<223> OTHER INFORMATION: X = S5, (S)-2-amino-2-methylhept-6-enoic acid
<220> FEATURE:
<221> NAME/KEY: MISC_FEATURE
<222> LOCATION: (10)..(10)
<223> OTHER INFORMATION: X = S5, (S)-2-amino-2-methylhept-6-enoic acid

<400> SEQUENCE: 3

Ser Thr Ala Leu Arg Xaa Leu Ile Glu Xaa Leu Val Asn Ile Thr Gln
1               5                   10                  15

Asn Gln Lys Ala Ala Leu
            20

<210> SEQ ID NO 4
<211> LENGTH: 22
<212> TYPE: PRT
<213> ORGANISM: artificial sequence
<220> FEATURE:
<223> OTHER INFORMATION: synthetic peptide, IL-13 Helix-A

<400> SEQUENCE: 4

Ser Thr Ala Leu Arg Glu Leu Ile Glu Glu Leu Val Asn Ile Thr Gln
1               5                   10                  15

Asn Gln Lys Ala Pro Leu
            20

```
<210> SEQ ID NO 5
<211> LENGTH: 20
<212> TYPE: PRT
<213> ORGANISM: artificial sequence
<220> FEATURE:
<223> OTHER INFORMATION: synthetic peptide, IL-13 Helix-A

<400> SEQUENCE: 5

Ala Leu Arg Glu Leu Ile Glu Glu Leu Val Asn Ile Thr Gln Asn Gln
1               5                   10                  15

Lys Ala Pro Leu
            20

<210> SEQ ID NO 6
<211> LENGTH: 24
<212> TYPE: PRT
<213> ORGANISM: artificial sequence
<220> FEATURE:
<223> OTHER INFORMATION: synthetic peptide, c-Myc bHLH region (residues
      369-419), containing non-natural amino acids for peptide stapling
<220> FEATURE:
<221> NAME/KEY: MISC_FEATURE
<222> LOCATION: (10)..(10)
<223> OTHER INFORMATION: X = non-natural amino acid
<220> FEATURE:
<221> NAME/KEY: MISC_FEATURE
<222> LOCATION: (14)..(14)
<223> OTHER INFORMATION: X = non-natural amino acid
<220> FEATURE:
<221> NAME/KEY: MISC_FEATURE
<222> LOCATION: (18)..(18)
<223> OTHER INFORMATION: X = non-natural amino acid

<400> SEQUENCE: 6

Cys Val Gln Ala Glu Glu Gln Lys Leu Xaa Ser Glu Glu Xaa Leu Leu
1               5                   10                  15

Arg Xaa Arg Arg Glu Gln Leu Lys
            20

<210> SEQ ID NO 7
<211> LENGTH: 24
<212> TYPE: PRT
<213> ORGANISM: artificial sequence
<220> FEATURE:
<223> OTHER INFORMATION: synthetic peptide, c-Myc bHLH region (residues
      369-419), containing non-natural amino acids for peptide stapling
<220> FEATURE:
<221> NAME/KEY: MISC_FEATURE
<222> LOCATION: (6)..(6)
<223> OTHER INFORMATION: X = non-natural amino acid
<220> FEATURE:
<221> NAME/KEY: MISC_FEATURE
<222> LOCATION: (10)..(10)
<223> OTHER INFORMATION: X = non-natural amino acid
<220> FEATURE:
<221> NAME/KEY: MISC_FEATURE
<222> LOCATION: (14)..(14)
<223> OTHER INFORMATION: X = non-natural amino acid

<400> SEQUENCE: 7

Cys Val Gln Ala Glu Xaa Gln Lys Leu Xaa Ser Glu Glu Xaa Leu Leu
1               5                   10                  15

Arg Lys Arg Arg Glu Gln Leu Lys
            20

<210> SEQ ID NO 8
<211> LENGTH: 24
<212> TYPE: PRT
<213> ORGANISM: artificial sequence
```

```
<220> FEATURE:
<223> OTHER INFORMATION: synthetic peptide, c-Myc bHLH region (residues
      369-419), containing non-natural amino acids for peptide stapling
<220> FEATURE:
<221> NAME/KEY: MISC_FEATURE
<222> LOCATION: (14)..(14)
<223> OTHER INFORMATION: X = non-natural amino acid
<220> FEATURE:
<221> NAME/KEY: MISC_FEATURE
<222> LOCATION: (18)..(18)
<223> OTHER INFORMATION: X = non-natural amino acid

<400> SEQUENCE: 8

Cys Val Gln Ala Glu Glu Gln Lys Leu Ile Ser Glu Glu Xaa Leu Leu
1               5                   10                  15

Arg Xaa Arg Arg Glu Gln Leu Lys
            20
```